United States Patent
Heine et al.

(10) Patent No.: US 11,339,161 B2
(45) Date of Patent: May 24, 2022

(54) TRIAZOLO PYRIDINES AS MODULATORS OF GAMMA-SECRETASE

(71) Applicant: Boehringer Ingelheim International GmbH, Ingelheim am Rhein (DE)

(72) Inventors: Niklas Heine, Biberach an der Riss (DE); Christian Eickmeier, Mittelbiberach (DE); Kai Gerlach, Mittelbiberach (DE); Ulrike Gross, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 181 days.

(21) Appl. No.: 16/955,093

(22) PCT Filed: Dec. 18, 2018

(86) PCT No.: PCT/EP2018/085364
§ 371 (c)(1),
(2) Date: Jun. 18, 2020

(87) PCT Pub. No.: WO2019/121596
PCT Pub. Date: Jun. 27, 2019

(65) Prior Publication Data
US 2021/0017173 A1    Jan. 21, 2021

(30) Foreign Application Priority Data
Dec. 19, 2017    (EP) .................................... 17208420

(51) Int. Cl.
*C07D 471/04*    (2006.01)
*A61P 25/28*    (2006.01)

(52) U.S. Cl.
CPC ............ *C07D 471/04* (2013.01); *A61P 25/28* (2018.01)

(58) Field of Classification Search
CPC ...................................................... A61P 25/28
USPC ........................................................ 514/303
See application file for complete search history.

(56) References Cited

U.S. PATENT DOCUMENTS 8,609,687 B2 * 12/2013 Zhu .................. A61P 35/04
546/119

FOREIGN PATENT DOCUMENTS

WO    2010010184    1/2010

OTHER PUBLICATIONS

Douxfils, Association Between BCR-ABL Tyrosine Kinase Inhibitors for Chronic Myeloid Leukemia and Cardiovascular Events, American Medical Assoc, vol. 5, 2016.
Hayman, VEGF Inhibition, Hypertension and Renal Toxicity, Curr. Oncol. Report, vol. 14, 2012.
Peng, Inactivation of focal adhesion kinase in cardiomyocytes promotes eccentric cardiac hypertropy and fibrosis in mice, JCI, vol. 116, 2006.
Cervantes, Phase I Pharmacokinetic/Pharmacodynnamic Study of MLN8237, an Investigations, Oral, Selective Aurora A Kinase Inhibitor, in Patients with Advanced Solid tumors Cancer Therapy, Clinical, Clinical Cancer Research, 2012.
Dolamanov, OLEX2:A complete structure solution, refinement and analysis program, Applied Crystallography, 2008.
Sheldrick, SHELXT-Integrated Space groupand crystal structure determination, Acta Crytallographica, 2014.
Sheldrick, a short history of SHELX, Foundations of Crysatallography, 2008, p. 112-122.

* cited by examiner

*Primary Examiner* — Niloofar Rahmani
(74) *Attorney, Agent, or Firm* — David L. Kershner

(57) ABSTRACT

The present invention relates to triazolo pyridines of formula (II) and their use as modulators of #-secretase. In particular, the present invention relates to compounds which interfere with #-secretase and/or its substrate and therefore modulate the formation of Aβ peptides. Accordingly these compounds can be used for the treatment of Aβ-related pathologies, e.g. Alzheimer's disease.

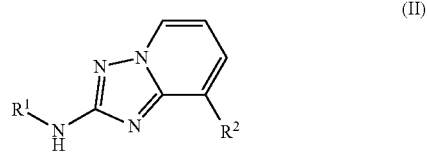

(II)

7 Claims, 1 Drawing Sheet

X-Ray structure of compound R-61

TRIAZOLO PYRIDINES AS MODULATORS OF GAMMA-SECRETASE

The present invention relates to triazolo pyridines and their use as modulators of γ-secretase. In particular, the present invention relates to compounds which interfere with γ-secretase and/or its substrate and therefore modulate the formation of Aβ peptides. Accordingly these compounds can be used for the treatment of Aβ-related pathologies, e.g. Alzheimer's disease.

Alzheimer's disease (AD) is the most prevalent form of dementia. This neurodegenerative disorder is characterized by two major pathologies, β-amyloid deposits and neurofibrillary tangles. Clinically, AD is characterized by the loss of memory, cognition, reasoning, judgment as well as orientation. As the disease progresses, further abilities are lost until a global impairment of multiple cognitive functions occur. These cognitive losses take place gradually, but typically lead to severe impairment and eventual death in 4-12 years.

β-amyloid deposits are predominantly formed from aggregated Aβ peptide. The Aβ peptide is formed from amyloid precursor protein (APP) through two independent proteolytic events involving β-secretase followed by γ-secretase. Variability in the site of proteolysis via γ-secretase results in Aβ species of variable length, the most predominant forms of which are Aβ38, Aβ40 and Aβ42. The secreted Aβ then aggregates into oligomeric species, which further aggregate to ultimately form the Aβ deposits detected in the brains of AD patients. The aggregated oligomeric species are widely believed to be the key neurotoxic agent responsible for the neurodegeneration detected in the brains of AD patients. Of the various Aβ species generated by γ-secretase, Aβ42 has been demonstrated to be the most aggregation prone as well as the most neurotoxic Aβ species. Furthermore, human genetics strongly supports a key role of Aβ42 as a key mediator of AD pathogenesis. More than 150 different mutations causing familial AD are known which result from either an increase in the ratio of Aβ42/Aβ40 peptides produced or increase the intrinsic aggregation propensity of Aβ. Based on this knowledge, therapeutic approaches aimed at lowering levels of Aβ42 are considered promising.

β-amyloid deposits and vascular amyloid angiopathy have also been characterized in the brains of patients with Trisomy 21 (Down's Syndrome), Hereditary Cerebral Hemorrhage with Amyloidosis of the Dutch-type (HCHWA-D), and other neurodegenerative disorders.

γ-Secretase inhibitors completely inhibit the cleavage of APP as well as all other substrates of γ-secretase. This inhibition leads to a simultaneous inhibition of the production of all AP species. As opposed to γ-secretase inhibitors, γ-secretase modulators preferentially block the production of the neurotoxic Aβ42 species while not inhibiting APP cleavage and thereby the generation of all Aβ species. Furthermore, γ-Secretase modulators do not inhibit the cleavage of other γ-secretase substrates, thereby diminishing the possibility of side effects.

WO2009/155551 discloses compounds of generic formula (I)

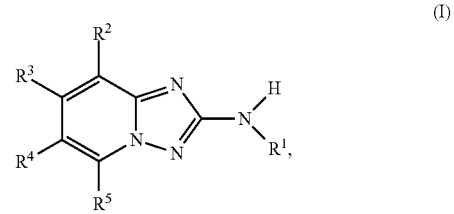

(I)

which are JAK kinase inhibitors for use in the treatment of myeloproliferative diseases and Alzheimer's disease. The specific examples disclosed in WO2009/155551 exhibit phenyl or 5- or 6-membered heteroaryl as R' of formula (I). Further, the examples 263, 293 and 302 exhibit fused heteroaryl substituents as R' (table 1).

TABLE 1

Examples of WO2009/155551 exhibiting fused heteroaryl substituents as $R^1$ of formula (I)

| Example no. in WO2009/155551 | Structure |
| --- | --- |
| 263 | 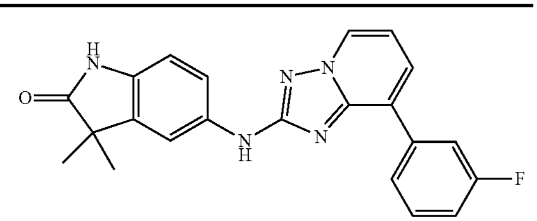 |
| 293 | 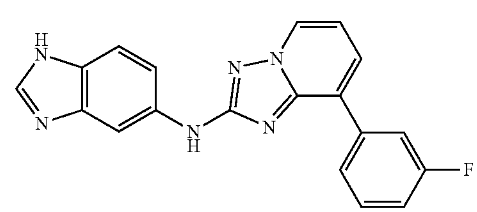 [SMILES: Fc1cccc(-c2cccn3nc(Nc4ccc5[nH]cnc5c4)nc23)c1] |

TABLE 1-continued

Examples of WO2009/155551 exhibiting fused heteroaryl substituents as $R^1$ of formula (I)

| Example no. in WO2009/155551 | Structure |
|---|---|
| 302 | 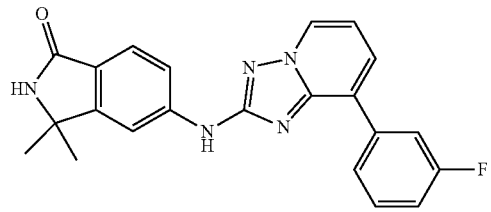 [SMILES: CC1(C)NC(=O)c2ccc(Nc3nc4c(-c5cccc(F)c5)cccn4n3)cc21] |

Examples 263, 293 and 302 of WO2009/155551 show a high degree of unselective kinase inhibition (tables 2 and 6), including the inhibition of tyrosine kinases from the FGFR, VEGFR and PDGFR families as well as FAK. Additionally, certain serine/threonine kinases such as Aurora A are also inhibited by these compounds.

Even more selective kinase inhibitors of the FGFR or VEGFR families have demonstrated cardiovascular side effects and nephrotoxicity (vascular occlusion and hypertension) in clinical trials. (Douxfils J, Haguet H, Mullier F, Chatelain C, Graux C and Dogné J M: Association between BCR-ABL tyrosine kinase inhibitors for chronic myeloid leukemia and cardiovascular events, major molecular response, and overall survival: A systematic review and meta-analysis. *JAMA Oncol.* 2016; 5: 625-632. Hayman S R, Leung N, Grande J P and Garovic V D: VEGF inhibition, hypertension, and renal toxicity. *Curr Oncol Rep.* 2012; 14: 285-294.)

In addition, inactivation of FAK in mouse cardiomyocytes led to cardiohypertrophy and fibrosis. (Peng X1, Kraus M S, Wei H, Shen T L, Pariaut R, Alcaraz A, Ji G, Cheng L, Yang Q, Kotlikoff M I, Chen J, Chien K, Gu H and Guan J L. Inactivation of focal adhesion kinase in cardiomyocytes promotes eccentric cardiac hypertrophy and fibrosis in mice. *J Clin Invest.* 2006; 116: 217-227.) Moreover, an Aurora A kinase inhibitor demonstrated numerous side effects in a phase I clinical trial, ranging from thrombocytopenia, neutropenia, stomatitis to diarrhoea. (Cervantes A, Elez E, Roda D, Ecsedy J, Macarulla T, Venkatakrishnan K, Rosello S, et al. Phase I pharmacokinetic/pharmacodynamic study of MLN8237, an investigational, oral, selective Aurora A kinase inhibitor, in patients with advanced solid tumors. *Clin Cancer Res.* 2012; 18: 4764-4774.)

Therefore, these data suggest that compounds (such as examples 263, 293 and 302 of WO2009/155551) that inhibit kinases of the FGFR/VEGFR family, FAK or Aurora A, will show numerous undesirable side effects.

Compounds of the present invention are generically encompassed by formula (I) of WO2009/155551. The compounds of the present invention differ structurally from the examples 263, 293 and 302 explicitly disclosed in WO2009/155551 in that they contain a substituted 4,5,6,7-tetrahydro-1H-indazole, 4,5,6,7-tetrahydro-1H-benzotriazole, 5,6,7,8-tetrahydro-[1,2,4]triazolo[4,3-a]pyridine, 4,5,6,7-tetrahydro-[1,2,3]triazolo[1,5-a]pyridine, or 1H-indazole in place of the benzimidazolyl, 1,3-dihydroindol-2-on-5-yl or 2,3-dihydro-isoindol-1-on-5-yl moiety:

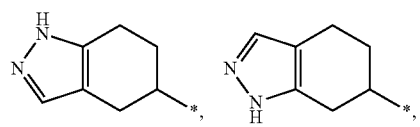

4,5,6,7-Tetrahydro-1H indazol-5-yl, 4,5,6,7-Tetrahydro-1H indazol-6-yl,

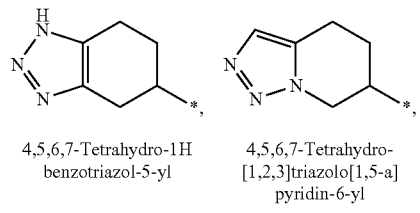

4,5,6,7-Tetrahydro-1H benzotriazol-5-yl, 4,5,6,7-Tetrahydro-[1,2,3]triazolo[1,5-a]pyridin-6-yl

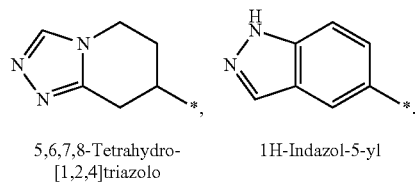

5,6,7,8-Tetrahydro-[1,2,4]triazolo[4,3-a]pyridin-7-yl, 1H-Indazol-5-yl.

The structural differences unexpectedly result in an increase in selectivity over ABL1, AURKA (Aurora A), CDK5/p35, CSF1R (FMS), FGFR1, FLT4 (VEGFR3), LYN B, MAP4K2 (GCK), PDGFRA (PDGFR alpha), PTK2 (FAK), RET, RPS6 KB1 (p70S6K), FGFR2, KDR (VEGFR2) or MAP4K4 (HGK). Additionally, the compounds have surprisingly been found to be potent modulators of γ-secretase (tables 2, 4a, 6 and 7), whereas the specific examples 263, 293 and 302 of WO2009/155551 do not show any modulation (examples 293, 302) or rather poor modulation (example 263) of γ-secretase (table 4b).

TABLE 2

Summary of kinase activity-comparison of reference compounds 263, 293 and 302
of WO2009/155551 with selected compounds of the present invention (overview of tables 6 and 7).

| Example no. | Kinases tested | | | | | | | |
|---|---|---|---|---|---|---|---|---|
| | ABL1 | AURKA (Aurora A) | CDK5/p35 | CSF1R (FMS) | FGFR1 | FGFR2 | FLT4 (VEGFR3) | KDR (VEGFR2) |
| Cpd. 263 in WO09155551 | ++ | ++ | ++ | ++ | ++ | ++ | ++ | ++ |
| Cpd. 293 in WO09155551 | ++ | ++ | ++ | ++ | ++ | ++ | ++ | ++ |
| Cpd. 302 in WO09155551 | ++ | ++ | ++ | ++ | ++ | ++ | ++ | ++ |
| 9 | + | + | + | ++ | − | + | ++ | − |
| 10 | − | − | + | + | − | − | − | − |
| 40 | − | − | + | − | − | − | − | − |
| 42 | − | − | − | − | − | − | − | − |
| R-42 | − | − | − | − | − | − | − | − |
| 43 | − | − | − | − | − | − | − | − |
| 44 | − | − | − | + | − | − | + | − |
| 45 | − | − | − | + | − | − | − | − |
| 46 | − | − | − | − | − | − | − | − |
| 47 | − | − | − | − | − | − | − | − |
| 48 | − | − | − | − | − | − | − | − |
| 49 | − | − | − | − | − | − | − | − |
| 51 | − | − | − | − | − | − | − | − |
| 54 | − | − | − | − | − | − | − | − |
| 55 | − | − | − | − | − | − | + | − |
| 56 | − | − | + | + | − | − | − | − |
| 57 | − | − | − | + | − | − | + | − |
| 59 | − | − | − | + | − | − | − | − |
| R-61 | − | − | − | − | − | − | − | − |
| S-61 | − | − | − | − | − | − | − | − |
| 63 | − | − | + | + | − | − | − | − |
| 67 | − | − | − | − | − | − | − | − |
| 68 | − | − | + | + | − | − | + | − |
| 69 | − | − | − | − | − | − | − | − |
| 70 | − | + | + | ++ | − | − | − | − |
| 71 | − | + | + | + | − | − | + | − |
| 73 | − | ++ | + | + | − | − | + | − |

| Example no. | Kinases tested | | | | | | |
|---|---|---|---|---|---|---|---|
| | LYN B | MAP4K2 (GCK) | MAP4K4 (HGK) | PDGFRA (PDGFR alpha) | PTK2 (FAK) | RET | RPS6KB1 (p70S6K) |
| Cpd. 263 in WO09155551 | ++ | ++ | ++ | ++ | ++ | ++ | ++ |
| Cpd. 293 in WO09155551 | ++ | ++ | ++ | ++ | ++ | ++ | ++ |
| Cpd. 302 in WO09155551 | ++ | ++ | ++ | ++ | ++ | ++ | ++ |
| 9 | − | + | − | + | − | − | − |
| 10 | − | − | − | − | − | − | − |
| 40 | − | − | − | + | − | − | − |
| 42 | − | − | − | − | − | − | − |
| R-42 | − | − | − | + | − | − | − |
| 43 | − | − | − | + | − | − | − |
| 44 | − | − | − | − | − | − | − |
| 45 | − | − | − | − | − | − | − |
| 46 | − | − | − | + | − | − | − |
| 47 | − | − | − | − | − | − | − |
| 48 | − | − | − | + | − | − | − |
| 49 | − | − | − | + | − | − | − |
| 51 | − | − | − | − | − | − | − |
| 54 | − | − | − | − | − | − | − |
| 55 | − | − | − | + | − | − | − |
| 56 | − | − | − | + | − | − | − |
| 57 | − | − | − | + | − | − | − |
| 59 | − | − | − | + | − | − | − |
| R-61 | − | − | − | − | − | − | − |
| S-61 | − | − | − | − | − | − | − |
| 63 | − | − | − | + | − | − | − |
| 67 | − | − | − | + | − | − | − |
| 68 | − | − | − | + | − | − | − |

TABLE 2-continued

Summary of kinase activity-comparison of reference compounds 263, 293 and 302
of WO2009/155551 with selected compounds of the present invention (overview of tables 6 and 7).

| | | | | | | | |
|---|---|---|---|---|---|---|---|
| 69 | − | − | − | − | − | − | − |
| 70 | − | − | + | − | − | − | − |
| 71 | − | − | − | − | − | − | − |
| 73 | − | + | + | − | − | + | − |

Explanation of "++", "+" and "−" in table 2:
"++" refers to >80% inhibition at 10 μmolar compound concentration;
"+" refers to 80-40% inhibition at 10 μmolar compound concentration;
"−" refers to <40% inhibition at 10 μmolar compound concentration.

The objective technical problem is thus to provide potent modulators of γ-secretase which are selective over ABL1, AURKA (Aurora A), CDK5/p35, CSF1R (FMS), FGFR1, FLT4 (VEGFR3), LYN B, MAP4K2 (GCK), PDGFRA (PDGFR alpha), PTK2 (FAK), RET, RPS6 KB1 (p70S6K), FGFR2, KDR (VEGFR2) or MAP4K4 (HGK).

According to the present invention, the compounds disclosed herein have surprisingly been found to be potent and selective modulators of γ-secretase.

Due to their potent modulation of γ-secretase and increased selectivity over ABL1, AURKA (Aurora A), CDK5/p35, CSF1R (FMS), FGFR1, FLT4 (VEGFR3), LYN B, MAP4K2 (GCK), PDGFRA (PDGFR alpha), PTK2 (FAK), RET, RPS6 KB1 (p7056K), FGFR2, KDR (VEGFR2) or MAP4K4 (HGK), compounds of the present invention are expected to be both efficacious in in vivo models and to have a sufficient window between efficacy and undesired effects such as renal toxicity, thrombocytopenia, neutropenia, stomatitis, diarrhoea or cardiovascular events. Consequently, compounds of the present invention must be more viable for human use.

The present invention provides novel triazolo pyridines of formula II

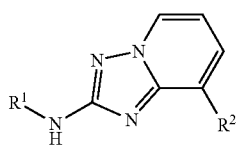

II in which
R$^1$ represents

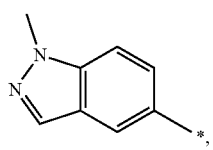

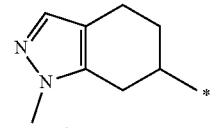

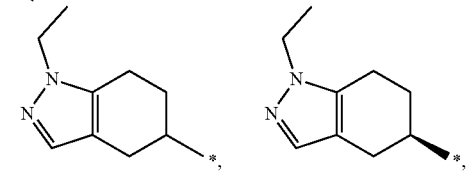

-continued

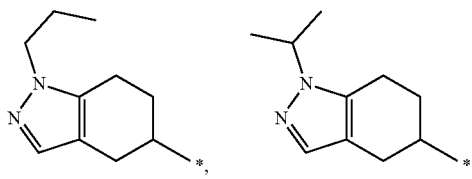

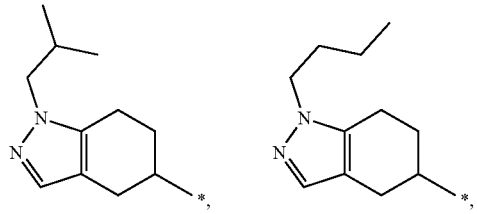

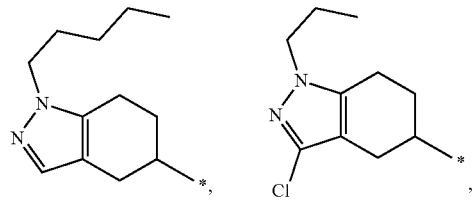

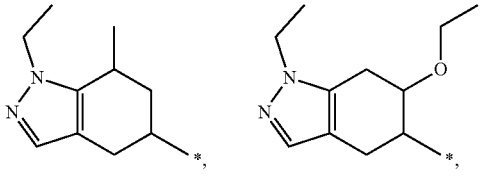

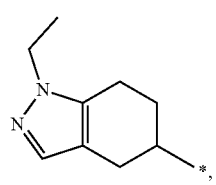

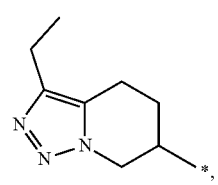

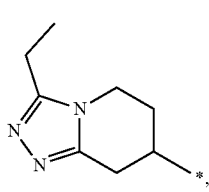

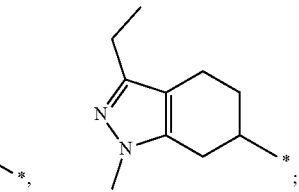

R² represents
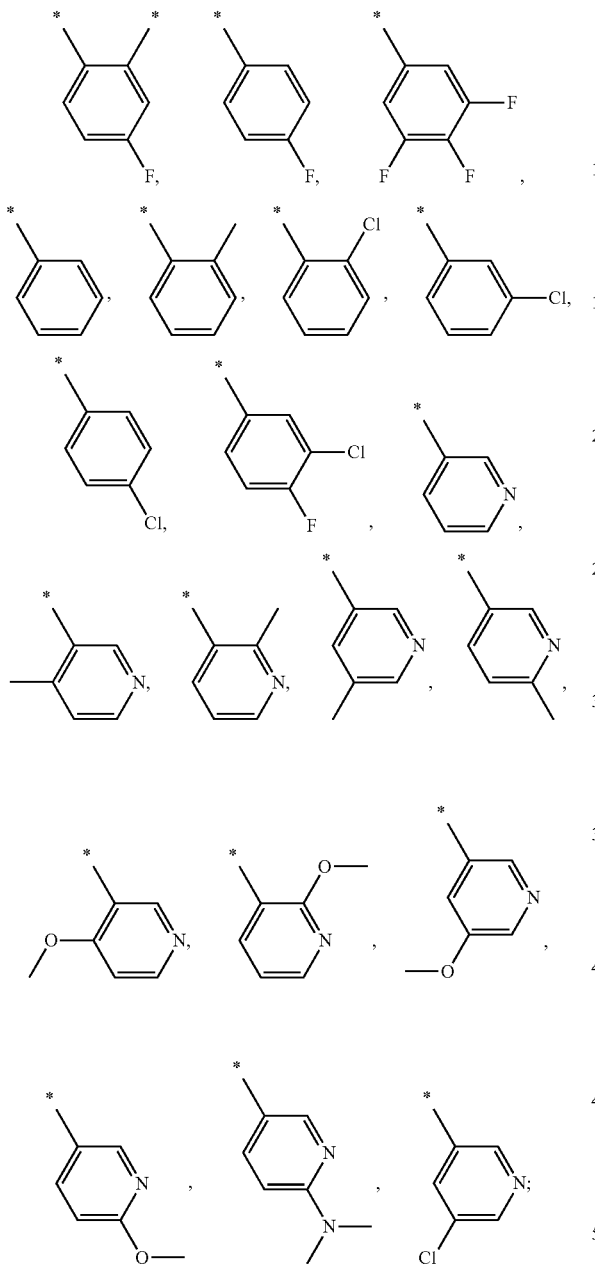
or a salt thereof, particularly a pharmaceutically acceptable salt thereof.
In another embodiment, the present invention provides novel triazolo pyridines of formula II
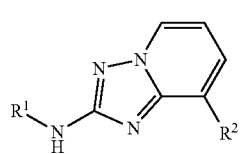
in which
R¹ represents
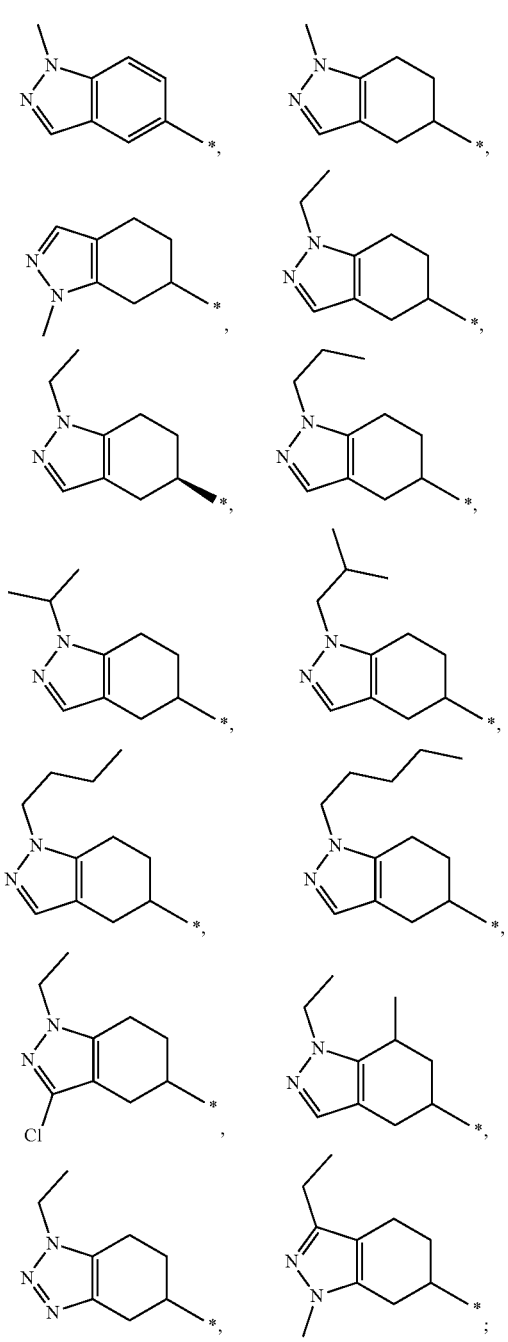
R² represents or a salt thereof, particularly a pharmaceutically acceptable salt thereof.
Further preferred are the following compounds:
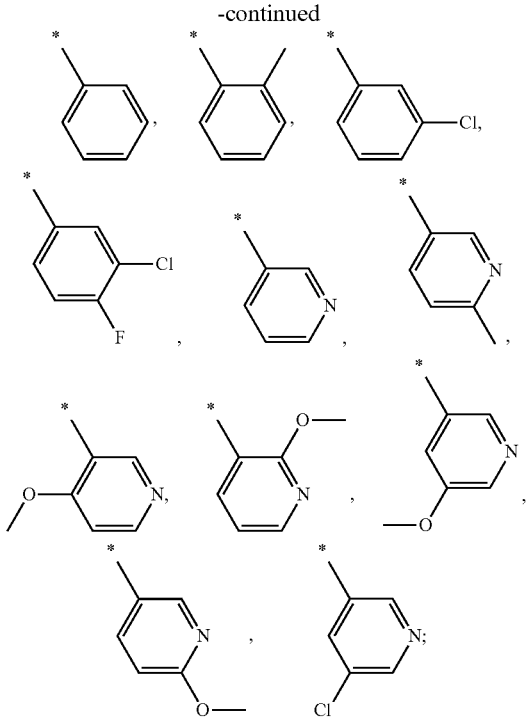

-continued
| Example no. | Structure |
|---|---|
| 45 | 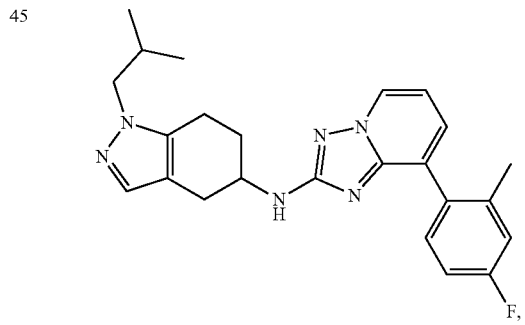 |
| 46 | 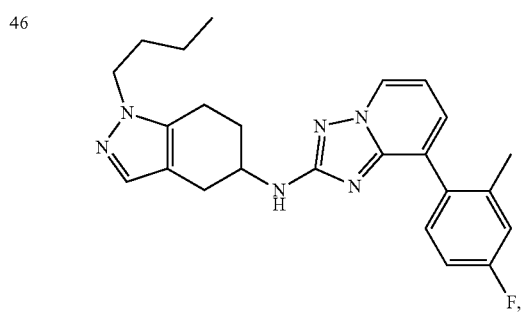 |
| 47 | 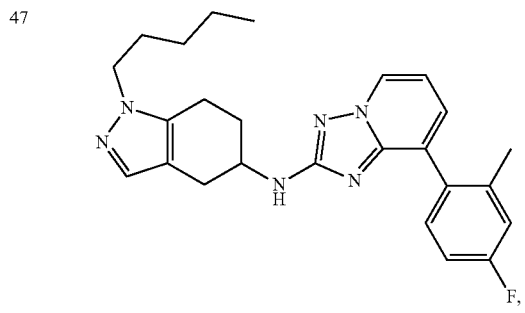 |
| 48 | 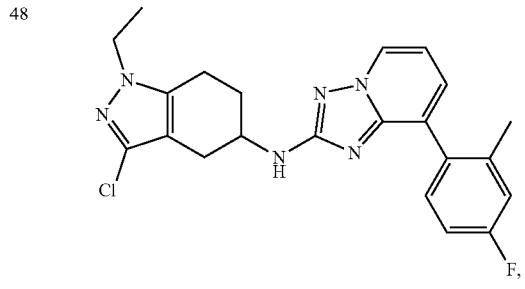 |
| 49 | 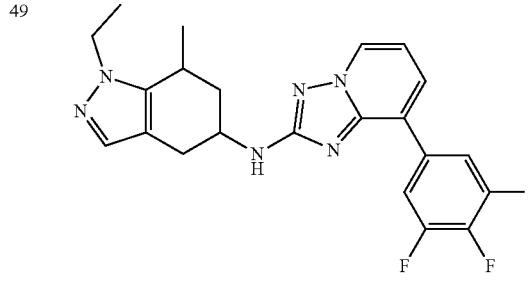 |
-continued
| Example no. | Structure |
|---|---|
| 50 | 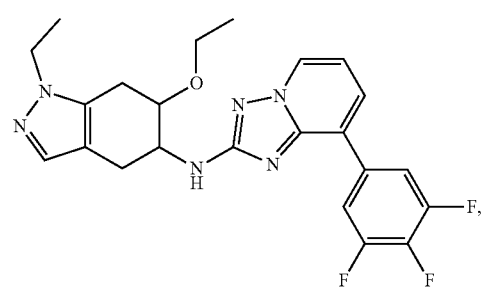 [SMILES: CCOC1Cc2c(cnn2CC)CC1Nc1nc2c(-c3cc(F)c(F)c(F)c3)cccn2n1] |
| 51 | 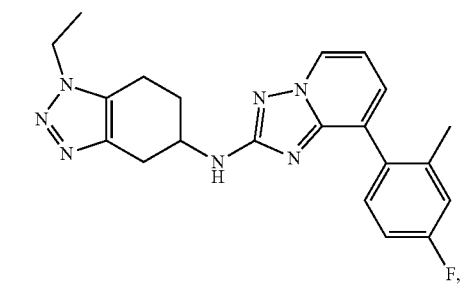 [SMILES: CCn1nnc2c1CCC(Nc1nc3c(-c4ccc(F)cc4C)cccn3n1)C2] |
| 52 | 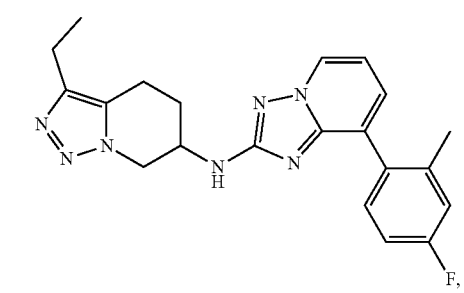 [SMILES: CCc1nnn2c1CCC(Nc1nc3c(-c4ccc(F)cc4C)cccn3n1)C2] |
| 53 | 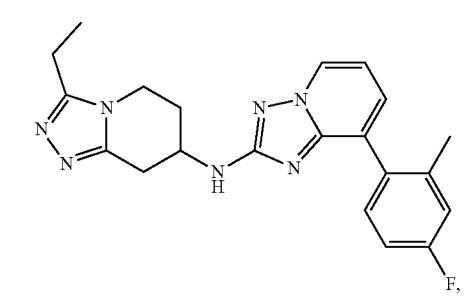 [SMILES: CCc1nnc2n1CCC(Nc1nc3c(-c4ccc(F)cc4C)cccn3n1)C2] |
| 54 | 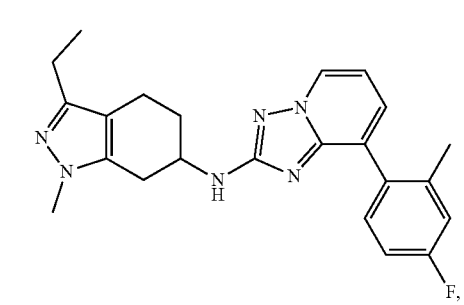 [SMILES: CCc1nn(C)c2c1CCC(Nc1nc3c(-c4ccc(F)cc4C)cccn3n1)C2] |

| Example no. | Structure |
|---|---|
| 55 | 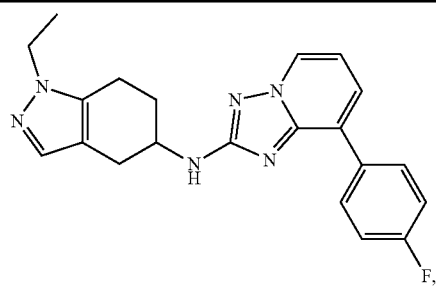 |
| 56 | 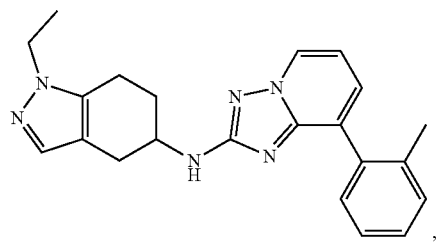 [SMILES: CCn1ncc2c1CCC(Nc1nc3c(-c4ccccc4C)cccn3n1)C2] |
| 57 | 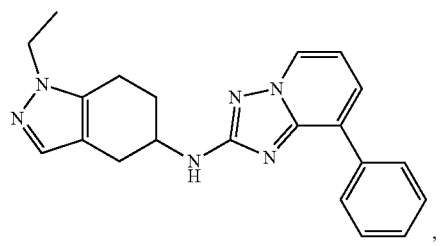 [SMILES: CCn1ncc2c1CCC(Nc1nc3c(-c4ccccc4)cccn3n1)C2] |
| 58 | 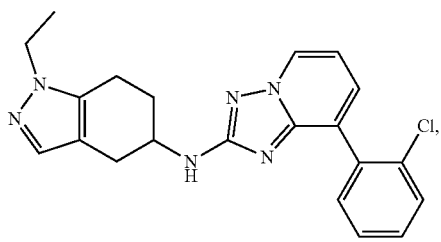 [SMILES: CCn1ncc2c1CCC(Nc1nc3c(-c4ccccc4Cl)cccn3n1)C2] |
| 59 | 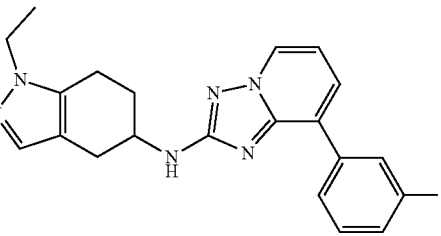 |
| 60 | 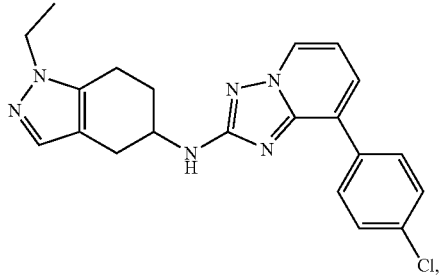 [SMILES: CCn1ncc2c1CCC(Nc1nc3c(-c4ccc(Cl)cc4)cccn3n1)C2] |
| Example no. | Structure |
|---|---|
| 61 | 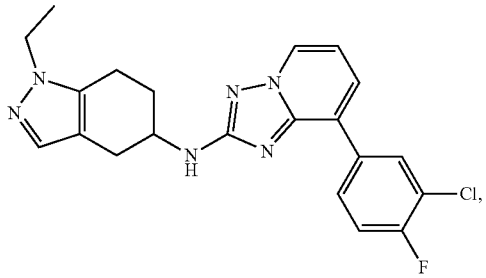 [SMILES: CCn1ncc2c1CCC(Nc1nc3c(-c4ccc(F)c(Cl)c4)cccn3n1)C2] |
| R-61 | 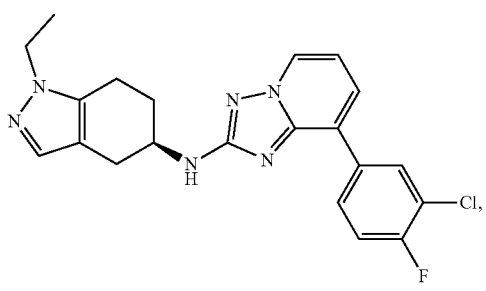 [SMILES: CCn1ncc2c1CC[C@@H](Nc1nc3c(-c4ccc(F)c(Cl)c4)cccn3n1)C2] |
| S-61 | 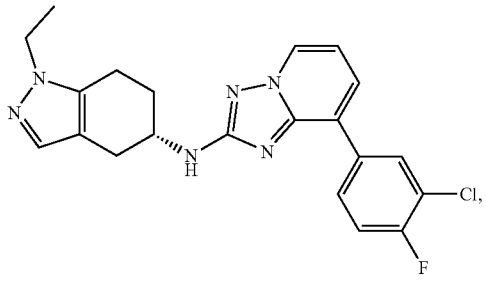 [SMILES: CCn1ncc2c1CC[C@H](Nc1nc3c(-c4ccc(F)c(Cl)c4)cccn3n1)C2] |
| 62 | 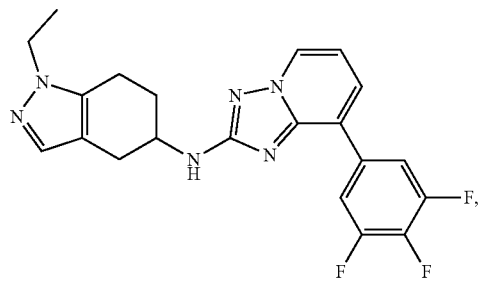 [SMILES: CCn1ncc2c1CCC(Nc1nc3c(-c4cc(F)c(F)c(F)c4)cccn3n1)C2] |
| 63 | 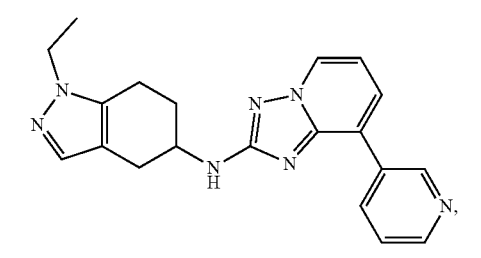 |

| Example no. | Structure |
|---|---|
| 64 | 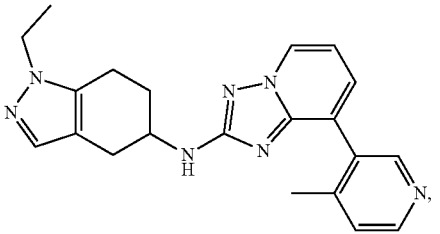 [SMILES: CCn1ncc2c1CCC(Nc1nc3c(-c4cnccc4C)cccn3n1)C2] |
| 65 | 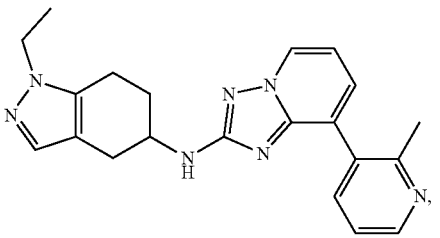 [SMILES: CCn1ncc2c1CCC(Nc1nc3c(-c4cccnc4C)cccn3n1)C2] |
| 66 | 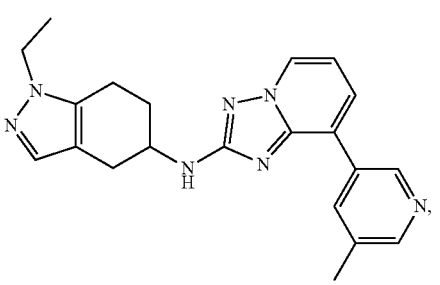 [SMILES: CCn1ncc2c1CCC(Nc1nc3c(-c4cncc(C)c4)cccn3n1)C2] |
| 67 | 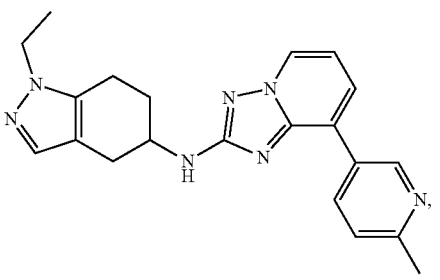 [SMILES: CCn1ncc2c1CCC(Nc1nc3c(-c4ccc(C)nc4)cccn3n1)C2] |
| 68 | 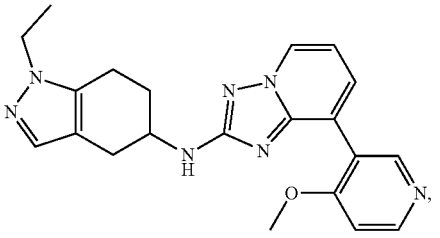 [SMILES: CCn1ncc2c1CCC(Nc1nc3c(-c4cnccc4OC)cccn3n1)C2] |
| 69 | 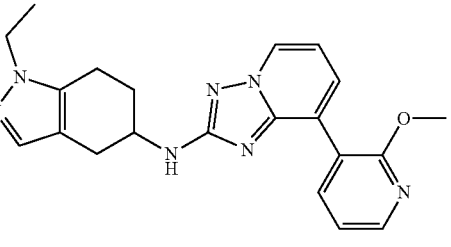 |
| 70 | 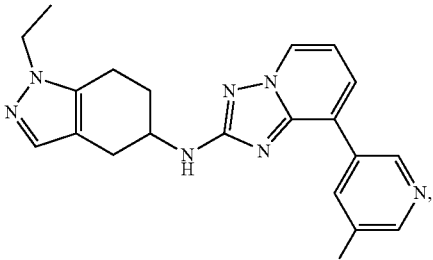 |
| 71 | 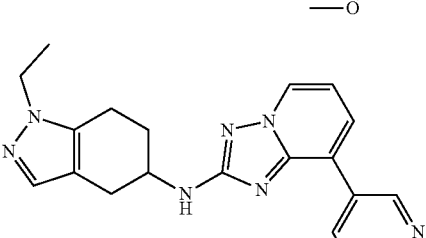 |
| 72 | 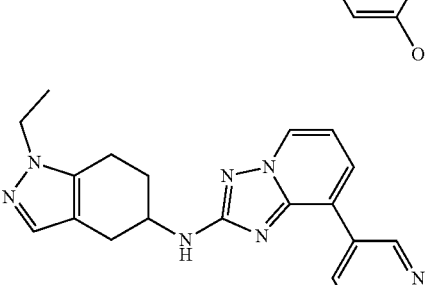 |
| 73 | 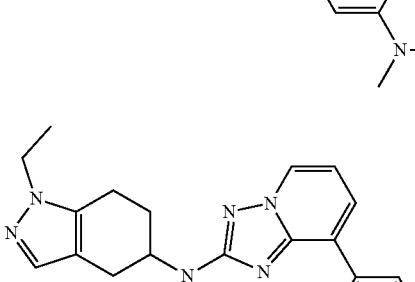 | or a pharmaceutically acceptable salt thereof.

BRIEF DESCRIPTION OF THE FIGURES

FIG. 1 shows the X-Ray structure of compound R-61

GENERAL DEFINITIONS

Terms not specifically defined herein should be given the meanings that would be given to them by one skilled in the art in light of the disclosure and the context.

In case a compound of the present invention is depicted in form of a chemical name as well as a formula, the formula shall prevail in case of any discrepancy.

An asterisk may be used in sub-formulas to indicate the bond which is connected to the core molecule or to the substituent to which it is bound as defined.

Stereochemistry:

Unless specifically indicated, throughout the specification and the appended claims, a given chemical formula or name shall encompass tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane. The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

EXPERIMENTAL PART

List of Abbreviations

DCM Dichloromethane
DIPEA Diisopropylamine
DMF Dimethylformamide
DMSO Dimethylsulfoxide
HCl Hydrochloric acid
HPLC High pressure liquid chromatography
MPLC Medium pressure liquid chromatography
$NH_3$ Ammonia
PE Petrol ether
psi Pounds per square inch
RT Room temperature
$R_t$ Retention time
TFA Trifluoro acetic acid
THF Tetrahydrofurane Analytical HPLC-Methods The following eluents were used: water containing 0.1% $NH_3$ (eluent A), acetonitrile (eluent B) and water containing 0.1% trifluoro acetic acid (eluent C). The mobile phase "water 0.1% TFA" is prepared by adding 1 mL of a commercially available TFA solution to 999 mL water.

Analogously, the mobile phase "water 0.1% $NH_3$" is prepared by adding 4 mL of a commercially available concentrated ammonium hydroxide solution (25 wt %) to 996 mL water.

Method 1: Agilent 1200 with DA- and MS-detector, Waters Xbridge C18, 3.0×30 mm, 2.5 μm, 60° C., gradient 0.00-0.20 min 97% eluent A in eluent B (flow 2.2 mL/min), 0.20-1.20 min 3% to 100% eluent B (flow 2.2 mL/min), 1.20-1.25 min 100% eluent B (flow 2.2 mL/min), 1.25-1.40 min 100% eluent B (flow 3.0 mL/min).

Method 2: Agilent 1200 with DA- and MS-detector, Sunfire C18, 3.0×30 mm, 2.5 μm, 60° C., gradient 0.00-0.20 min 97% eluent C in eluent B (flow 2.2 mL/min), 0.20-1.20 min 3% to 100% eluent B (flow 2.2 mL/min), 1.20-1.25 min 100% eluent B (flow 2.2 mL/min), 1.25-1.40 min 100% eluent B (flow 3.0 mL/min).

Method 3: Waters Acquity with DA- and MS-detector, Waters XBridge BEH C18, 2.1×30 mm, 1.7 μm, 60° C., gradient 0.00-0.20 min 95% eluent A in eluent B (flow 1.3 mL/min), 0.02-1.00 min 5% to 100% eluent B (flow 1.3 mL/min), 1.00-1.10 min 100% eluent B (flow 1.3 mL/min).

Method 4: Waters Alliance with DA- and MS-detector, Waters XBridge C18, 4.6×30 mm, 3.5 μm, 60° C., gradient 0.00-0.20 min 97% eluent A in eluent B (flow 5.0 mL/min), 0.20-1.60 min 3% to 100% eluent B (flow 5.0 mL/min), 1.60-1.70 min 100% eluent B (flow 5.0 mL/min).

Method 5: Waters Acquity with DA- and MS-detector, Sunfire C18, 2.1×30 mm, 2.5 μm, 60° C., gradient 0.00-0.02 min 99% eluent C in eluent B (flow 1.3 mL/min), 0.02-1.00 min 1% to 100% eluent B (flow 1.3 mL/min), 1.00-1.10 min 100% eluent B (flow 1.3 mL/min), 1.10-1.15 min 99% eluent C in eluent B (flow 1.3 mL/min), 1.15-2.00 min 99% eluent C in eluent B (flow 1.3 mL/min).

Method 6: Waters Acquity with DA- and MS-detector, Sunfire C18, 2.1×30 mm, 2.5 μm, 60° C., gradient 0.00-0.02 min 99% eluent C in eluent B (flow 1.5 mL/min), 0.02-1.00 min 1% to 100% eluent B (flow 1.5 mL/min), 1.00-1.10 min 100% eluent B (flow 1.5 mL/min).

Method 7: Waters Acquity with DA- and MS-detector, Waters XBridge BEH C18, 2.1×30 mm, 1.7 μm, 60° C., gradient 0.00-0.02 min 99% eluent C in eluent B (flow 1.6 mL/min), 0.02-1.00 min 1% to 100% eluent B (flow 1.6 mL/min), 1.00-1.10 min 100% eluent B (flow 1.6 mL/min).

Method 8: Waters Acquity with 3100 MS detector, Waters Xbridge C18, 3.0×30 mm, 2.5 μm, 60° C., gradient 0.00-1.30 min 97% eluent A in eluent B (flow 1.5 mL/min), 1.30-1.50 min 1% eluent A in eluent B (flow 1.5 mL/min), 1.50-1.60 min 0.1% to 95% eluent A in eluent B (flow 1.5 mL/min).

Method 9: Agilent 1100 with DA- and MS-detector, Sunfire C18, 3.0×30 mm, 2.5 μm, 60° C., gradient 0.00-1.20 min 98% eluent C in eluent B (flow 2.0 mL/min), 1.20-1.40 min 2% to 100% eluent B (flow 2.0 mL/min).

Method 10: Agilent 1100 with DAD, CTC Autosampler and Waters MS-Detector, Waters Sunfire C18, 3.0×30 mm, 3.5 μm, 60° C., gradient 0.00-0.30 min 98% eluent C in eluent B (flow 2.0 mL/min), 0.30-1.50 min 2% to 100% eluent B (flow 2.0 mL/min), 1.50-1.60 min 100% eluent B (flow (2.0 mL/min).

Method 11: Waters Acquity with DA- and MS-Detector, Waters Sunfire C18, 3.0×30 mm, 2.5 µm, 60° C., gradient 0.00-1.30 min 95% eluent C in eluent B (flow 1.5 mL/min), 1.30-1.50 min 5% to 100% eluent B (flow 1.5 mL/min).

Method 12: Waters Acquity with DA- and MS-Detector, Waters XBridge C18, 3.0×30 mm, 2.5 µm, 60° C., gradient 0.00-1.20 min 95% eluent A in eluent B (flow 1.5 mL/min), 1.20-1.40 min 5% to 100% eluent B (flow 1.5 mL/min), 1.40-1.45 min 98% A in eluent B (flow 1.5 mL/min).

Method 13: Agilent 1260 SFC with DAD and ELSD, Daicel Chiralpak® AY-H, 4.6×250 mm, 5 µm, 40° C., mobile phase: eluent A: supercritical $CO_2$, eluent B: ethanol containing 20 mM ammonia, 0.00-10.00 min, gradient A:B 85:15, flow rate 4 mL/min, system back pressure 2175 psi.

Method 14: Agilent 1260 SFC with DAD and ELSD, Daicel Chiralpak® IF, 4.6×250 mm, 5 µm, 40° C., mobile phase: eluent A: supercritical $CO_2$, eluent B: ethanol containing 20 mM ammonia, 0.00-10.00 min, gradient A:B 60:40, flow rate 4 mL/min, system back pressure 2175 psi.

Method 15: Agilent 1260 SFC with DA- and MS-Detector, Daicel Chiralpak® IA, 4.6×250 mm, 5 µm, 40° C., mobile phase: eluent A: supercritical $CO_2$, eluent B: ethanol containing 20 mM ammonia, 0.00-10.00 min, gradient A:B 75:25, flow rate 4 mL/min, system back pressure 2175 psi.

General Analytics.

All reactions were carried out using commercial grade reagents and solvents. NMR spectra were recorded on a Bruker AVANCE IIIHD 400 MHz instrument using TopSpin 3.2 pl6 software. Chemical shifts are given in parts per million (ppm) downfield from internal reference trimethylsilane in δ units. Selected data are reported in the following manner: chemical shift, multiplicity, coupling constants (J), integration. Analytical thin-layer chromatography (TLC) was carried out using Merck silica gel 60 F254 plates. All compounds were visualized as single spots using short wave UV light. Low resolution mass spectra were obtained using a liquid chromatography mass spectrometer (LCMS) that consisted of an Agilent 1100 series LC coupled to a Agilent 6130 quadrupole mass spectrometer (electrospray positive ionization). High resolution masses were determined on a Waters QTOF G2-Si spectrometer. Unless otherwise specified the purity of all intermediates and final compounds was determined to be >95% by LCMS using one of the methods (1-12), which are described in detail in the Supporting information. Enantiomeric purity was determined by supercritical fluid chromatography on Agilent 1260 SFC with DA- and ELS detection using one of the methods (13-15), which are described in detail in the Supporting information. Optical rotation was determined by a Perkin Elmer 343 polarimeter. Specific rotations $[\alpha]_D^{20}$ are given in deg cm³ g$^{-1}$ dm$^{-1}$.

Synthesis Procedures

General procedure A: preparation of intermediates 12a-c and 12e-g. A mixture of the respective nitro indazole 11a-d (1.0 equiv), alkyl halide (1.0 equiv) and $K_2CO_3$ (2 equiv) in DMF was stirred for 3 h at 60° C. After cooling to RT the reaction mixture was poured into water and extracted 3× with ethyl acetate. The combined organic phases were dried and concentrated under reduced pressure. The crude residue was purified by preparative reverse-phase HPLC.

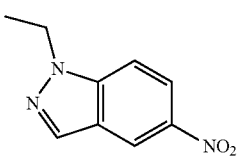

1-Ethyl-5-nitro-1H-indazole (12a). Prepared according to general procedure A using nitro indazole 11a and ethyl iodide. Ratio of 12a vs. regioisomeric 2-ethyl-5-nitro-2H-indazole (HPLC analysis, method 1): 2:1.

12a precipitated during work-up and was collected by filtration. Yield: 332 mg (57%). LCMS (ESI$^+$) calculated for $C_9H_8N_3O_2$ [M+H]$^+$ m/z 192.0773, found 192.2. $^1$H NMR (400 MHz, (CD$_3$)$_2$SO) δ 8.83 (d, J=2.2 Hz, 1H), 8.40 (s, 1H), 8.22 (dd, J=9.3, 2.2 Hz, 1H), 4.53 (q, J=7.3 Hz, 2H), 1.43 (t, J=7.3 Hz, 3H). HPLC (Method 1): R$_t$=0.89 min.

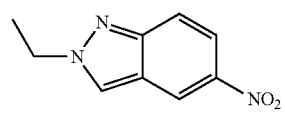

2-Ethyl-5-nitro-2H-indazole. Regioisomeric byproduct 2-ethyl-5-nitro-2H-indazole was isolated by preparative HPLC from the remaining mother liquor. Yield: 193 mg (33%). LCMS (ESI$^+$) calculated for $C_9H_8N_3O_2$ [M+H]$^+$ m/z 192.0773, found 192.2. $^1$H NMR (400 MHz, (CD$_3$)$_2$SO) δ 8.87 (d, J=2.2 Hz, 1H), 8.82 (s, 1H), 8.01 (dd, J=9.4, 2.3 Hz, 1H), 7.78 (d, J=9.4 Hz, 1H), 4.54 (q, J=7.3 Hz, 2H), 1.54 (t, J=7.3 Hz, 3H).

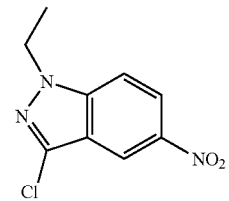

3-Chloro-1-ethyl-5-nitro-1H-indazole (12b). Prepared according to general procedure A using nitro indazole 11b and ethyl iodide. Ratio of 12b vs. regioisomeric 3-chloro-2-ethyl-5-nitro-2H-indazole (HPLC analysis, method 11): 87:13.

12b. Yield: 5.68 g (83%). LCMS (ESI$^+$) calculated for $C_9H_8ClN_3O_2$ [M+H]$^+$ m/z 226.0383, found 226.1. $^1$H NMR (400 MHz, (CD$_3$)$_2$SO) δ 8.60 (dd, J=2.2, 0.5 Hz), 8.31 (dd, J=9.3, 2.2 Hz, 1H), 8.00 (dd, J=9.3, 0.5 Hz, 1H), 4.51 (q, J=7.2 Hz, 2H), 1.43 (t, J=7.2 Hz, 3H). HPLC (Method 1): R$_t$=0.95 min.

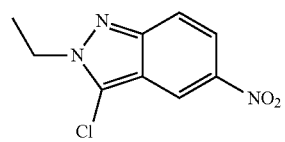

3-Chloro-2-ethyl-5-nitro-2H-indazole. Yield: 0.78 g (11%). LCMS (ESI$^+$) calculated for $C_9H_8ClN_3O_2$ [M+H]$^+$ m/z 226.0383, found 226.1. $^1$H NMR (400 MHz, (CD$_3$)$_2$SO)

δ 8.65 (dd, J=2.3, 0.6 Hz, 1H), 8.07 (dd, J=9.5, 2.2 Hz, 1H), 7.85 (dd, J=9.5, 0.6 Hz, 1H), 4.55 (q, J=7.3 Hz, 2H), 1.51 (t, J=7.3 Hz, 3H). HPLC (Method 1): R$_t$=0.87 min.

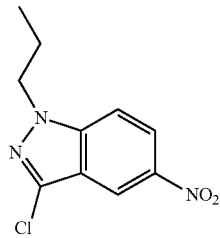 [SMILES: CCCn1nc(Cl)c2cc([N+](=O)[O-])ccc21]

3-Chloro-1-propyl-5-nitro-1H-indazole (12c). Prepared according to general procedure A using nitro indazole 11b and n-propyl iodide. Ratio of 12c vs. regioisomeric 3-chloro-2-n-propyl-5-nitro-2H-indazole (HPLC analysis, method 2): 88:12.

12c. Yield: 960 mg (79%). LCMS (ESI$^+$) calculated for C$_{10}$H$_{10}$ClN$_3$O$_2$ [M+H]$^+$ m/z 240.0540, found 240.1. $^1$H NMR (400 MHz, (CD$_3$)$_2$SO) δ 8.60 (d, J=2.2 Hz, 1H), 8.31 (dd, J=9.4, 2.2 Hz, 1H), 8.01 (d, J=9.4 Hz, 1H), 4.45 (t, J=6.9 Hz, 2H), 1.86 (m, 2H), 0.84 (t, J=7.3 Hz, 3H). HPLC (Method 2): R$_t$=1.15 min.

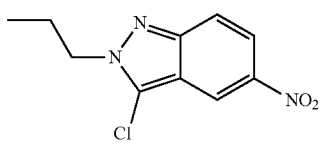 [SMILES: CCCn1nc2ccc([N+](=O)[O-])cc2c1Cl]

3-Chloro-2-n-propyl-5-nitro-2H-indazole. This minor regioisomer was not isolated. HPLC (Method 2): R$_t$=1.10 min.

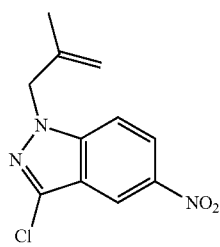 [SMILES: C=C(C)Cn1nc(Cl)c2cc([N+](=O)[O-])ccc21]

3-Chloro-1-(2-methyl-allyl)-5-nitro-1H-indazole (12e). Prepared according to general procedure A using nitro indazole 11b and 3-bromo-2-methyl propene. Ratio of 12e vs. regioisomeric 3-chloro-2-(2-methyl-allyl)-5-nitro-2H-indazole (HPLC analysis, method 1): 92:8. 12e. Yield: 1.14 g (90%). LCMS (ESI$^+$) calculated for C$_{11}$H$_{10}$ClN$_3$O$_2$ [M+H]$^+$ m/z 252.0540, found 252.0. $^1$H NMR (400 MHz, (CD$_3$)$_2$SO) δ 8.61 (d, J=2.0 Hz, 1H), 8.32 (dd, J=9.3, 2.0 Hz, 1H), 7.95 (d, J=9.3 Hz, 1H), 5.10 (s, 2H), 4.93 (s, 1H), 4.71 (s, 1H), 1.63 (s, 3H). HPLC (Method 1): R$_t$=1.09 min.

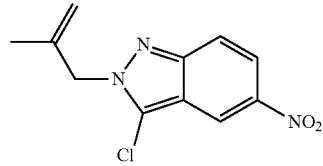 [SMILES: C=C(C)Cn1nc2ccc([N+](=O)[O-])cc2c1Cl]

3-Chloro-2-(2-methyl-allyl)-5-nitro-2H-indazole. This minor regioisomer was not isolated. HPLC (Method 1): R$_t$=1.04 min.

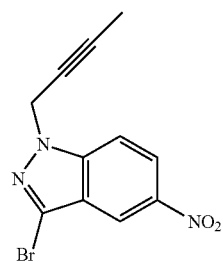

12f

3-Bromo-1-but-2-ynyl-5-nitro-1H-indazole (12f). Prepared according to general procedure A using nitro indazole 11c and 1-bromo-2-butyne. Only one regioisomer was observed. Yield: 1.17 g (96%). LCMS (ESI$^+$) calculated for C$_{11}$H$_9$BrN$_3$O$_2$ [M+H]$^+$ m/z 293.9878, found 294.0. $^1$H NMR (400 MHz, (CD$_3$)$_2$SO) δ 8.50 (dd, J=2.1, 0.4 Hz, 1H), 8.37 (dd, J=9.3, 2.2 Hz, 1H), 8.02 (dd, J=9.3, 0.4 Hz, 1H), 5.40 (q, J=2.4 Hz, 2H), 1.80 (t, J=2.4 Hz, 3H). HPLC (Method 11): R$_t$=0.97 min.

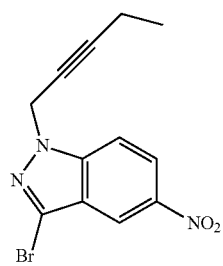

12g

3-Bromo-1-pent-2-ynyl-5-nitro-1H-indazole (12 g). Prepared according to general procedure A using nitro indazole 11c and 1-bromo-2-pentyne. Only one regioisomer was observed. Yield: 1.18 g (93%). LCMS (ESI$^+$) calculated for C$_{11}$H$_9$BrN$_3$O$_2$ [M+H]$^+$ m/z 308.0035, found 308.0. $^1$H NMR (400 MHz, (CD$_3$)$_2$SO) δ 8.50 (d, J=2.0 Hz, 1H), 8.37 (dd, J=9.3, 2.1 Hz, 1H), 8.02 (d, J=9.3 Hz, 1H), 5.42 (t, J=2.2 Hz, 2H), 2.15-2.23 (m, 2H), 1.03 (t, J=7.5 Hz, 3H). HPLC (Method 11): R$_t$=1.04 min.

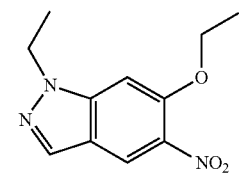 [SMILES: CCOc1cc2c(cnn2CC)cc1[N+](=O)[O-]]

6-Ethoxy-1-ethyl-5-nitro-1H-indazole (12 h). Prepared according to general procedure A using nitro indazole 11d and ethyl iodide. Ratio of 12 h vs. regioisomeric 6-ethoxy-2-ethyl-5-nitro-2H-indazole (HPLC analysis, method 3): 1.7:1.

12 h. Yield: 255 mg (56%). LCMS (ESI$^+$) calculated for $C_{11}H_{13}N_3O_3$ [M+H]$^+$ m/z 236.1035, found 236.1. $^1$H NMR (400 MHz, (CD$_3$)$_2$SO) δ 8.37 (s, 1H), 8.16 (s, 1H), 7.46 (s, 1H), 4.44 (q, J=7.2 Hz, 2H), 4.27 (q, J=7.1 Hz, 2H), 1.39 (t, J=7.2 Hz, 3H), 1.39 (t, J=7.1 Hz, 3H). HPLC (Method 3): R$_t$=0.55 min.

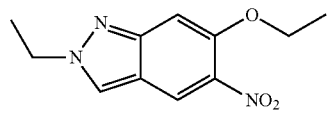 [SMILES: CCOc1cc2nn(CC)cc2cc1[N+](=O)[O-]]

6-Ethoxy-2-ethyl-5-nitro-2H-indazole. Yield: 126 mg (28%). LCMS (ESI$^+$) calculated for $C_{11}H_{13}N_3O_3$ [M+H]$^+$ m/z 236.1035, found 236.1. $^1$H NMR (400 MHz, (CD$_3$)$_2$SO) δ 8.57 (s, 1H), 8.36 (s, 1H), 7.24 (s, 1H), 4.45 (q, J=7.3 Hz, 2H), 4.18 (q, J=7.0 Hz, 2H), 1.50 (t, J=7.3 Hz, 3H), 1.35 (t, J=7.0 Hz, 3H). HPLC (Method 3): R$_t$=0.50 min.

General procedure B: preparation of intermediates 13a-h. To a solution of the respective nitro/amino indazole 12a-h (1.0 equiv) in MeOH was added Nishimura's catalyst (Nishimura's catalyst was purchased from Umicore AG & Co. KG, 63457 Hanau-Wolfgang, Germany, product no. 68 2562 1666, CAS no. 39373-27-8). The mixture was hydrogenated (4 bar hydrogen atmosphere) for 6-53 h at RT, filtered and concentrated under reduced pressure. The crude product was purified by preparative reverse-phase HPLC.

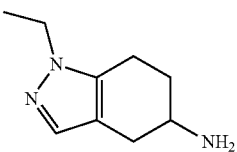

1-Ethyl-4,5,6,7-tetrahydro-1H-indazol-5-ylamine (13a). Prepared according to general procedure B from nitro indazole 12b (reaction time 11 h). To achieve complete dehalogenation the catalyst was switched to palladium on charcoal (additional reaction time 1 h at 4 bar hydrogen atmosphere and RT). Yield: 2.85 g (69%). LCMS (ESI$^+$) calculated for $C_9H_{15}N_3$ [M+H]$^+$ m/z 166.1344, found 166.1. $^1$H NMR (400 MHz, (CD$_3$)$_2$SO) δ 7.08 (s, 1H), 3.93 (q, J=7.3 Hz, 2H), 2.90-2.98 (m, 1H), 2.50-2.71 (m, 3H), 2.05-2.12 (m, 1H), 1.82-1.90 (m, 1H), 1.54 (br s, 2H), 1.44-1.55 (m, 1H), 1.25 (t, J=7.3 Hz, 3H). Note: NH$_2$ protons not visible. HPLC (Method 4): R$_t$=0.64 min.

Preparative chiral separation: Racemic amine 13a (27 g, 163 mmol) was submitted to preparative chiral SFC separation (Thar SFC-80, Chiralpak AD-H, 25×3 cm, 5 μm, mobile phase: eluent A: supercritical CO$_2$, eluent B: isopropanol containing 0.1% conc aq ammonia, gradient A:B 75:25, flow rate 65 g/min, wavelength 220 nm, system back pressure 100 bar). R-13a: R$_t$=2.19 min. S-13a: R$_t$=2.84 min.

R-13a: Yield: 9.21 g (34%). Enantiomeric purity (method 13): 98.7% ee. The (R)-configuration of the sterogenic center has been assigned via the X-Ray structure of compound R-61.

S-13a: Yield: 8.37 g (31%). Enantiomeric purity (method 13): 97.8% ee.

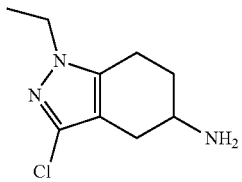

3-Chloro-1-ethyl-4,5,6,7-tetrahydro-1H-indazol-5-ylamine (13b). Prepared according to general procedure B from nitro indazole 12b (reaction time 24 h). Yield: 140 mg (18%). LCMS (ESI$^+$) calculated for $C_9H_{14}ClN_3$ [M+H]$^+$ m/z 200.0955, found 200.1. $^1$H NMR (400 MHz, (CD$_3$)$_2$SO) δ 3.92 (q, J=7.2 Hz, 2H), 2.95-3.03 (m, 1H), 2.64-2.74 (m, 1H), 2.50-2.58 (m, 2H), 1.96-2.04 (m, 1H), 1.80-1.88 (m, 1H), 1.45-1.57 (m, 1H), 1.26 (t, J=7.2 Hz, 3H). Note: NH$_2$ signals not visible. HPLC (Method 1): R$_t$=0.74 min.

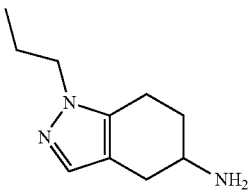

1-Propyl-4,5,6,7-tetrahydro-1H-indazol-5-ylamine (13c). Prepared according to general procedure B from nitro indazole 12c (reaction time 7 h). Yield: 250 mg (35%). LCMS (ESI$^+$) calculated for $C_{10}H_{17}N_3$ [M+H]$^+$ m/z 180.1501, found 180.2. $^1$H NMR (400 MHz, (CD$_3$)$_2$SO) δ 7.09 (s, 1H), 3.85 (t, J=7.2 Hz, 2H), 2.90-2.98 (m, 1H), 2.50-2.70 (m, 3H), 2.05-2.12 (m, 1H), 1.82-1.90 (m, 1H), 1.69 (m, 2H), 1.66 (br s, 2H), 1.44-1.54 (m, 1H), 0.81 (t, J=7.4 Hz, 3H). HPLC (Method 1): R$_t$=0.74 min.

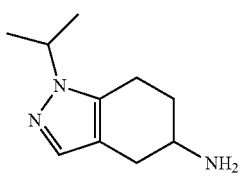

1-Isopropyl-4,5,6,7-tetrahydro-1H-indazol-5-ylamine (13d). Prepared according to general procedure B from amino indazole 12d (reaction time 6 h). Yield: 540 mg (56%). LCMS (ESI$^+$) calculated for $C_{10}H_{17}N_3$ [M+H]$^+$ m/z 180.1501, found 180.3. $^1$H NMR (400 MHz, (CD$_3$)$_2$SO) δ 7.10 (s, 1H), 4.33 (sept, J=6.6 Hz, 1H), 2.90-2.98 (m, 1H), 2.51-2.73 (m, 3H), 2.04-2.12 (m, 1H), 1.82-1.91 (m, 1H), 1.44-1.55 (m, 1H), 1.33 (d, J=6.6 Hz, 3H), 1.30 (d, J=6.6 Hz, 3H). Note: NH$_2$ signals not visible. HPLC (Method 1): R$_t$=0.70 min.

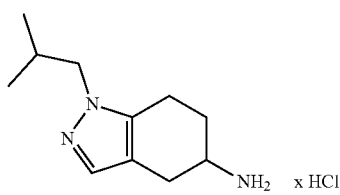

1-Isobutyl-4,5,6,7-tetrahydro-1H-indazol-5-ylamine (13e). Prepared according to general procedure B from nitro indazole 12e (reaction time 4 h). However, to achieve complete dehalogenation the catalyst was switched to palladium on charcoal (additional reaction time 16 h at 4 bar hydrogen atmosphere and RT). Yield: 1.07 g, HCl salt (quant.). LCMS (ESI$^+$) calculated for $C_{11}H_{19}N_3$ [M+H]$^+$ m/z 194.1657, found 194.3. $^1$H NMR (400 MHz, (CD$_3$)$_2$SO) δ 8.08 (br s, 3H, NH$_3$'), 7.22 (s, 1H), 3.73 (d, J=7.3 Hz, 2H), 3.29-3.40 (m, 1H, partially obscured by water signal), 2.82-2.90 (m, 1H), 2.72-2.80 (m, 1H), 2.56-2.69 (m, 1H), 2.43-2.51 (m, 1H, partially obscured by DMSO signal), 2.08-2.16 (m, 1H), 2.06 (m, 1H), 1.74-1.86 (m, 1H), 0.833 (d, J=6.6 Hz, 3H), 0.831 (d, J=6.6 Hz, 3H). HPLC (Method 1): R$_t$=0.77 min.

13f

1-Butyl-4,5,6,7-tetrahydro-1H-indazol-5-ylamine (13f). Prepared according to general procedure B from nitro indazole 12f (reaction time 45 min). To achieve complete dehalogenation the catalyst was switched to palladium on charcoal (additional reaction time 1 h at 4 bar hydrogen atmosphere and 50° C.). Yield: 505 mg, (66%). LCMS (ESI$^+$) calculated for $C_{11}H_{19}N_3$ [M+H]$^+$ m/z 194.1657, found 194.2. $^1$H NMR (400 MHz, (CD$_3$)$_2$SO) δ 7.09 (s, 1H), 3.89 (t, J=7.1 Hz, 2H), 2.89-2.98 (m, 1H), 2.57-2.71 (m, 2H), 2.45-2.56 (m, 1H), 2.04-2.13 (m, 1H), 1.82-1.90 (m, 1H), 1.60-1.70 (m, 2H), 1.44-1.55 (m, 1H), 1.18-1.29 (m, 2H), 0.87 (t, J=7.4 Hz, 3H). Note: NH$_2$ signals not visible. HPLC (Method 4): R$_t$=0.76 min.

13g

1-Pentyl-4,5,6,7-tetrahydro-1H-indazol-5-ylamine (13 g). Prepared according to general procedure B from nitro indazole 12 g (reaction time 4 h). Yield: 465 mg, (59%). LCMS (ESI$^+$) calculated for $C_{12}H_{21}N_3$ [M+H]$^+$ m/z 208.1814, found 208.0. $^1$H NMR (400 MHz, (CD$_3$)$_2$SO) δ 7.09 (s, 1H), 3.88 (t, J=7.1 Hz, 2H), 2.89-2.98 (m, 1H), 2.57-2.70 (m, 2H), 2.45-2.56 (m, 1H, mainly obscured by DMSO signal), 2.04-2.13 (m, 1H), 1.81-1.90 (m, 1H), 1.61-1.71 (m, 2H), 1.43-1.55 (m, 1H), 1.15-1.33 (m, 4H), 0.85 (t, J=7.1 Hz, 3H). Note: NH$_2$ signals not visible. HPLC (Method 3): R$_t$=0.46 min.

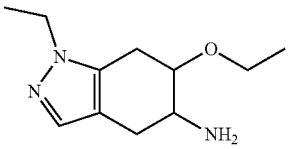

6-Ethoxy-1-Ethyl-4,5,6,7-tetrahydro-1H-indazol-5-ylamine (13 h). Prepared according to general procedure B from nitro indazole 12 h (reaction time 24 h). Yield: 31 mg (11%). LCMS (ESI$^+$) calculated for $C_{11}H_{19}N_3O$ [M+H]$^+$ m/z 210.1606, found 210.2. $^1$H NMR (400 MHz, (CD$_3$)$_2$SO) δ 7.01 (s, 1H), 3.95 (q, J=7.3 Hz, 2H), 3.62-3.67 (m, 1H), 3.45-3.62 (m, 2H), 3.06-3.11 (m, 1H), 2.67-2.79 (m, 2H), 2.48-2.56 (m, 1H, partially obscured by DMSO signal), 2.27-2.35 (m, 1H), 1.44 (broad s, 2H), 1.26 (t, J=7.3 Hz, 3H), 1.12 (t, J=7.0 Hz, 3H). HPLC (Method 3): R$_t$=0.33 min.

15

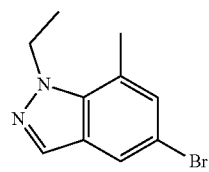

5-Bromo-1-ethyl-7-methyl-1H-indazole (15). To a mixture of 5-bromo-7-methyl-1H-indazole 14 (2.4 g, 10.9 mmol) in DMF (25 mL) was added sodium hydride (525.0 mg, 55% in mineral oil, 12.0 mmol) at 0°-5° C. After stirring for 20 min ethyl iodide (874.8 μL, 10.9 mmol) was added. After stirring for 30 min, the reaction mixture was poured into water and extracted 3× with ethyl acetate. The combined organic phases were dried over Na$_2$SO$_4$ and concentrated under reduced pressure. The remainder was purified by preparative reverse-phase HPLC to give 15. Yield: 800 mg (31%). LCMS (ESI$^+$) calculated for $C_{10}H_{11}BrN_2$ [M+H]$^+$ m/z 239.01839, found 239.0. $^1$H NMR (400 MHz, (CD$_3$)$_2$SO) δ 8.00 (s, 1H), 7.80 (m, 1H), 7.28 (m, 1H), 4.58 (q, J=7.2 Hz, 2H), 2.70 (s, 3H), 1.37 (t, J=7.2 Hz, 3H). HPLC (Method 4): R$_t$=1.23 min.

16

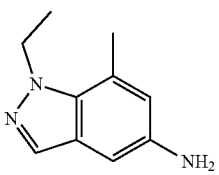

1-Ethyl-7-methyl-1H-indazol-5-ylamine (16). To a mixture of bromo indazole 15 (800.0 mg, 3.3 mmol), benzophenone imine (673.7 μL, 4.0 mmol) and sodium tert.-butoxide (643.1 mg, 6.7 mmol) in toluene (15 mL) under an atmosphere of argon was added Xantphos (38.7 mg, 67

μmol) and tris(dibenzylidene acetone)palladium(0) (61.3 mg, 67 μmol). The reaction mixture was stirred for 1 d at 130° C. After cooling to RT, TFA was added to acidify the reaction mixture. Stirring was continued for 1 h, then water was added and the organic phase was separated. The aqueous phase was subsequently made alkaline and extracted 3× with ethyl acetate. The combined organic phases were dried over Na$_2$SO$_4$, filtered and concentrated under reduced pressure. The remainder was purified by preparative reverse-phase HPLC to obtain 16. Yield: 374 mg, TFA salt (39%). LCMS (ESI$^+$) calculated for C$_{10}$H$_{13}$N$_3$ [M+H]$^+$ m/z 176.1188, found 176.1. $^1$H NMR (400 MHz, (CD$_3$)$_2$SO) δ 7.65 (s, 1H), 6.55 (m, 2H), 4.66 (br s, 2H), 4.46 (q, J=7.1 Hz, 2H), 2.57 (s, 3H), 1.31 (t, J=7.1 Hz, 3H). Note: $^1$H NMR spectrum was obtained from a sample of the free base. HPLC (Method 5): R$_t$=0.30 min.

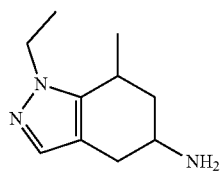

17

1-Ethyl-7-methyl-4,5,6,7-tetrahydro-1H-indazol-5-ylamine (17). To a mixture of amino indazole 16 (obtained as TFA salt, 374 mg, 1.3 mmol) in methanol (15 mL) was added PL-HCO$_3$ MP ion exchanger resin (1.96 mmol/g loading, 150-300 μm particle size) until pH was alkaline. The mixture was filtered and concentrated under reduce pressure to give 16 as free base, which was directly hydrogenated according to general procedure B (reaction time 2 d) to give 17. Yield: 230 mg (94%). LCMS (ESI$^+$) calculated for C$_{10}$H$_{17}$N$_3$ [M+H]$^+$ m/z 180.1501, found 180.1. $^1$H NMR (400 MHz, (CD$_3$)$_2$SO) δ 7.09 (s, 1H), 4.02 (q, J=7.2 Hz, 1H), 4.01 (q, J=7.2 Hz, 1H), 2.86-2.97 (m, 1H), 2.75-2.84 (m, 1H), 2.53-2.60 (m, 1H), 1.96-2.04 (m, 2H), 1.15-1.23 (m, 1H), 1.29 (t, J=7.2 Hz, 3H), 1.24 (d, J=6.6 Hz, 3H). Notes: NH$_2$ signals not visible. Only the major cis diastereomer was interpreted. HPLC (Method 4): R$_t$=0.67 min.

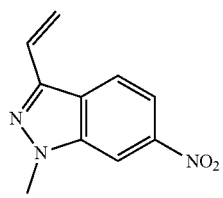

19

1-Methyl-6-nitro-3-vinyl-1H-indazole (19). A mixture of 3-bromo-1-methyl-6-nitro-1H-indazole 18 (100.0 mg, 391 μmol), vinylboronic acid pinacol ester (72.9 μL, 430 μmol), sodium carbonate solution (2N in water, 0.39 mL, 781 μmol) and bis(triphenylphosphine)palladium(II) chloride (8.2 mg, 12 μmol) in a mixture of 1,4-dioxane/methanol (4 mL/2 mL) was stirred at 90° C. under an argon atmosphere for 4 h. After cooling to RT the reaction mixture was poured into water. Precipitated product 19 was collected by filtration and dried under reduced pressure. Yield: 64 mg (81%). LCMS (ESI$^+$) calculated for C$_{10}$H$_9$N$_3$O$_2$ [M+H]$^+$ m/z 204.0773, found 204.2. $^1$H NMR (400 MHz, (CD$_3$)$_2$SO) δ 8.71 (m, 1H), 8.24 (m, 1H), 7.98 (dd, J=8.9, 2.0 Hz, 1H), 7.06 (dd, J=18.0, 11.5 Hz, 1H), 6.15 (dd, J=18.0, 1.0 Hz, 1H), 5.56 (dd, J=11.5, 1.0 Hz, 1H), 4.18 (s, 3H). HPLC (Method 1): Retention time=0.97 min.

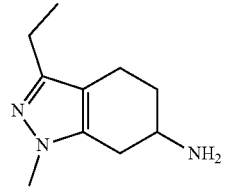

21a

3-Ethyl-1-methyl-4,5,6,7-tetrahydro-1H-indazol-6-ylamine (21a). Prepared according to general procedure B from nitro indazole 19 (reaction time 7 h at 50-80° C., then 18 h at 50° C. under 50 bar hydrogen atmosphere). Yield: 10 mg (38%). LCMS (ESI$^+$) calculated for C$_{10}$H$_{17}$N$_3$ [M+H]$^+$ m/z 180.1501, found 180.2. $^1$H NMR (400 MHz, (CD$_3$)$_2$SO) δ 3.54 (s, 3H), 2.97-3.05 (m, 1H), 2.40 (q, J=7.5 Hz, 2H), 2.33-2.46 (m, 2H), 2.24-2.35 (m, 1H), 2.10-2.19 (m, 1H), 1.73-1.83 (m, 1H), 1.33-1.44 (m, 1H), 1.09 (t, J=7.5 Hz, 3H). HPLC (Method 1): R$_t$=0.70 min.

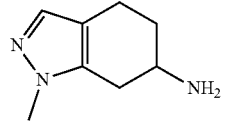

21b

1-Methyl-4,5,6,7-tetrahydro-1H-indazol-6-ylamine (21b). To a solution of 1-methyl-1H-indazol-6-ylamine 20 (200 mg, 1.4 mmol) in methanol (10 mL) was added conc. aq. HCl (186 μL, 1.6 mmol) and palladium (10% on charcoal, 20 mg). The mixture was hydrogenated at 50 bar for 16 h at 50° C. After cooling to RT the reaction mixture was filtered and concentrated under reduced pressure. The remainder was taken up in DMF and was purified by preparative reverse-phase HPLC to give product 21b. Yield: 59 mg (29%). LCMS (ESI$^+$) calculated for C$_8$H$_{13}$N$_3$ [M+H]$^+$ m/z 152.1188, found 152.1. $^1$H NMR (400 MHz, (CD$_3$)$_2$SO) δ 7.14 (s, 1H), 3.64 (s, 3H), 2.90-2.99 (m, 1H), 2.38-2.60 (m, 4H, partially obscured by DMSO signal), 1.90-1.98 (m, 1H), 1.56-1.68 (m, 1H). Note: NH$_2$ signals not visible. HPLC (Method 4): R$_t$=0.57 min.

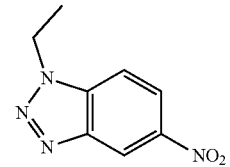

23

1-Ethyl-5-nitro-1H-benzotriazole (23). 2-Fluoro-5-nitroaniline 22 (5.0 g, 32.03 mmol) was dissolved in dry DMSO (50 mL), treated with ethylamine (2M in THF, 56 mL, 112.10 mmol) in a sealed flask and heated at 120° C. After 2 days the reaction mixture was cooled to RT and acetic acid (20 mL) was added followed by addition of NaNO$_2$ (2 M aq solution, 19.2 mL, 38.4 mmol). Stirring was continued for 20 min, then the reaction mixture was acidified to pH=2 with HCl (1M aq solution), water was added and the mixture was extracted with ethyl acetate. The organic phase was dried over MgSO$_4$ and concentrated under reduced pressure. The remainder was purified by preparative MPLC (silica gel, cyclohexane/ethyl acetate, gradient 0-45% ethyl acetate over 40 min) to afford product 23. Yield: 2.87 g (47%). LCMS (ESI$^+$) calculated for C$_8$H$_8$N$_4$O$_2$ [M+H]$^+$ m/z 193.0726, found 193.0. $^1$H NMR (400 MHz, (CD$_3$)$_2$SO) δ 9.03 (m, 1H), 8.40 (dd, J=9.2, 2.0 Hz, 1H), 8.16 (m, 1H), 4.84 (q, J=7.4 Hz, 2H), 1.55 (t, J=7.4 Hz, 3H). HPLC (Method 3): R$_t$=0.44 min.

added Burgess' reagent (5.78 g, 24.26 mmol). After stirring for 3 d at 65° C. the mixture was concentrated under reduced pressure. The remainder was taken up in a mixture of MeOH/water, acidified with TFA and purified by preparative reverse-phase HPLC. Yield: 954 mg (61%). LCMS (ESI$^+$) calculated for C$_8$H$_8$N$_4$O$_2$ [M+H]$^+$ m/z 193.0726, found 193.2. $^1$H NMR (400 MHz, (CD$_3$)$_2$SO) δ 8.78 (dd, J=2.2, 0.8 Hz, 1H), 8.64 (dd, J=7.6, 0.8 Hz, 1H), 7.63 (dd, J=7.6, 2.2 Hz, 1H), 3.18 (q, J=7.5 Hz, 2H), 1.40 (t, J=7.5 Hz, 3H). HPLC (Method 6): R$_t$=0.32 min.

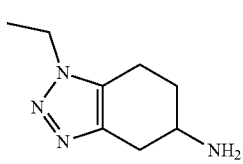

24

1-Ethyl-4,5,6,7-tetrahydro-1H-benzotriazol-5-ylamine (24). Prepared according to general procedure B from nitro benzotriazole 23 (reaction time 2 d). Yield: 800 mg (66%). LCMS (ESI$^+$) calculated for C$_8$H$_{14}$N$_4$ [M+H]$^+$ m/z 167.1297, found 167.1. $^1$H NMR (400 MHz, (CD$_3$)$_2$SO) δ 4.14-4.23 (m, 2H), 3.05-3.13 (m, 1H), 2.77-2.84 (m, 1H), 2.67-2.76 (m, 1H), 2.53-2.63 (m, 1H), 2.25-2.33 (m, 1H), 1.83-1.92 (m, 1H), 1.50-1.62 (m, 1H), 1.35 (t, J=7.2 Hz, 3H). HPLC (Method 3): R$_t$=0.22 min.

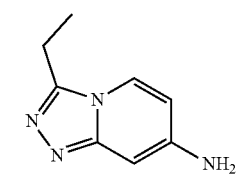

28

3-Ethyl-5,6,7,8-tetrahydro-[1,2,4]triazolo[4,3-a]pyridine-7-ylamine (28). Prepared according to general procedure B from nitro triazolopyridine 27 (reaction time 16 h). Yield: 185 mg (54%). LCMS (ESI$^+$) calculated for C$_8$H$_{14}$N$_4$ [M+H]$^+$ m/z 167.1297, found 167.1. $^1$H NMR (400 MHz, (CD$_3$)$_2$SO) δ 3.89-3.97 (m, 1H), 3.73-3.80 (m, 1H), 3.22-3.28 (m, 1H), 2.87-2.94 (m, 1H), 2.63 (q, J=7.5 Hz, 1H), 2.49 (q, J=7.5 Hz, 1H), 1.90-1.99 (m, 1H), 1.69-1.79 (m, 2H), 1.21 (t, J=7.5 Hz, 3H). HPLC (Method 3): R$_t$=0.10 min.

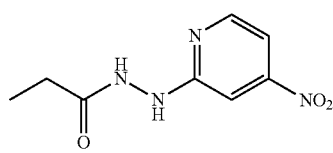

26

Propionic acid N'-(4-nitro-pyridin-2-yl)-hydrazide (26). To a mixture of (4-nitro-pyridin-2-yl)-hydrazine 25 (2.31 g, 8.14 mmol) and DIPEA (5.39 mL, 32.56 mmol) in THF was dropwise added a solution of propionyl chloride (0.78 mL, 8.95 mmol) in THF. After stirring for 15 min at RT, few drops of water were added and the reaction mixture was concentrated under reduced pressure. The remainder was suspended in water and acidified with TFA. The suspension was filtered and purified by preparative HPLC to give product 26. Yield: 1.7 g (quant.). LCMS (ESI$^+$) calculated for C$_8$H$_{10}$N$_4$O$_3$ [M+H]$^+$ m/z 211.0831, found 211.2. $^1$H NMR (400 MHz, (CD$_3$)$_2$SO) δ 9.87 (s, 1H), 9.05 (br s, 1H), 8.37 (dd, J=5.4, 0.4 Hz, 1H), 7.34 (dd, J=5.4, 2.0 Hz, 1H), 7.14 (dd, J=2.0, 0.4 Hz, 1H), 2.22 (q, J=7.6 Hz, 2H), 1.07 (t, J=7.6 Hz, 3H). HPLC (Method 6): R$_t$=0.31 min.

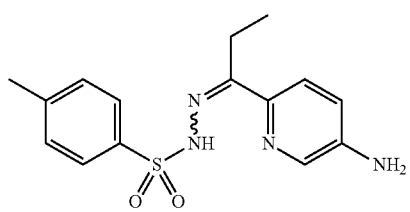

30 p-tolylsulfonic acid [1-(5-amino-pyridin-2-yl)-(propylidene]-hydrazide (30), E/Z-isomers.

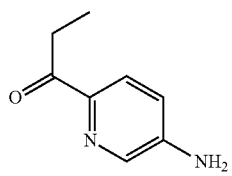

i) 1-(5-Amino-pyridin-2-yl)-propan-1-one. To a solution of ethyl magnesium bromide in diethyl ether (3M, 13.8 mL, 41.4 mmol) was added slowly a mixture of 5-aminopyridine-2-carbonitrile 29 (1.0 g, 8.4 mmol) in diethyl ether (192 mL) under argon atmosphere. The mixture was stirred under reflux for 6 h, then for 16 h at RT. The reaction mixture was poured onto ice (77 g) mixed with conc HCl (15 mL), stirred at RT for 90 min and 16 h at 40° C. The reaction mixture was then made alkaline until pH 9 with aq NaOH (4N) and was extracted 3× with diethyl ether. The combined organic phases were dried over MgSO$_4$, concentrated under reduced pressure and purified by preparative reverse-phase HPLC to afford the product. Yield: 206 mg (16%). LCMS (ESI$^+$)

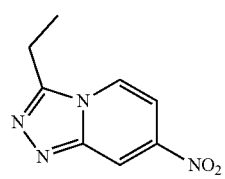

27

3-Ethyl-7-nitro-[1,2,4]triazolo[4,3-a]pyridine (27). To a mixture of 26 (1.70 g, 8.09 mmol) in THF (30 mL) was calculated for C$_8$H$_{10}$N$_2$O [M+H]$^+$ m/z 151.0871, found 151.0. $^1$H NMR (400 MHz, (CD$_3$)$_2$SO) δ 7.95 (d, J=2.7 Hz, 1H), 7.70 (d, J=8.6 Hz, 1H), 6.94 (dd, J=8.6, 2.7 Hz, 1H), 6.20 (br s, 2H), 3.00 (q, J=7.4 Hz, 2H), 1.04 (t, J=7.4 Hz, 3H). HPLC (Method 3): R$_t$=0.29 min. ii) p-tolylsulfonic acid [1-(5-amino-pyridin-2-yl)-(propylidene]-hydrazide (30), E/Z-isomers. To a mixture of p-tolylsulfonohydrazide (272.8 mg, 1.5 mmol) in MeOH (3 mL) was added portionwise 1-(5-amino-pyridin-2-yl)-propan-1-one (200.0 mg, 1.3 mmol) at RT. Another portion of p-tolylsulfonohydrazide (173.6 mg, 0.9 mmol) was added and stirring was continued for 6 h. The reaction mixture was purified by preparative reverse-phase HPLC to obtain product 30 as separable E- and Z-isomers. Yield: E-30: 212 mg (50%). LCMS (EI) calculated for C$_{15}$H$_{18}$N$_4$O$_2$S [M−H]$^-$ m/z 317.1072, found 317.1. $^1$H NMR (400 MHz, (CD$_3$)$_2$SO) δ 10.40 (s, 1H), 7.85 (d, J=2.7 Hz, 1H), 7.77-7.81 (m, 2H), 7.48 (d, J=8.6 Hz, 1H), 7.38-7.42 (m, 2H), 6.88 (dd, J=8.6, 2.7 Hz, 1H), 5.62 (br s, 2H), 2.75 (q, J=7.5 Hz, 2H), 2.37 (s, 3H), 0.93 (t, J=7.5 Hz, 3H). $^{13}$C NMR (101 MHz, (CD$_3$)$_2$SO) δ 158.4, 145.5, 143.1, 141.4, 136.3, 134.2, 129.4, 127.4, 120.8, 120.1, 21.0, 18.3, 10.4. HPLC (Method 3): R$_t$=0.26 min. Yield: Z-30: 212 mg (50%). LCMS (ESI$^+$) calculated for C$_{15}$H$_{18}$N$_4$O$_2$S [M+H]$^+$ m/z 319.1229, found 319.1. $^1$H NMR (400 MHz, (CD$_3$)$_2$SO) δ 14.2 (s, 1H), 7.99 (d, J=2.8 Hz, 1H), 7.70-7.73 (m, 2H), 7.42 (d, J=8.9 Hz, 1H), 7.35-7.40 (m, 2H), 7.03 (dd, J=8.8, 2.8 Hz, 1H), 6.10 (br s, 2H), 2.51 (q, J=7.3 Hz, 2H), 2.36 (s, 3H), 0.97 (t, J=7.3 Hz, 3H). $^{13}$C NMR (101 MHz, (CD$_3$)$_2$SO) δ 147.5, 145.8, 143.1, 139.3, 136.5, 132.9, 129.5, 127.0, 125.0, 120.0, 27.4, 21.0, 11.9. HPLC (Method 3): R$_t$=0.53 min.

31

3-Ethyl-[1,2,3]triazolo[1,5-a]pyridine-6-ylamine (31). Hydrazide Z-30 (240 mg, 0.75 mmol) was dissolved in morpholine (0.66 mL, 7.54 mmol) and stirred for 4 h at 100° C. After cooling to RT the reaction mixture was directly purified by preparative reverse-phase HPLC to obtain product 31. Yield: 84 mg (69%). LCMS On calculated for C$_8$H$_{10}$N$_4$ [M+H]$^+$ m/z 163.0984, found 163.0. $^1$H NMR (400 MHz, (CD$_3$)$_2$SO) δ 7.99 (dd, J=1.7, 0.7 Hz, 1H), 7.62 (dd, J=9.3, 0.7 Hz, 1H), 6.87 (dd, J=9.4, 1.7 Hz, 1H), 5.36 (br s, 2H), 2.84 (q, J=7.6 Hz, 2H), 1.26 (t, J=7.6 Hz, 3H). HPLC (Method 3): R$_t$=0.30 min.

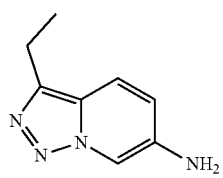

32

3-Ethyl-4,5,6,7-tetrahydro-[1,2,3]triazolo[1,5-a]pyridine-6-ylamine (32). To a solution of amino triazolo pyridine 31 (84 mg, 518 μmol) in methanol (5 mL) was added palladium (10% on charcoal, 25 mg). The mixture was hydrogenated at 0.5 bar for 16 h at RT, then filtered and concentrated under reduced pressure. The remainder was taken up in DMF and purified by preparative reverse-phase HPLC to give product 32. Yield: 20 mg (23%). LCMS (ESI$^+$) calculated for C$_8$H$_{14}$N$_4$ [M+H]$^+$ m/z 167.1297, found 167.1. $^1$H NMR (400 MHz, (CD$_3$)$_2$SO) δ 4.32 (m, 1H), 3.84 (m, 1H), 3.27-3.33 (m, 1H, largely obscured by water signal), 2.81 (m, 1H), 2.58-2.67 (m, 1H), 2.53 (q, J=7.6 Hz, 2H), 1.86-1.94 (m, 1H), 1.77 (br s, 2H), 1.60-1.70 (m, 1H), 1.15 (t, J=7.6 Hz, 3H). HPLC (Method 3): R$_t$=0.25 min.

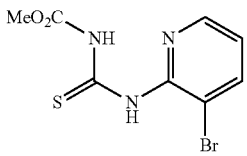

34a 1-(3-Bromo-pyridin-2-yl)-3-carboethoxy-thiourea (34a). Ethyl isocyanatoformate (52.5 g, 397 mmol) is added dropwise at 5° C. to a solution of 2-amino-3-bromopyridine (33a) (66 g, 378 mmol) in DCM (660 mL). After stirring for 16 h at RT the reaction mixture is concentrated under reduced pressure to give crude product, which is washed with PE and dried. Yield: 105 g (87%). LCMS (ESI$^+$) calculated for C$_9$H$_{10}$BrN$_3$O$_2$S [M+H]$^+$ m/z 303.9755, found 304.0. $^1$H NMR (400 MHz, (CD$_3$)$_2$SO) δ 11.43 (br s, 2H), 8.49 (dd, J=4.6, 1.5 Hz, 1H), 8.17 (dd, J=7.9, 1.5 Hz, 1H), 7.33 (dd, J=7.9, 4.7 Hz, 1H), 4.23 (q, J=7.1 Hz, 2H), 1.27 (t, J=7.1 Hz, 3H). TLC (silica gel, PE/EE 3:1): R$_f$=0.4.

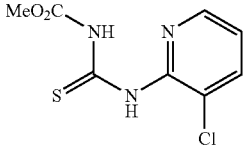

34b 1-(3-Chloro-pyridin-2-yl)-3-carboethoxy-thiourea (34b). Prepared by a procedure similar to that described for the synthesis of 34a starting from 2-amino-3-chloropyridine (33b) (3.16 g, 25 mmol) in DMF. Yield: 6.11 g (96%). LCMS (ESI$^+$) calculated for C$_9$H$_{10}$ClN$_3$O$_2$S [M+H]$^+$ m/z 260.0261, found 260.1. $^1$H NMR (400 MHz, (CD$_3$)$_2$SO) δ 11.45 (br s, 1H), 11.42 (br s, 1H), 8.45 (dd, J=4.7, 1.4 Hz, 1H), 8.04 (dd, J=8.0, 1.4 Hz, 1H), 7.42 (dd, J=8.0, 4.7 Hz, 1H), 4.23 (q, J=7.1 Hz, 2H), 1.27, (t, J=7.1 Hz, 3H). HPLC (method 1) R$_t$=0.64 min.

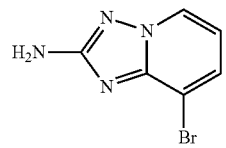

35a

8-Bromo-[1,2,4]triazolo[1,5-a]pyridine-2-ylamine (35a). To a suspension of DIPEA (128.2 g, 984 mmol) and hydroxylamine hydrochloride (115.1 g, 1.64 mol) in a mixture of ethanol/methanol (400 mL/400 mL) is added 1-(3-bromopyridin-2-yl)-3-carboethoxy-thiourea (34a) (105.0 g, 328 mmol). After stirring for 2 h at RT, the reaction mixture is heated under reflux for 18 h. After cooling to RT the precipitate is collected, washed with water and EE and dried to give the product (35a). Yield: 55 g (75%). LCMS (ESI⁺) calculated for $C_6H_5BrN_4$ [M+H]⁺ m/z 212.9776, found 213.1. ¹H NMR (400 MHz, $(CD_3)_2SO$) δ 8.58 (dd, J=6.6, 0.7 Hz, 1H), 7.73 (dd, J=7.6, 0.7 Hz, 1H), 6.81 (dd, J=7.5, 6.7 Hz, 1H), 6.24 (br s, 2H). TLC (silica gel, DCM/MeOH 10:1): $R_f$=0.5.

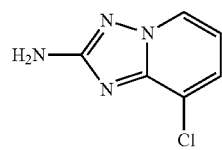

35b

8-Chloro-[1,2,4]triazolo[1,5-a]pyridine-2-ylamine (35b). Prepared by a procedure similar to that described for the synthesis of 35a starting from 1-(3-chloro-pyridin-2-yl)-3-carboethoxy-thiourea (34b) (6.1 g, 23.5 mmol). Yield: 2.95 g (74%). LCMS (ESI⁺) calculated for $C_6H_5ClN_4$ [M+H]⁺ m/z 169.0281, found 169.0. ¹H NMR (400 MHz, $(CD_3)_2SO$) δ 8.54 (dd, J=6.7, 0.8 Hz, 1H), 7.59 (d, J=7.7, 0.8 Hz, 1H), 6.86 (dd, J=7.7, 6.7 Hz, 1H), 6.22 (br s, 2H). HPLC (method 1) $R_t$=0.57 min.

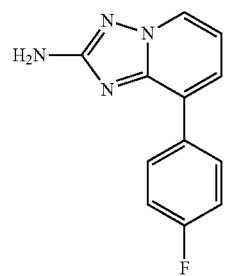

36a 8-(4-Fluoro-phenyl)-[1,2,4]triazolo[1,5-a]pyridine-2-ylamine (36a). A mixture of 8-bromo-[1,2,4]triazolo[1,5-a]pyridine-2-ylamine (35a) (10 g, 45 mmol), 4-fluoro-phenyl-boronic acid (12.61 g, 89 mmol), [1,1'-bis(diphenylphosphino)ferrocene]dichloro palladium(II) (2.93 g, 4 mmol) and sodium carbonate solution (2N in water, 44.6 mL, 89 mmol) in 1,4-dioxane (200 mL) was stirred at 110° C. under nitrogen atmosphere for 12 h. The reaction mixture was diluted with water and extracted with ethyl acetate. The organic phase was dried over $Na_2SO_4$ and concentrated under reduced pressure. The remainder was purified by preparative MPLC (silica gel, PE/ethyl acetate 20:1) to afford the product (36a). Yield: 8.6 g (80%). LCMS (ESI⁺) calculated for $C_{12}H_9FN_4$ [M+H]⁺ m/z 229.0889, found 229.1. ¹H NMR (400 MHz, $(CD_3)_2SO$) δ 8.54 (dd, J=6.7, 1.0 Hz, 1H), 8.14-8.21 (m, 2H), 7.70 (dd, J=7.3, 1.0 Hz, 1H), 7.29-7.37 (m, 2H), 6.97 (dd, J=7.3, 6.7 Hz, 1H), 6.12 (s, 2H). TLC (silica gel, PE/ethyl acetate 10:1): $R_f$=0.5. HPLC (method 3) $R_t$=0.43 min.

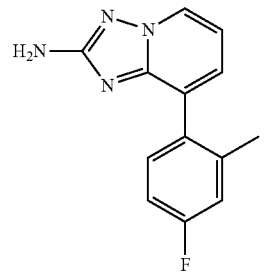

36b 8-(4-Fluoro-2-methyl-phenyl)-[1,2,4]triazolo[1,5-a]pyridine-2-ylamine (36b). Prepared by a procedure similar to that described for the synthesis of 36a starting from 4-fluoro-2-methyl-phenyl boronic acid (27.74 g, 178 mmol) and 8-bromo-[1,2,4]triazolo[1,5-a]pyridine-2-ylamine (35a) (20 g, 89 mmol). Yield: 17 g (75%). LCMS (ESI⁺) calculated for $C_{13}H_{11}FN_4$ [M+H]⁺ m/z 243.1046, found 243.1. ¹H NMR (400 MHz, $(CD_3)_2SO$) δ 8.56 (dd, J=6.7, 1.0 Hz, 1H), 7.31-7.36 (m, 1H), 7.30 (dd, J=7.3, 1.0 Hz, 1H), 7.17 (m, 1H), 7.09 (m, 1H), 6.94 (dd, J=7.3, 6.7 Hz, 1H), 6.00 (s, 2H), 2.17 (s, 3H). TLC (silica gel, PE/ethyl acetate 4:1): $R_f$=0.5. HPLC (method 3) $R_t$=0.43 min.

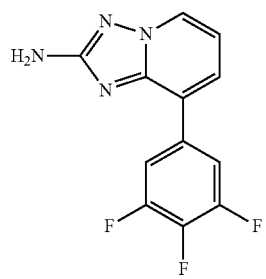

36c 8-(3,4,5-Trifluoro-phenyl)-[1,2,4]triazolo[1,5-a]pyridine-2-ylamine (36c). Prepared by a procedure similar to that described for the synthesis of 36a starting from 3,4,5-trifluoro-phenyl boronic acid (1.5 g, 8.5 mmol), 8-bromo-[1,2,4]triazolo[1,5-a]pyridine-2-ylamine (35a) (1.8 g, 8.5 mmol) and [1,1'-bis(diphenylphosphino)ferrocene]dichloro palladium(II), complex with dichloromethane (1:1) (0.7 g, 0.85 mmol). Yield: 1.03 g (45%). LCMS (ESI⁺) calculated for $C_{12}H_7F_3N_4$ [M+H]⁺ m/z 265.0701, found 265.1. ¹H NMR (400 MHz, $(CD_3)_2SO$) δ 8.61 (dd, J=6.6, 0.8 Hz, 1H), 8.23-8.32 (m, 2H), 7.90 (dd, J=7.6, 0.8 Hz, 1H), 7.00 (dd, J=7.5, 6.8 Hz, 1H), 6.24 (br s, 2H). HPLC (method 6): $R_t$=0.51 min.

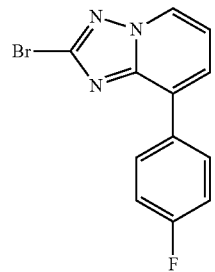

37a

2-Bromo-8-(4-fluoro-phenyl)-[1,2,4]triazolo[1,5-a]pyridine (37a). A mixture of tert-nitrobutane (8.35 g, 78.76 mmol) and copper(II) bromide (17.77 g, 78.76 mmol) in acetonitrile (180 mL) was heated to 60° C., 8-(4-fluoro-phenyl)-[1,2,4]triazolo[1,5-a]pyridine-2-ylamine (36a) (8.60 g, 35.8 mmol) was added in small portions. After complete addition, the mixture was heated to 75° C. for 1 h. Further portions of tert-nitrobutane and copper(II) bromide were added and the mixture heated to 75° C. for an additional hour. The mixture was cooled to RT, water was added and extracted with DCM. The organic phase was washed with brine, dried over $MgSO_4$, filtered and concentrated under reduced pressure to obtain crude material which was purified by MPLC (silica gel, PE/ethyl acetate 8:1) to obtain the product (37a). Yield: 6.17 g (59%). LCMS (ESI$^+$) calculated for $C_{12}H_7BrFN_3$ [M+H]$^+$ m/z 291.9886, found 292.0. $^1$H NMR (400 MHz, $(CD_3)_2SO$) δ 8.95 (dd, J=6.7, 1.0 Hz, 1H), 8.11-8.17 (m, 2H), 7.99 (dd, J=7.4, 1.0 Hz, 1H), 7.34-7.43 (m, 2H), 7.36 (dd, J=7.4, 6.7 Hz, 1H). TLC (silica gel, PE/ethyl acetate 4:1): $R_f$=0.5.

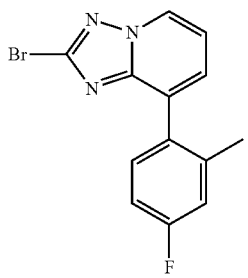

37b

2-Bromo-8-(4-fluoro-2-methyl-phenyl)-[1,2,4]triazolo[1,5-a]pyridine (37b). To a mixture of 8-(4-fluoro-2-methyl-phenyl)-[1,2,4]triazolo[1,5-a]pyridine-2-ylamine (36b) (15 g, 62 mmol) in hydrobromic acid (47% in water, 70.8 mL, 62 mmol) at 0° C. was added an aqueous solution of sodium nitrite (10.68 g in 150 mL water, 155 mmol). After stirring for 2 h copper(I) bromide (8.88 g, 62 mmol) was added. After stirring for 4 h at 0° C. the reaction mixture was diluted with ethyl acetate (50 mL) and water (20 mL). The organic phase was separated, dried over $Na_2SO_4$, filtered and concentrated under reduced pressure to obtain crude material which was purified by MPLC (silica gel, PE/ethyl acetate 9:1) to obtain the product (37b). Yield: 10.0 g (53%). LCMS (ESI$^+$) calculated for $C_{13}H_9BrFN_3$ [M+H]$^+$ m/z 306.0042, found 306.0. $^1$H NMR (400 MHz, $(CD_3)_2SO$) δ 8.98 (dd, J=6.9, 0.8 Hz, 1H), 7.65 (dd, J=7.2, 0.8 Hz, 1H), 7.39 (m, 1H), 7.34 (dd, J=7.2, 6.9 Hz, 1H), 7.24 (m, 1H), 7.15 (m, 1H), 2.16 (s, 3H). TLC (silica gel, PE/ethyl acetate 1:1): $R_f$=0.6.

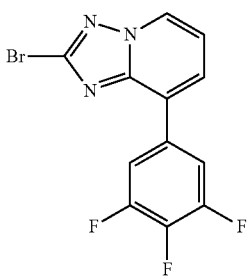

37c

2-Bromo-8-(3,4,5-trifluoro-phenyl)-[1,2,4]triazolo[1,5-a]pyridine (37c). To a mixture of 8-(3,4,5-Trifluoro-phenyl)-[1,2,4]triazolo[1,5-a]pyridine-2-ylamine (36c) (1.22 g, 4.6 mmol) and $NaNO_2$ (955 mg, 4.31 mmol) in ice water (~1 mL) hydrobromic acid (48% in water, 11.2 mL, 99 mmol) was added dropwise at −5° C. After complete addition the reaction mixture was slowly warmed up to RT, then refluxed for 1 d. After cooling to RT the precipitate was filtered off and purified by preparative reverse-phase HPLC to afford the product (37c). Yield: 627 mg (42%). LCMS (ESI$^+$) calculated for $C_{12}H_5BrF_3N_3$ [M+H]$^+$ m/z 327.9697, found 328.0. $^1$H NMR (400 MHz, $(CD_3)_2SO$) δ 9.02 (dd, J=6.8, 0.8 Hz, 1H), 8.11-8.20 (m, 3H), 7.39 (m, 1H). HPLC (method 6): $R_t$=0.75 min.

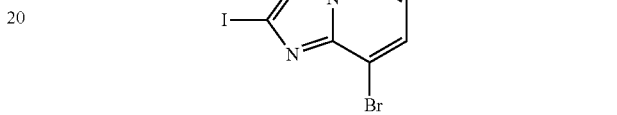

38a

8-Bromo-2-iodo-[1,2,4]triazolo[1,5-a]pyridine (38a). Prepared according to literature procedure (Menet, C. J. M.; Blanc, J.; Hodges, A. J.; Burli, R. W.; Breccia, P.; Blackaby, W. P.; Van Rompaey, L. J. C.; Fletcher, S. R. [1,2,4]Triazolo[1,5-a]pyridines as JAK inhibitors. WO 2010010184) starting from 8-bromo-[1,2,4]triazolo[1,5-a]pyridine-2-ylamine (35a) (5.0 g, 23.47 mmol). Yield: 4.35 g (57%). LCMS (ESI$^+$) calculated for $C_6H_3BrIN_3$ [M+H]$^+$ m/z 323.8633, found 323.9. $^1$H NMR (400 MHz, $(CD_3)_2SO$) δ 8.96 (dd, J=6.8, 0.8 Hz, 1H), 8.01 (dd, J=7.6, 0.8 Hz, 1H), 7.12 (dd, J=7.5, 6.9 Hz, 1H). HPLC (method 5): Rt=0.52 min.

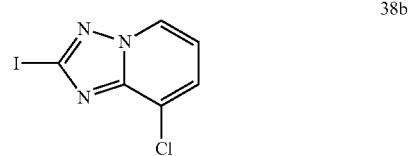 [SMILES: Brc1cccn2nc(I)nc12]

38b

8-Chloro-2-iodo-[1,2,4]triazolo[1,5-a]pyridine (38b). To a mixture of sodium nitrite (7.8 g, 112.7 mmol) and potassium iodide (23.4 g, 140.9 mmol) in water (30 mL) was added a mixture of para-toluene sulfonic acid monohydrate (42.9 g, 225.4 mmol) in acetonitrile (500 mL) at RT followed by addition of 8-chloro-[1,2,4]triazolo[1,5-a]pyridine-2-ylamine (35b) (9.5 g, 56.4 mmol). After stirring at 50° C. for 2 h the reaction mixture was diluted with water and sodium thiosulfate was added until color change persisted. The mixture was extracted twice with DCM and the combined organic phases were concentrated under reduced pressure. The remainder was triturated with water, filtered and dried to give the product (38b). Yield: 13.34 g (85%). LCMS (ESI$^+$) calculated for $C_6H_3ClIN_3$ [M+H]$^+$ m/z 279.9138, found 279.9. $^1$H NMR (400 MHz, $(CD_3)_2SO$) δ 8.94 (dd, J=6.8, 0.9 Hz, 1H), 7.88 (dd, J=7.7, 0.9 Hz, 1H), 7.19 (dd, J=7.7, 6.8 Hz, 1H). HPLC (Method 1): $R_t$=0.77 min.

39a

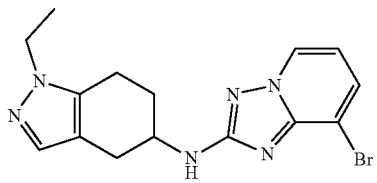

(8-Bromo-[1,2,4]triazolo[1,5-a]pyridine-2-yl)-(1-ethyl-4,5,6,7-tetrahydro-1H-indazol-5-yl)-amine (39a). A mixture of 8-bromo-2-iodo-[1,2,4]triazolo[1,5-a]pyridine (38a) (200 mg, 617 µmol), 1-ethyl-4,5,6,7-tetrahydro-1H-indazol-5-ylamine (13a) (245 mg, 1.48 mmol) and cesium fluoride (131 mg, 864 µmol) in DMSO (2.5 mL) was heated at 130-160° C. for 10 h with microwave irradiation. After cooling to RT the precipitates were filtered off and discarded. The filtrate was taken up in ethyl acetate and water and was extracted 3× with ethyl acetate. The combined organic phases were dried over sodium sulfate and concentrated under reduced pressure. The residue was purified by preparative reversed-phase HPLC to give the product (39a). Yield: 86 mg, TFA salt (29%). LCMS (ESI$^+$) calculated for $C_{15}H_{17}BrN_6$ [M+H]$^+$ m/z 361.0776, found 361.1. $^1$H NMR (400 MHz, (CD$_3$)$_2$SO) δ 8.64 (dd, J=6.6, 0.8 Hz, 1H), 7.75 (dd, J=7.7, 0.8 Hz, 1H), 7.18 (s, 1H), 6.94 (very br s, 1H), 6.81 (dd, J=7.7, 6.6 Hz, 1H), 3.98 (q, J=7.2 Hz, 2H), 3.81-3.90 (m, 1H), 2.76-2.91 m, 2H), 2.61-2.72 (m, 1H), 2.41-2.51 (m, 1H, partially obscured by DMSO signal), 2.10-2.18 (m, 1H), 1.75-1.87 (m, 1H), 1.29 (t, J=7.2 Hz, 3H). HPLC (Method 6): R$_t$=0.91 min.

R-39a

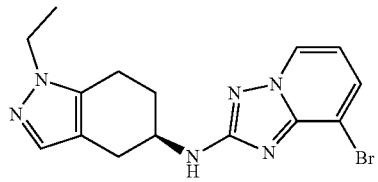

(R)-(8-Bromo-[1,2,4]triazolo[1,5-a]pyridine-2-yl)-(1-ethyl-4,5,6,7-tetrahydro-1H-indazol-5-yl)-amine (R-39a). Prepared in analogy to the preparation of racemic 39a starting from chiral R-13a and 38a. Yield: 550 mg (46%). $^1$H NMR (400 MHz, (CD$_3$)$_2$SO) δ 8.64 (dd, J=6.6, 0.8 Hz, 1H), 7.75 (dd, J=7.7, 0.8 Hz, 1H), 7.18 (s, 1H), 6.94 (very br s, 1H), 6.81 (dd, J=7.7, 6.6 Hz, 1H), 3.98 (q, J=7.2 Hz, 2H), 3.81-3.90 (m, 1H), 2.76-2.91 m, 2H), 2.61-2.72 (m, 1H), 2.41-2.51 (m, 1H, partially obscured by DMSO signal), 2.10-2.18 (m, 1H), 1.75-1.87 (m, 1H), 1.29 (t, J=7.2 Hz, 3H). HPLC (Method 4): R$_t$=0.91 min.

S-39a

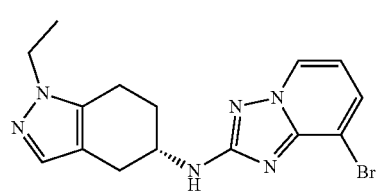

(S)-(8-Bromo-[1,2,4]triazolo[1,5-a]pyridine-2-yl)-(1-ethyl-4,5,6,7-tetrahydro-1H-indazol-5-yl)-amine (S-39a). Prepared in analogy to the preparation of racemic 39a starting from chiral S-13a and 38a. Yield: 206 mg (62%). HPLC (Method 5): R$_t$=0.91 min.

39b

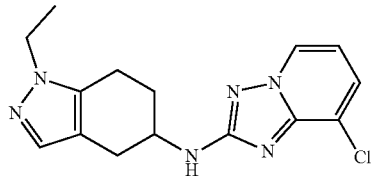

(8-Chloro-[1,2,4]triazolo[1,5-a]pyridine-2-yl)-(1-ethyl-4,5,6,7-tetrahydro-1H-indazol-5-yl)-amine (39b). A mixture of 1-ethyl-4,5,6,7-tetrahydro-1H-indazol-5-ylamine (13a) (1.57 g, 9.48 mmol), 8-chloro-2-iodo-[1,2,4]triazolo[1,5-a]pyridine (38b) (2.65 g, 9.48 mmol), dichloro[1,3-bis(2,6-di-3-pentylphenyl)imidazole-2-ylidene](3-chloropyridyl)palladium(II) (280.0 mg, 325.0 µmol) and sodium tert-butoxide (3.65 g, 37.93 mmol) in 1,4-dioxane (40 mL) was stirred at 100° C. under argon atmosphere for 3 h. After cooling the reaction mixture was poured into ice water and extracted 3× with ethyl acetate. The combined organic phases were dried over sodium sulphate and concentrated under reduced pressure. The remainder was triturated with diethyl ether to give the product (39b). Yield: 1.55 g (51%). LCMS (ESI$^+$) calculated for $C_{15}H_{17}ClN_6$ [M+H]$^+$ m/z 317.1281, found 317.1. $^1$H NMR (400 MHz, (CD$_3$)$_2$SO) δ 8.61 (dd, J=6.7, 0.8 Hz, 1H), 7.61 (dd, J=7.8, 0.9 Hz, 1H), 7.14 (s, 1H), 6.91 (d, J=7.6 Hz, 1H), 6.87 (dd, J=7.7, 6.7 Hz, 1H), 3.97 (q, J=7.2 Hz, 2H), 3.80-3.92 (m, 1H), 2.75-2.91 (m, 2H), 2.60-2.73 (m, 1H), 2.41-2.51 (m, 1H), 2.10-2.19 (m, 1H), 1.75-1.87 (m, 1H), 1.28 (t, J=7.2 Hz, 3H). HPLC (Method 1): R$_t$=0.85 min.

41

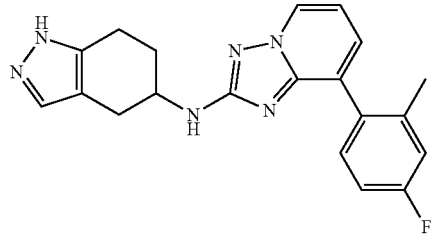

[8-(4-Fluoro-2-methyl-phenyl)-[1,2,4]triazolo[1,5-a]pyridine-2-yl]-(4,5,6,7-tetrahydro-1H-indazol-5-yl)-amine (41). To a mixture of 4,5,6,7-tetrahydro-1H-indazol-5-amine dihydrochloride (52 mg, 245 µmol), 2-bromo-8-(4-fluoro-2-methyl-phenyl)-[1,2,4]triazolo[1,5-a]pyridine (37b) (50 mg, 163 µmol) and Cs$_2$CO$_3$ (213 mg, 653 µmol) in toluene (2 mL) was added dichloro[1,3-bis(2,6-di-3-pentylphenyl)imidazole-2-ylidene](3-chloropyridyl)palladium(II) (6.5 mg, 8 µmol). The reaction mixture was stirred at 110° C. for 5 d. To the reaction mixture was added 1,4-dioxane (1 mL) and water (0.1 mL) and stirring was continued for 16 h at 120° C. After cooling to RT the reaction mixture was concentrated under reduced pressure, taken up in 1,4-dioxane, filtered over Alox and purified by preparative reverse-phase HPLC to afford the product (41). Yield: 3 mg (5%). LCMS (ESI$^+$) calculated for $C_{20}H_{19}FN_6$ [M+H]$^+$ m/z 363.1733, found 363.2. $^1$H NMR (400 MHz, (CD$_3$)$_2$SO) δ 8.99 (dd, J=6.8, 1.1 Hz, 1H), 7.64 (dd, J=7.3, 1.1 Hz, 1H), 7.53 (s, 1H), 7.44 (m, 1H), 7.32 (m, 1H), 7.26 (m, 1H), 7.16 (m, 1H), 2.99-3.17 (m, 2H), 2.83-2.94 (m, 1H), 2.66-2.73 (m, 1H), 2.22 (s, 3H), 2.14-2.21 (m, 1H), 1.85-1.94 (m, 1H), 1.51-1.62 (m, 1H). Note: Both NH signals were not visible. HPLC (Method 1): $R_t$=0.94 min.

General procedure C-1: preparation of final compounds 42-45, 47, 48, 50, 51, 53-55: To a mixture of 2-halo-triazolo pyridine 37a-c (1 equiv), amine 13a-g, 21a, 24 or 28 (2 equiv) and sodium tert-butoxide (4 equiv) in degassed 1,4-dioxane (0.2 M) under Argon atmosphere was added Johnphos (0.1 equiv) and tris-(dibenzylidene acetone)dipalladium(0) (0.1 equiv). The reaction mixture was degassed, put again under argon atmosphere and stirred for 4-16 h at 80° C. After cooling to RT the reaction mixture was filtered and purified by preparative reverse-phase HPLC to furnish the desired products.

General procedure C-2: preparation of final compounds 40, (R)-42, 46, 49 and 52: A mixture of 2-halo triazolo pyridine 38b or 37c (1 equiv), amine R-13a, 13f, 17, 21b or 32 (1 equiv) and cesium fluoride (5 equiv) in DMSO (0.1-0.3M) was heated at 130-160° C. for 10 h with microwave irradiation. After cooling to RT the precipitates were filtered off and discarded. The filtrate was taken up in ethyl acetate and water and was extracted 3× with ethyl acetate. The combined organic phases were dried over sodium sulfate and concentrated under reduced pressure. The residue was purified by preparative reversed-phase HPLC to give the desired products.

General procedure D-1: preparation of final compounds 56-63, 65, 68-69: To a mixture of chloro triazolo pyridine 39b (1 equiv), the respective aryl boronic acid (2 equiv) and $K_3PO_4$ (2 equiv) in THF/water mixture (0.1 M, v/v 10:1) was added chloro-(2-dicyclohexylphosphino-2', 6'-dimethoxy-1,1'-biphenyl)-[2-(2'amino-1,1'-biphenyl)]palladium (II) (0.1 equiv) under argon atmosphere. The reaction mixture was degassed, put under argon atmosphere again and heated at 120° C. for 16 h. After cooling to RT the mixture was filtered and purified by preparative reverse-phase HPLC to give the products.

General procedure D-2: preparation of final compounds R-61, S-61, 64, 66 and 70-73: To a mixture of bromo triazolo pyridine 39a (1 equiv), the respective (hetero)aryl boronic acid or ester (1.1 equiv) in 1,4-dioxane/methanol mixture (0.05 M, v/v 2:1) were added aqueous sodium carbonate solution (2 M, 4 equiv) and [1,1'-bis(diphenylphosphino)ferrocene]dichloropalladium(II), complex with dichloromethane (1:1) (0.03 equiv) under argon atmosphere. The reaction mixture was heated at 90° C. for 16 h. After cooling to RT the mixture was filtered and purified by preparative reverse-phase HPLC to give the products.

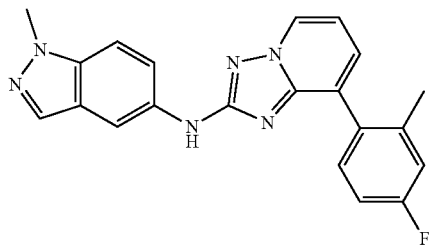

9

[8-(4-fluoro-2-methyl-phenyl)-[1,2,4]triazolo[1,5-a]pyridine-2-yl]-(1-methyl-1H-indazol-5-yl)-amine (9). Palladium acetate (8 mg, 36 µmol) and X-Phos (17 mg, 36 µmol) were added to a mixture of 2-halo-triazolo pyridine 37b (110 mg, 359 µmol) and 1-methyl-1H-indazol-5-ylamine (58 mg, 395 µmol) in 1,4-dioxane (5 mL) under an argon atmosphere. After 45 min at 140° C. (microwave irradiation), the mixture was cooled to RT and an additional portion of 1-methyl-1H-indazol-5-ylamine (15 mg, 102 µmol) was added. The reaction mixture was heated for another 45 min at 140° C. under microwave irradiation, then cooled to RT and acidified with TFA. The mixture was filtered and concentrated under reduced pressure. The remainder was purified by preparative reverse-phase HPLC to obtain compound 9. Yield: 87 mg, TFA salt (50%). LCMS (ESI$^+$) calculated for $C_{21}H_{17}FN_6$ [M+H]$^+$ m/z 373.1577, found 373.1. $^1$H NMR (400 MHz, (CD$_3$)$_2$SO) δ 9.65 (s, 1H), 8.84 (dd, J=6.6, 0.9 Hz, 1H), 8.16 (m, 1H), 7.94 (s, 1H), 7.38-7.56 (m, 4H), 7.22 (m, 1H), 7.13 (m, 1H), 7.08 (dd, J=7.3, 6.6 Hz, 1H), 4.00 (s, 3H), 2.22 (s, 3H). HPLC (Method 5): $R_t$=0.70 min.

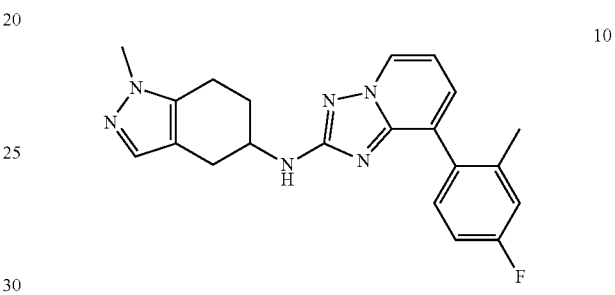

10

[8-(4-fluoro-2-methyl-phenyl)-[1,2,4]triazolo[1,5-a]pyridine-2-yl]-(1-methyl-4,5,6,7-tetrahydro-1H-indazol-5-yl)-amine (10). Prepared according to general procedure C-1 using triazolo pyridine 37b and 1-methyl-4,5,6,7-tetrahydro-1H-indazol-5-ylamine (as dihydrochloride salt, source: Chemizon, order no. 006-002, CAS no. 1228878-82-7). Yield: 100 mg (41%). HRMS (ESI$^+$) calculated for $C_{21}H_{21}FN_6$ [M+H]$^+$ m/z 377.1890, found 377.1892. $^1$H NMR (400 MHz, (CD$_3$)$_2$SO) δ 8.63 (dd, J=6.7, 1.1 Hz, 1H), 7.30-7.37 (m, 1H), 7.32 (dd, J=7.3, 1.1 Hz, 1H), 7.17 (m, 1H), 7.10 (s, 1H), 7.05-7.12 (m, 1H), 6.95 (dd, J=7.3, 6.7 Hz, 1H), 6.65 (d, J=7.6 Hz, 1H), 3.74-3.85 (m, 1H), 3.64 (s, 3H), 2.68-2.87 (m, 2H), 2.56-2.68 (m, 1H), 2.37-2.46 (m, 1H), 2.18 (s, 3H), 2.07-2.17 (m, 1H), 1.70-1.82 (m, 1H). HPLC (Method 1): $R_t$=0.98 min.

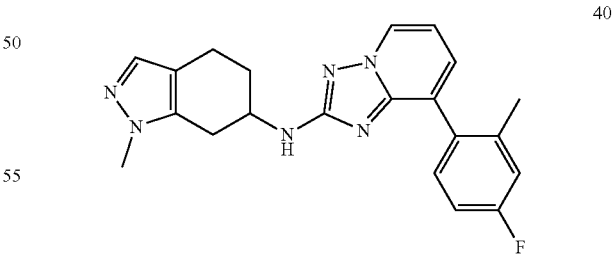

40

[8-(4-Fluoro-2-methyl-phenyl)-[1,2,4]triazolo[1,5-a]pyridine-2-yl]-(1-methyl-4,5,6,7-tetrahydro-1H-indazol-6-yl)-amine (40). Prepared according to general procedure C-2 using triazolo pyridine 37b and amine 21b (1 equiv) by heating at 160° C. for 6 h under microwave irradiation. Yield: 29 mg, TFA salt (20%). LCMS (ESI$^+$) calculated for $C_{21}H_{21}FN_6$ [M+H]$^+$ m/z 377.1890, found 377.2. $^1$H NMR (400 MHz, (CD$_3$)$_2$SO) δ 8.65 (dd, J=6.6, 1.0 Hz, 1H), 7.35

(dd, J=7.3, 1.1 Hz, 1H), 7.32-7.37 (m, 1H), 7.18 (m, 1H), 7.16 (s, 1H), 7.09 (m, 1H), 6.98 (dd, J=7.3, 6.6 Hz, 1H), 6.78 (br s, 1H), 3.87-3.96 (m, 1H), 3.63 (s, 3H, partially obscured by water signal), 3.01-3.08 (m, 1H), 2.41-2.63 (m, 3H, partially obscured by DMSO signal), 2.19 (s, 3H), 1.96-2.05 (m, 1H), 1.64-1.76 (m, 1H). HPLC (Method 5): $R_t$=0.57 min.

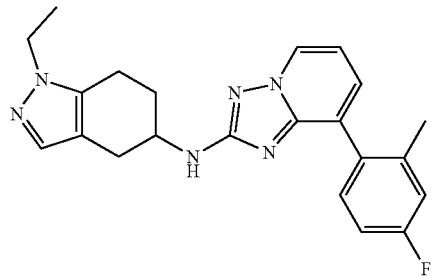

42

(1-Ethyl-4,5,6,7-tetrahydro-1H-indazol-5-yl)-[8-(4-fluoro-2-methyl-phenyl)-[1,2,4]triazolo[1,5-a]pyridine-2-yl]-amine (42). Prepared according to general procedure C-1 using triazolo pyridine 37b and amine 13a. Yield: 35 mg (50%). LCMS (ESI$^+$) calculated for $C_{22}H_{23}FN_6$ [M+H]$^+$ m/z 391.2046, found 391.2. $^1$H NMR (400 MHz, (CD$_3$)$_2$SO) δ 8.63 (dd, J=6.7, 1.1 Hz, 1H), 7.31-7.36 (m, 2H), 7.17 (m, 1H), 7.12 (s, 1H), 7.09 (m, 1H), 6.95 (dd, J=7.3, 6.7 Hz, 1H), 6.67 (d, J=7.5 Hz, 1H), 3.95 (q, J=7.2 Hz, 2H), 3.75-3.86 (m, 1H), 2.73-2.88 (m, 2H), 2.57-2.68 (m, 1H), 2.38-2.46 (m, 1H), 2.18 (s, 3H), 2.08-2.17 (m, 1H), 1.70-1.82 (m, 1H), 1.27 (t, J=7.2 Hz, 3H). HPLC (Method 1): $R_t$=1.01 min.

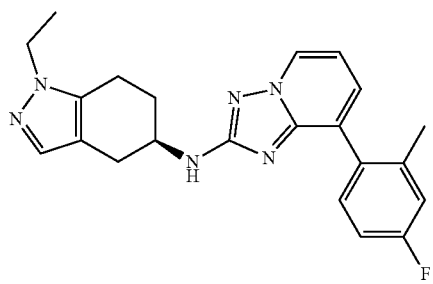

(R)-42

(R)-(1-Ethyl-4,5,6,7-tetrahydro-1H-indazol-5-yl)-[8-(4-fluoro-2-methyl-phenyl)-[1,2,4]triazolo[1,5-a]pyridine-2-yl]-amine ((R)-42). Prepared according to general procedure C-2 using triazolo pyridine 37b and chiral amine R-13a. Yield: 508 mg (80%). HRMS (ESI$^+$) calculated for $C_{22}H_{23}FN_6$ [M+H]$^+$ m/z 391.2046, found 391.2050. $^1$H NMR (400 MHz, (CD$_3$)$_2$SO) δ 8.63 (dd, J=6.7, 1.1 Hz, 1H), 7.31-7.36 (m, 2H), 7.17 (m, 1H), 7.12 (s, 1H), 7.09 (m, 1H), 6.95 (dd, J=7.3, 6.7 Hz, 1H), 6.67 (d, J=7.5 Hz, 1H), 3.95 (q, J=7.2 Hz, 2H), 3.75-3.86 (m, 1H), 2.73-2.88 (m, 2H), 2.57-2.68 (m, 1H), 2.38-2.46 (m, 1H), 2.18 (s, 3H), 2.08-2.17 (m, 1H), 1.70-1.82 (m, 1H), 1.27 (t, J=7.2 Hz, 3H). HPLC (Method 5): $R_t$=0.56 min. Enantiomeric purity (method 15): 97.0% ee. Specific optical rotation: $[\alpha]^{20}_D$=+5.1° (c 0.396 mg/mL, MeOH).

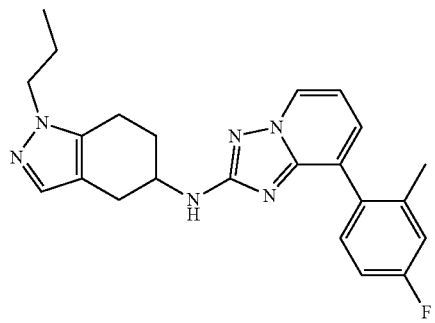

43

[8-(4-fluoro-2-methyl-phenyl)-[1,2,4]triazolo[1,5-a]pyridine-2-yl]-(1-propyl-4,5,6,7-tetrahydro-1H-indazol-5-yl)-amine (43). Prepared according to general procedure C-1 using triazolo pyridine 37b and amine 13c. Yield: 29 mg (48%). LCMS (ESI$^+$) calculated for $C_{23}H_{25}FN_6$ [M+H]$^+$ m/z 405.2203, found 405.3. $^1$H NMR (400 MHz, (CD$_3$)$_2$SO) δ 8.63 (dd, J=6.6, 1.0 Hz, 1H), 7.30-7.36 (m, 1H), 7.32 (dd, J=7.3, 1.0 Hz, 1H), 7.17 (m, 1H), 7.13 (s, 1H), 7.06-7.12 (m, 1H), 6.95 (dd, J=7.3, 6.6 Hz, 1H), 6.68 (d, J=7.6 Hz, 1H), 3.87 (t, J=7.1 Hz, 2H), 3.74-3.84 (m, 1H), 2.73-2.88 (m, 2H), 2.56-2.68 (m, 1H), 2.37-2.47 (m, 1H), 2.08-2.17 (m, 1H), 2.18 (s, 3H), 1.65-1.75 (m, 1H), 1.70 (sext, J=7.2 Hz, 2H), 0.83 (t, J=7.4 Hz, 3H). HPLC (Method 1): $R_t$=1.05 min.

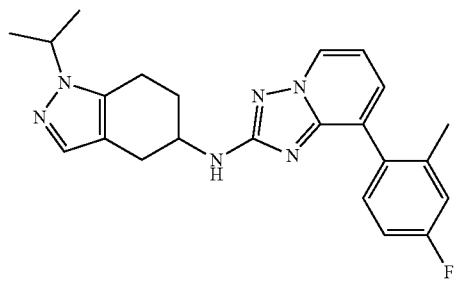

44

[8-(4-fluoro-2-methyl-phenyl)-[1,2,4]triazolo[1,5-a]pyridine-2-yl]-(1-isopropyl-4,5,6,7-tetrahydro-1H-indazol-5-yl)-amine (44). Prepared according to general procedure C-1 using triazolo pyridine 37b and amine 13d. Yield: 28 mg (45%). LCMS (ESI$^+$) calculated for $C_{23}H_{25}FN_6$ [M+H]$^+$ m/z 405.2203, found 405.3. $^1$H NMR (400 MHz, (CD$_3$)$_2$SO) δ 8.62 (dd, J=6.6, 1.0 Hz, 1H), 7.30-7.36 (m, 1H), 7.32 (dd, J=7.3, 1.0 Hz, 1H), 7.17 (m, 1H), 7.13 (s, 1H), 7.06-7.12 (m, 1H), 6.95 (dd, J=7.3, 6.6 Hz, 1H), 6.68 (d, J=7.5 Hz, 1H), 4.35 (sept, J=6.6 Hz, 1H), 3.75-3.86 (m, 1H), 2.74-2.87 (m, 2H), 2.58-2.69 (m, 1H), 2.37-2.46 (m, 1H), 2.18 (s, 3H), 2.08-2.17 (m, 1H), 1.70-1.82 (m, 1H), 1.34 (d, J=6.6 Hz, 3H), 1.32 (d, J=6.6 Hz, 3H). HPLC (Method 1): $R_t$=1.04 min.

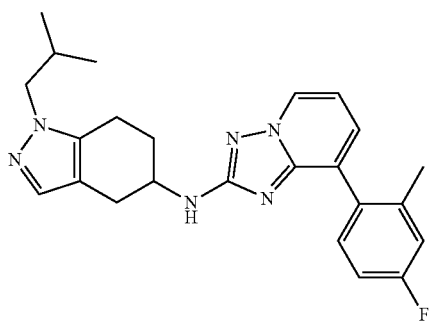

[8-(4-fluoro-2-methyl-phenyl)-[1,2,4]triazolo[1,5-a]pyridine-2-yl]-(1-isobutyl-4,5,6,7-tetrahydro-1H-indazol-5-yl)-amine (45). Prepared according to general procedure C-1 using triazolo pyridine 37b and amine 13e. Yield: 27 mg (42%). LCMS (ESI$^+$) calculated for $C_{25}H_{29}FN_6$ [M+H]$^+$ m/z 433.2516, found 419.3. $^1$H NMR (400 MHz, (CD$_3$)$_2$SO) δ 8.63 (dd, J=6.7, 1.2 Hz, 1H), 7.30-7.36 (m, 1H), 7.32 (dd, J=7.3, 1.2 Hz, 1H), 7.17 (m, 1H), 7.14 (s, 1H), 7.09 (m, 1H), 6.95 (dd, J=7.3, 6.7 Hz, 1H), 6.67 (d, J=7.5 Hz, 1H), 3.75-3.85 (m, 1H), 3.72 (d, J=7.2 Hz, 2H), 2.81-2.89 (m, 1H), 2.71-2.81 (m, 1H), 2.55-2.65 (m, 1H), 2.37-2.47 (m, 1H), 2.18 (s, 3H), 2.00-2.16 (m, 2H), 1.68-1.81 (m, 1H), 0.83 (d, J=6.8 Hz, 6H). HPLC (Method 12): R$_t$=0.85 min.

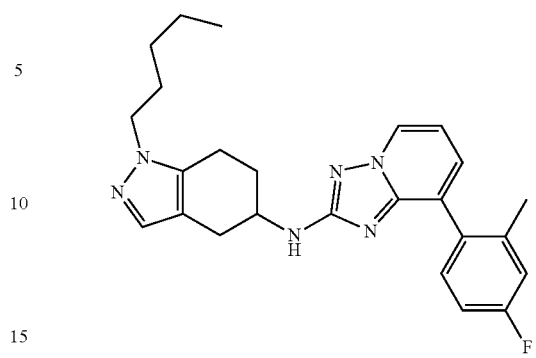

[8-(4-fluoro-2-methyl-phenyl)-[1,2,4]triazolo[1,5-a]pyridine-2-yl]-(1-pentyl-4,5,6,7-tetrahydro-1H-indazol-5-yl)-amine (47). Prepared according to general procedure C-2 using triazolo pyridine 37b and amine 13 g. Yield: 101 mg (71%). LCMS (ESI$^+$) calculated for $C_{24}H_{27}FN_6$ [M+H]$^+$ m/z 433.25160, found 433.3. $^1$H NMR (400 MHz, (CD$_3$)$_2$SO) δ 8.64 (dd, J=6.6, 1.2 Hz, 1H), 7.35 (dd, J=7.2, 1.2 Hz, 1H), 7.31-7.37 (m, 1H), 7.15-7.20 (m, 1H), 7.17 (s, 1H), 7.06-7.12 (m, 1H), 6.97 (dd, J=7.2, 6.6 Hz, 1H), 6.71 (br s, 1H, poor integration), 3.92 (t, J=7.1 Hz, 2H, partially obscured by water signal), 2.81-2.88 (m, 1H), 2.73-2.81 (m, 1H), 2.57-2.68 (m, 1H), 2.39-2.47 (m, 1H), 2.18 (s, 3H), 2.08-2.17 m, 1H), 2.73-2.83 (m, 1H), 1.64-1.73 (m, 2H), 1.17-1.35 (m, 4H), 0.85 (t, J=7.2 Hz, 3H). HPLC (Method 11): R$_t$=0.86 min.

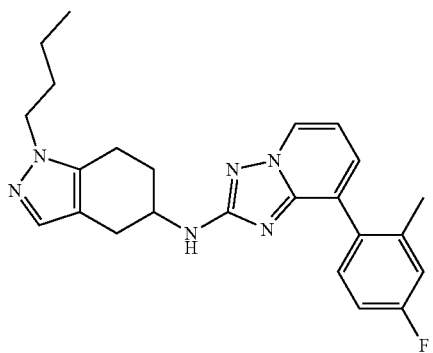

[8-(4-fluoro-2-methyl-phenyl)-[1,2,4]triazolo[1,5-a]pyridine-2-yl]-(1-butyl-4,5,6,7-tetrahydro-1H-indazol-5-yl)-amine (46). Prepared according to general procedure C-2 using triazolo pyridine 37b and amine 13f. Yield: 109 mg (80%). LCMS (ESI$^+$) calculated for $C_{24}H_{27}FN_6$ [M+H]$^+$ m/z 419.2359, found 419.2. $^1$H NMR (400 MHz, (CD$_3$)$_2$SO) δ 8.64 (dd, J=6.6, 1.1 Hz, 1H), 7.32-7.37 (m, 2H), 7.17 (m, 1H), 7.17 (s, 1H), 7.06-7.12 (m, 1H), 6.98 (dd, J=7.2, 6.6 Hz, 1H), 6.72 (br s, 1H, poor integration), 3.93 (t, J=7.1 Hz, 2H), 3.76-3.86 (m, 1H), 2.73-2.88 (m, 2H), 2.57-2.68 (m, 1H), 2.39-2.47 (m, 1H), 2.18 (s, 3H), 2.08-2.18 (m, 1H), 1.72-1.83 (m, 1H), 1.62-1.72 (m, 1H), 1.20-1.30 (m, 2H), 0.88 (t, J=7.3 Hz, 3H). HPLC (Method 11): R$_t$=0.80 min.

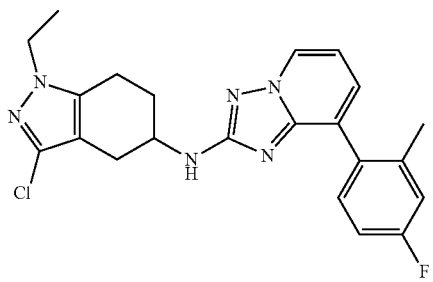

(3-Chloro-1-ethyl-4,5,6,7-tetrahydro-1H-indazol-5-yl)-[8-(4-fluoro-2-methyl-phenyl)-[1,2,4]triazolo[1,5-a]pyridine-2-yl]-amine (48). Prepared according to general procedure C-1 using triazolo pyridine 37b and amine 13b (1 equiv). Yield: 16 mg (15%). LCMS (ESI$^+$) calculated for $C_{22}H_{22}ClFN_6$ [M+H]$^+$ m/z 425.1657, found 425.2. $^1$H NMR (400 MHz, (CD$_3$)$_2$SO) δ 8.64 (dd, J=6.6, 1.0 Hz, 1H), 7.31-7.36 (m, 2H), 7.17 (m, 1H), 7.05-7.12 (m, 1H), 6.96 (dd, J=7.4, 6.6 Hz, 1H), 6.75 (d, J=7.5 Hz, 1H), 3.94 (q, J=7.2 Hz, 2H), 3.80-3.90 (m, 1H), 2.70-2.84 (m, 2H), 2.58-2.70 (m, 1H), 2.31-2.39 (m, 1H), 2.18 (s, 3H), 2.05-2.13 (m, 1H), 1.73-1.85 (m, 1H), 1.27 (t, J=7.2 Hz, 3H). HPLC (Method 1): R$_t$=1.09 min.

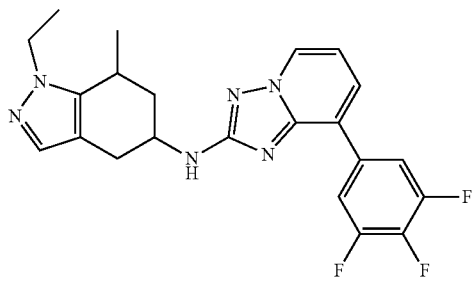

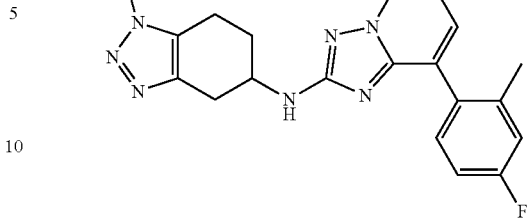

(1-Ethyl-7-methyl-4,5,6,7-tetrahydro-1H-indazol-5-yl)-[8-(3,4,5-trifluoro-phenyl)-[1,2,4]triazolo[1,5-a]pyridine-2-yl]-amine (49). Prepared according to general procedure C-2 using triazolo pyridine 37c and amine 17 (1 equiv) by heating at 160° C. for 6 h under microwave irradation. Yield: 18 mg (9%). LCMS (ESI$^+$) calculated for $C_{22}H_{21}F_3N_6$ [M+H]$^+$ m/z 427.1858, found 427.1. $^1$H NMR (400 MHz, (CD$_3$)$_2$SO) δ 8.67 (m, 1H), 8.23-8.32 (m, 2H), 7.92 (m, 1H), 7.16 (s, 1H), 6.95-7.03 (m, 2H), 4.07 (q, J=7.2 Hz, 1H), 4.06 (q, J=7.2 Hz, 1H), 3.68-3.79 (m, 1H), 3.02-3.11 (m, 1H), 2.87-2.95 (m, 1H), 2.29-2.43 (m, 2H), 1.43-1.53 (m, 1H), 1.33 (t, J=7.2 Hz, 3H), 1.28 (d, J=6.7 Hz, 3H). Note: Only the major cis diastereomer was assigned. HPLC (Method 4): R$_t$=1.25 min.

(1-Ethyl-4,5,6,7-tetrahydro-1H-benzotriazol-5-yl)-[8-(4-fluoro-2-methyl-phenyl)-[1,2,4]triazolo[1,5-a]pyridine-2-yl]-amine (51). Prepared according to general procedure C-1 using triazolo pyridine 37b and amine 24 (1 equiv). Yield: 90 mg (59%). LCMS (ESI$^+$) calculated for $C_{21}H_{22}FN_7$ [M+H]$^+$ m/z 392.1999, found 392.1. $^1$H NMR (400 MHz, (CD$_3$)$_2$SO) δ 8.65 (dd, J=6.7, 1.0 Hz, 1H), 7.30-7.37 (m, 2H), 7.17 (m, 1H), 7.09 (m, 1H), 6.98 (dd, J=7.3, 6.7 Hz, 1H), 6.80 (br s, 1H), 4.22 (q, J=7.3 Hz, 2H), 3.90-3.98 (m, 1H), 2.97-3.06 (m, 1H), 2.78-2.88 (m, 1H), 2.61-2.74 (m, 2H), 2.18 (s, 3H), 2.07-2.16 (m, 1H), 1.79-1.91 (m, 1H), 1.37 (t, J=7.3 Hz, 3H). HPLC (Method 7): R$_t$=0.50 min.

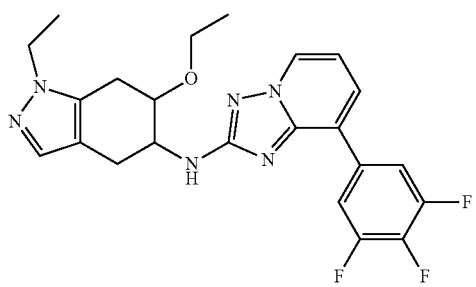

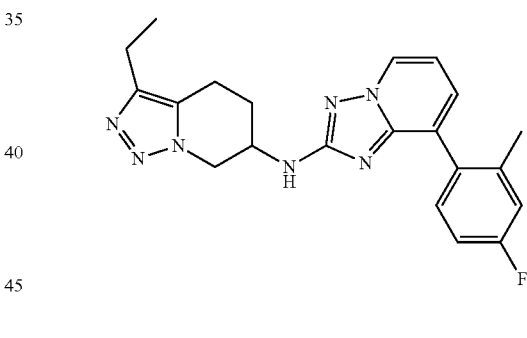

(6-Ethoxy-1-ethyl-4,5,6,7-tetrahydro-1H-indazol-5-yl)-[8-(3,4,5-trifluoro-phenyl)-[1,2,4]triazolo[1,5-a]pyridine-2-yl]-amine (50). Prepared according to general procedure C-1 using triazolo pyridine 37c and amine 13 h (1 equiv). Yield: 11 mg (17%). LCMS (ESI$^+$) calculated for $C_{23}H_{22}F_3N_6O$ [M+H]$^+$ m/z 457.1964, found 457.2. $^1$H NMR (400 MHz, (CD$_3$)$_2$SO) δ 8.68 (dd, J=6.7, 0.9 Hz, 1H), 8.23-8.32 (m, 2H), 7.92 (dd, J=7.5, 0.9 Hz, 1H), 7.14 (s, 1H), 7.01 (dd, J=7.5, 6.7 Hz, 1H), 6.70 (d, J=7.7 Hz, 1H), 4.02-4.09 (m, 2H), 3.98 (q, J=7.4 Hz, 2H), 3.48-3.63 (m, 2H), 2.93-3.03 (m, 1H), 2.79-2.89 (m, 1H), 2.70 (m, 2H), 1.29 (t, J=7.3 Hz, 3H), 1.07 (t, J=7.1 Hz, 3H). Note: Only the major diastereomer was assigned. HPLC (Method 3): R$_t$=0.70 min.

(3-Ethyl-4,5,6,7-tetrahydro-[1,2,3]triazolo[1,5-a]pyridine-6-yl)-[8-(4-fluoro-2-methyl-phenyl)-[1,2,4]triazolo[1,5-a]pyridine-2-yl]-amine (52). Prepared according to general procedure C-2 using triazolo pyridine 37b and amine 32 (1 equiv) by heating at 160° C. for 3 h under microwave irradiation. Yield: 9 mg, TFA salt (16%). LCMS (ESI$^+$) calculated for $C_{21}H_{22}FN_7$ [M+H]$^+$ m/z 392.1999, found 392.1. $^1$H NMR (400 MHz, (CD$_3$)$_2$SO) δ 8.68 (dd, J=6.7, 1.0 Hz, 1H), 7.37 (dd, J=7.3, 1.0 Hz, 1H), 7.32-7.36 (m, 1H), 7.17 (m, 1H), 7.09 (m, 1H), 7.00 (dd, J=7.3, 6.7 Hz, 1H), 4.53 (dd, J=12.2, 4.3 Hz, 1H), 4.32 (dd, J=12.6, 6.2 Hz, 1H), 4.12-4.20 (m, 1H), 2.89-2.99 (m, 1H), 2.71-2.81 (m, 1H), 2.55 (q, J=7.7 Hz, 2H), 2.18 (s, 3H), 2.06-2.15 (m, 1H), 1.95-2.05 (m, 1H), 1.16 (t, J=7.7 Hz, 3H). HPLC (Method 3): R$_t$=0.59 min.

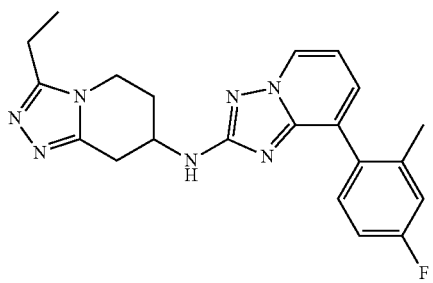

53

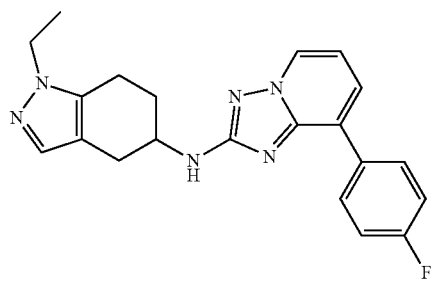

55

(3-Ethyl-5,6,7,8-tetrahydro-[1,2,4]triazolo[4,3-a]pyridine-7-yl)-[8-(4-fluoro-2-methyl-phenyl)-[1,2,4]triazolo[1,5-a]pyridine-2-yl]-amine (53). Prepared according to general procedure C-1 using triazolo pyridine 37b and amine 28 (1 equiv). Yield: 15 mg (26%). LCMS (ESI$^+$) calculated for $C_{21}H_{22}FN_7$ [M+H]$^+$ m/z 392.1999, found 392.3. $^1$H NMR (400 MHz, (CD$_3$)$_2$SO) δ 8.66 (dd, J=6.6, 1.1 Hz, 1H), 7.35 (dd, J=7.3, 1.1 Hz, 1H), 7.32-7.37 (m, 1H), 7.17 (m, 1H), 7.09 (m, 1H), 6.98 (dd, J=7.3, 6.7 Hz, 1H), 6.91 (d, J=6.8 Hz, 1H), 3.98-4.11 (m, 2H), 3.84-3.93 (m, 1H), 3.15 (dd, J=16.4, 5.0 Hz, 1H), 2.87 (dd, J=16.4, 7.5 Hz, 1H), 2.63 (q, J=7.5 Hz, 2H), 2.18-2.27 (m, 1H), 2.18 (s, 3H), 1.97-2.09 (m, 1H), 1.22 (t, J=7.5 Hz, 3H). HPLC (Method 6): R$_t$=0.46 min.

(1-Ethyl-4,5,6,7-tetrahydro-1H-indazol-5-yl)-[8-(4-fluoro-phenyl)-[1,2,4]triazolo[1,5-a]pyridine-2-yl]-amine (55). Prepared according to general procedure C-2 using triazolo pyridine 37a and amine 13a (1 equiv) by heating at 120-160° C. for 9 h under microwave irradiation. Yield: 115 mg (obtained as TFA salt, 69%). LCMS (ESI$^+$) calculated for $C_{21}H_{21}FN_6$ [M+H]$^+$ m/z 377.1890, found 377.2. $^1$H NMR (400 MHz, (CD$_3$)$_2$SO) δ 8.62 (dd, J=6.6, 1.1 Hz, 1H), 8.14-8.20 (m, 2H), 7.73 (dd, J=7.4, 1.1 Hz, 1H), 7.29-7.36 (m, 2H), 7.22 (s, 1H), 6.99 (dd, J=7.4, 6.6 Hz, 1H), 3.99 (q, J=7.3 Hz, 2H), 3.85-3.93 (m, 1H), 2.77-2.93 (m, 2H), 2.62-2.73 (m, 1H), 2.45-2.52 (m, 1H, largely obscured by DMSO signal), 2.13-2.22 (m, 1H), 1.76-1.88 (m, 1H), 1.30 (t, J=7.3 Hz, 3H). HPLC (Method 5): R$_t$=0.61 min.

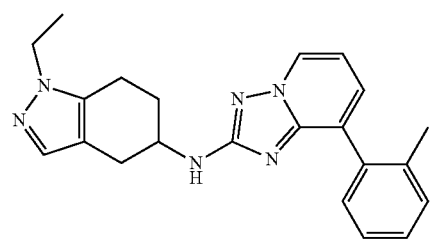

56

(1-Ethyl-4,5,6,7-tetrahydro-1H-indazol-5-yl)-[8-(2-methyl-phenyl)-[1,2,4]triazolo[1,5-a]pyridine-2-yl]-amine (56). Prepared according to general procedure D-1 using triazolo pyridine 39b and 2-methyl-phenylboronic acid (1.5 equiv) by heating at 80° C. for 3 h in toluene. Yield: 22 mg (59%). LCMS (ESI$^+$) calculated for $C_{22}H_{24}N_6$ [M+H]$^+$ m/z 373.2141, found 373.2. $^1$H NMR (400 MHz, (CD$_3$)$_2$SO) δ 8.64 (dd, J=6.6, 1.1 Hz, 1H), 7.35 (dd, J=7.3, 1.1 Hz, 1H), 7.23-7.33 (m, 4H), 7.16 (s, 1H), 6.98 (dd, J=7.3, 6.6 Hz, 1H), 6.69 (br s, 1H), 3.96 (q, J=7.2 Hz, 2H), 3.77-3.86 (m, 1H), 2.73-2.87 (m, 2H), 2.58-2.69 (m, 1H), 2.39-2.47 (m, 1H), 2.17 (s, 3H), 2.08-2.17 (m, 1H), 1.71-1.83 (m, 1H), 1.27 (t, J=7.2 Hz, 3H). HPLC (Method 2): R$_t$=0.89 min.

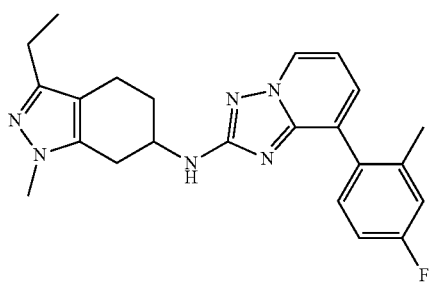

54

(3-Ethyl-1-methyl-4,5,6,7-tetrahydro-1H-indazol-6-yl)-[8-(4-fluoro-2-methyl-phenyl)-[1,2,4]triazolo[1,5-a]pyridine-2-yl]-amine (54). Prepared according to general procedure C-1 using triazolo pyridine 37b and amine 21a (1 equiv). Yield: 77 mg (58%). LCMS (ESI$^+$) calculated for $C_{23}H_{25}FN_6$ [M+H]$^+$ m/z 405.2203, found 405.3. $^1$H NMR (400 MHz, (CD$_3$)$_2$SO) δ 8.65 (dd, J=6.7, 1.2 Hz, 1H), 7.35 (dd, J=7.2, 1.2 Hz, 1H), 7.32-7.37 (m, 1H), 7.18 (m, 1H), 6.97 (dd, J=7.2, 6.7 Hz, 1H), 6.78 (br, 1H), 3.84-3.94 (m, 1H, largely obscured by water signal), 3.58 (s, 3H), 2.96-3.05 (m, 1H), 2.35-2.57 (m, 3H, partially obscured by DMSO signal), 2.45 (q, J=7.6 Hz, 2H), 2.19 (s, 3H), 1.96-2.05 (m, 1H), 1.65-1.76 (m, 1H), 1.15 (t, J=7.6 Hz, 3H). HPLC (Method 1): R$_t$=1.04 min.

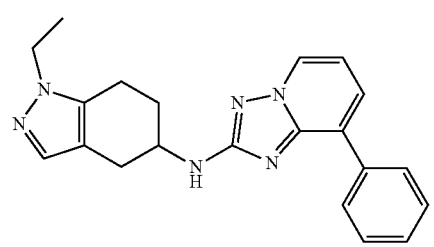

57

(1-Ethyl-4,5,6,7-tetrahydro-1H-indazol-5-yl)-(8-phenyl-[1,2,4]triazolo[1,5-a]pyridine-2-yl)-amine (57). Prepared according to general procedure D-1 using halo triazolo pyridine 39b and phenylboronic acid. Yield: 26 mg (72%). LCMS (ESI$^+$) calculated for $C_{21}H_{22}N_6$ [M+H]$^+$ m/z 359.1984, found 359.2. $^1$H NMR (400 MHz, (CD$_3$)$_2$SO) δ 8.64 (dd, J=6.6, 1.0 Hz, 1H), 8.09-8.13 (m, 2H), 7.74 (dd, J=7.5, 1.0 Hz, 1H), 7.47-7.53 (m, 2H), 7.38-7.44 (m, 1H), 7.16 (s, 1H), 7.00 (dd, J=7.5, 6.6 Hz, 1H), 6.85 (d, J=7.5 Hz, 1H), 3.98 (q, J=7.2 Hz, 2H), 3.82-3.92 (m, 1H), 2.77-2.93 (m, 2H), 2.60-2.72 (m, 1H), 2.43-2.51 (m, 1H, partially obscured by DMSO signal), 2.13-2.23 (m, 1H), 1.73-1.87 (m, 1H), 1.29 (t, J=7.2 Hz, 3H). HPLC (Method 9): R$_t$=0.64 min.

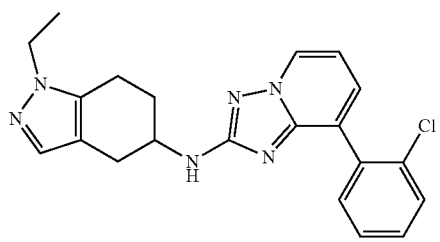

58

[8-(2-Chloro-phenyl)-[1,2,4]triazolo[1,5-a]pyridine-2-yl]-(1-ethyl-4,5,6,7-tetrahydro-1H-indazol-5-yl)-amine (58). Prepared according to general procedure D-1 using halo triazolo pyridine 39b and 2-chloro-phenylboronic acid. Yield: 12 mg (30%). LCMS (ESI$^+$) calculated for $C_{21}H_{21}ClN_6$ [M+H]$^+$ m/z 393.1594, found 393.2. $^1$H NMR (400 MHz, (CD$_3$)$_2$SO) δ 8.66 (dd, J=6.6, 1.1 Hz, 1H), 7.56-7.60 (m, 1H), 7.55-7.51 (m, 1H), 7.41-7.47 (m, 2H), 7.41 (dd, J=7.3, 1.1 Hz, 1H), 7.12 (s, 1H), 6.97 (dd, J=7.3, 6.7 Hz, 1H), 6.70 (d, J=7.4 Hz, 1H), 3.95 (q, J=7.2 Hz, 2H), 3.75-3.85 (m, 1H), 2.73-2.88 (m, 2H), 2.58-2.69 (m, 1H), 2.38-2.47 (m, 1H), 2.08-2.18 (m, 1H), 1.70-1.83 (m, 1H), 1.27 (t, J=7.2 Hz, 3H). HPLC (Method 8): R$_t$=0.83 min.

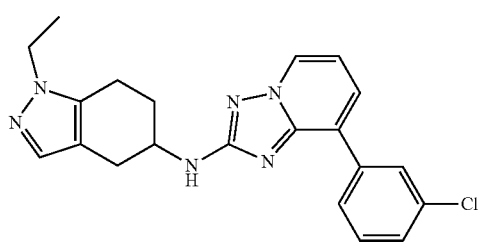

59

[8-(3-Chloro-phenyl)-[1,2,4]triazolo[1,5-a]pyridine-2-yl]-(1-ethyl-4,5,6,7-tetrahydro-1H-indazol-5-yl)-amine (59). Prepared according to general procedure D-1 using halo triazolo pyridine 39b and 3-chloro-phenylboronic acid. Yield: 21 mg (53%). LCMS (ESI$^+$) calculated for $C_{21}H_{21}ClN_6$ [M+H]$^+$ m/z 393.1594, found 393.3. $^1$H NMR (400 MHz, (CD$_3$)$_2$SO) δ 8.68 (d, J=6.7, 0.9 Hz, 1H), 8.31 (m, 1H), 8.06 (m, 1H), 7.83 (dd, J=7.5, 0.9 Hz, 1H), 7.54 (m, 1H), 7.46-7.50 (m, 1H), 7.15 (s, 1H), 7.00 (t, J=7.5, 6.7 Hz, 1H), 6.93 (d, J=7.4 Hz, 1H), 3.97 (q, J=7.1 Hz, 2H), 3.80-3.91 (m, 1H), 2.76-2.93 (m, 2H), 2.60-2.71 (m, 1H), 2.43-2.50 (m, 1H), 2.14-2.23 (m, 1H), 1.73-1.86 (m, 1H), 1.28 (t, J=7.1 Hz, 3H). HPLC (Method 9): R$_t$=0.75 min.

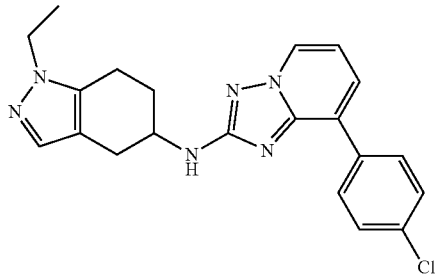

60

[8-(4-Chloro-phenyl)-[1,2,4]triazolo[1,5-a]pyridine-2-yl]-(1-ethyl-4,5,6,7-tetrahydro-1H-indazol-5-yl)-amine (60). Prepared according to general procedure D-1 using halo triazolo pyridine 39b and 4-chloro-phenylboronic acid. Yield: 16 mg (41%). LCMS (ESI$^+$) calculated for $C_{21}H_{21}ClN_6$ [M+H]$^+$ m/z 393.1594, found 393.3. $^1$H NMR (400 MHz, (CD$_3$)$_2$SO) δ 8.65 (dd, J=6.6, 1.0 Hz, 1H), 8.16-8.20 (m, 2H), 7.78 (dd, J=7.5, 1.0 Hz, 1H), 7.54-7.58 (m, 2H), 7.15 (s, 1H), 7.00 (dd, J=7.5, 6.6 Hz, 1H), 6.89 (d, J=7.6 Hz, 1H), 3.97 (q, J=7.3 Hz, 2H), 3.81-3.92 (m, 1H), 2.76-2.91 (m, 2H), 2.61-2.72 (m, 1H), 2.42-2.49 (m, 1H), 2.13-2.22 (m, 1H), 1.72-1.84 (m, 1H), 1.28 (t, J=7.3 Hz, 3H). HPLC (Method 9): R$_t$=0.75 min.

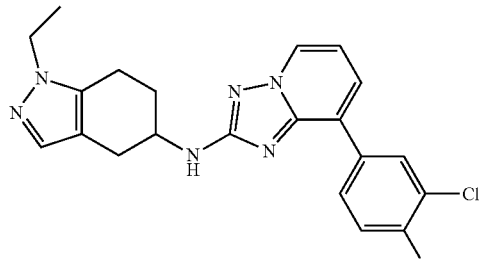

61

[8-(3-Chloro-4-fluoro-phenyl)-[1,2,4]triazolo[1,5-a]pyridine-2-yl]-(1-ethyl-4,5,6,7-tetrahydro-1H-indazol-5-yl)-amine (61). Prepared according to general procedure D-1 using halo triazolo pyridine 39b and 3-chloro-4-fluoro-phenylboronic acid. Yield: 16 mg (38%). LCMS (ESI$^+$) calculated for $C_{21}H_{20}ClFN_6$ [M+H]$^+$ m/z 411.1500, found 411.2. $^1$H NMR (400 MHz, (CD$_3$)$_2$SO) δ 8.65 (dd, J=6.6, 1.0 Hz, 1H), 8.48 (dd, J=7.4, 2.3 Hz, 1H), 8.14 (m, 1H), 7.82 (dd, J=7.5, 1.0 Hz, 1H), 7.55 (m, 1H), 7.15 (s, 1H), 6.99 (dd, J=7.5, 6.6 Hz, 1H), 6.88 (d, J=7.5 Hz, 1H), 3.97 (q, J=7.2 Hz, 2H), 3.81-3.91 (m, 1H), 2.85-2.93 (m, 1H), 2.76-2.85 (m, 1H), 2.60-2.71 (m, 1H), 2.44-2.52 (m, 1H, partially obscured by DMSO signal), 2.14-2.23 (m, 1H), 1.75-1.86 (m, 1H), 1.29 (t, J=7.2 Hz, 3H). HPLC (Method 8): R$_t$=0.94 min.

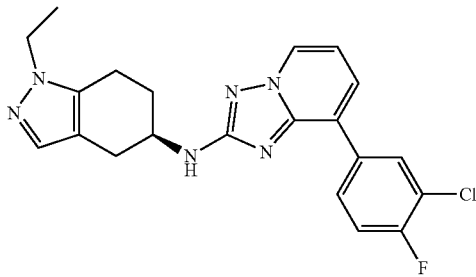

R-61

(R)-[8-(3-Chloro-4-fluoro-phenyl)-[1,2,4]triazolo[1,5-a]pyridine-2-yl]-(1-ethyl-4,5,6,7-tetrahydro-1H-indazol-5-yl)-amine (R-61). Prepared according to general procedure D-2 using chiral halo triazolo pyridine R-39a and 3-chloro-4-fluoro-phenylboronic acid. Yield: 232 mg (57%). HRMS (ESI$^+$) calculated for $C_{21}H_{20}ClFN_6$ [M+H]$^+$ m/z 411.1500, found 411.1500. $^1$H NMR (400 MHz, (CD$_3$)$_2$SO) δ 8.65 (dd, J=6.6, 1.0 Hz, 1H), 8.48 (dd, J=7.4, 2.3 Hz, 1H), 8.14 (m, 1H), 7.82 (dd, J=7.5, 1.0 Hz, 1H), 7.55 (m, 1H), 7.15 (s, 1H), 6.99 (dd, J=7.5, 6.6 Hz, 1H), 6.88 (d, J=7.5 Hz, 1H), 3.97 (q, J=7.2 Hz, 2H), 3.81-3.91 (m, 1H), 2.85-2.93 (m, 1H), 2.76-2.85 (m, 1H), 2.60-2.71 (m, 1H), 2.44-2.52 (m, 1H, partially obscured by DMSO signal), 2.14-2.23 (m, 1H), 1.75-1.86 (m, 1H), 1.29 (t, J=7.2 Hz, 3H). HPLC (Method 4): R$_t$=1.22 min. Enantiomeric purity (method 14): 97.4% ee. Specific optical rotation: [α]$^{20}{_D}$=+6.5° (c 0.4 mg/mL, MeOH).

Crystal Data of Compound R-61

Single crystals of compound R-61 (C$_{21}$H$_{20}$ClFN$_6$*0.5 CH$_3$OH) were grown in methanol. A suitable crystal was coated with Paratone N oil, suspended in a small fiber loop and placed in a cooled N$_2$ gas stream at 100 K on a Rigaku AFC11R Cu Kα (1.5418 Å) diffractometer. The crystal was kept at 100 K during data collection. Using Olex2 (Dolomanov, O. V., Bourhis, L. J., Gildea, R. J, Howard, J. A. K. & Puschmann, H. *J. Appl. Cryst.* 2009, 42, 339-341), the structure was solved with the SheIXT (Sheldrick, G. M. *Acta Cryst.* 2015, A71, 3-8) structure solution program using Direct Methods and refined with the SheIXL (Sheldrick, G. M. *Acta Cryst.* 2008, A64, 112-122) refinement package using Least Squares minimization. CCDC [1578256] contains the supplementary crystallographic data for this paper. These data can be obtained free of charge from The Cambridge Crystallographic Data Centre via www.ccdc.cam.ac.uk/data_request/cif. Additional details of data collection and structure refinement are given in Tables 3, 3a-3e.

TABLE 3

Data collection and structure refinement details of crystal structure of compound R-61.

| | |
|---|---|
| Identification code | CCDC [1578256] |
| Empirical formula | C$_{21.5}$H$_{22}$ClFN$_6$O$_{0.5}$ |
| Formula weight | 426.90 |
| Temperature/K | 100.15 |
| Crystal system | monoclinic |
| Space group | P21 |
| a/Å | 7.10926(16) |
| b/Å | 15.4984(2) |
| c/Å | 18.5987(3) |
| α/° | 90 |
| β/° | 94.4689(19) |
| γ/° | 90 |
| Volume/Å3 | 2043.01(6) |

TABLE 3-continued

Data collection and structure refinement details of crystal structure of compound R-61.

| | |
|---|---|
| Z | 4 |
| ρcalcg/cm3 | 1.388 |
| μ/mm 1 | 1.933 |
| F(000) | 892.0 |
| Radiation | CuKα (λ = 1.54184) |
| 2Θ range for data collection/° | 7.434 to 129.036 |
| Index ranges | −8 ≤ h ≤ 8, −17 ≤ k ≤ 18, −21 ≤ l ≤ 21 |
| Reflections collected | 43736 |
| Independent reflections | 6072 [Rint = 0.0775, Rsigma = 0.0339] |
| Data/restraints/parameters | 6072/1/546 |
| Goodness-of-fit on F2 | 1.113 |
| Final R indexes [I >= 2σ (I)] | R1 = 0.0845, wR2 = 0.2256 |
| Final R indexes [all data] | R1 = 0.0863, wR2 = 0.2317 |
| Largest diff. peak/hole/e Å-3 | 0.71/−0.63 |
| Flack parameter | 0.02(3) |

TABLE 3a

Fractional Atomic Coordinates (×10$^4$) and Equivalent Isotropic Displacement Parameters (Å$^2$ × 10$^3$) for data. U$_{eq}$ is defined as 1/3 of the trace of the orthogonalised U$_{IJ}$ tensor.

| Atom | x | y | z | U(eq) |
|---|---|---|---|---|
| Cl10 | 9873(2) | 5287.4(10) | 1486.3(9) | 42.8(5) |
| Cl1 | 2907(3) | 3836.5(10) | 3404.6(10) | 47.8(6) |
| F101 | 5779(6) | 5532(2) | 1311(2) | 40.4(10) |
| O201 | −9025(7) | 11861(3) | 4730(3) | 43.1(12) |
| F1 | 7006(7) | 3742(3) | 3728(3) | 53.2(12) |
| N6 | 2475(8) | 8169(4) | 2625(3) | 31.4(12) |
| N102 | 15899(8) | −2077(4) | −78(3) | 33.2(12) |
| N105 | 11469(8) | 638(4) | 1782(3) | 32.0(12) |
| N106 | 9895(8) | v930(3) | 2102(3) | 30.1(12) |
| N104 | 10796(8) | 2052(4) | 1473(3) | 30.2(11) |
| N101 | 17263(8) | −1483(4) | 72(3) | 32.2(12) |
| N103 | 13417(8) | 1365(3) | 1002(3) | 31.0(12) |
| N4 | 1747(8) | 7122(4) | 3363(3) | 31.8(12) |
| N5 | 947(8) | 8486(4) | 2949(3) | 32.0(12) |
| N3 | −775(8) | 7858(4) | 3858(3) | 36.4(13) |
| N2 | −4726(8) | 10648(4) | 4840(3) | 35.3(13) |
| N1 | −6499(9) | 10542(4) | 4508(4) | 46.0(15) |
| C102 | 14597(9) | −797(4) | 207(3) | 30.3(13) |
| C11 | 2936(9) | 7361(4) | 2874(3) | 30.3(14) |
| C103 | 13329(9) | −70(4) | 400(3) | 31.3(14) |
| C101 | 14292(9) | −1657(4) | 2(3) | 31.1(14) |
| C118 | 4900(10) | 4118(4) | 1627(3) | 33.0(14) |
| C116 | 7327(10) | 3053(4) | 1937(3) | 32.5(14) |
| C10 | 625(9) | 7820(4) | 3399(3) | 29.7(13) |
| C117 | 5421(10) | 3291(4) | 1830(3) | 34.1(15) |
| C110 | 11913(9) | 1349(4) | 1409(3) | 30.3(14) |
| C111 | 9496(9) | 1766(4) | 1910(3) | 30.2(13) |
| C16 | 5196(10) | 6107(4) | 2922(3) | 31.7(14) |
| C12 | 4575(10) | 6953(4) | 2634(3) | 32.8(15) |
| C112 | 7839(10) | 2167(4) | 2146(3) | 32.5(14) |
| C13 | 5545(10) | 7409(5) | 2141(4) | 36.6(15) |
| C7 | −3571(10) | 9993(4) | 4685(3) | 33.2(14) |
| C104 | 14475(9) | 593(4) | 857(3) | 30.8(14) |
| C4 | −1620(10) | 8685(4) | 4040(4) | 34.1(15) |
| C14 | 5018(10) | 8229(5) | 1906(4) | 37.0(15) |
| C2 | −4609(10) | 9427(4) | 4242(4) | 35.8(15) |
| C15 | 3467(10) | 8626(4) | 2144(3) | 35.2(15) |
| C107 | 16554(9) | −700(4) | 248(3) | 31.4(14) |
| C106 | 17635(10) | 92(4) | 461(4) | 35.7(15) |
| C17 | 7110(10) | 5936(5) | 3089(3) | 36.8(15) |
| C5 | −920(11) | 8975(4) | 4800(4) | 42.0(16) |
| C119 | 6270(10) | 4729(4) | 1516(3) | 34.7(15) |
| C115 | 8804(10) | 427(5) | 2506(3) | 34.4(15) |
| C114 | 7226(10) | 800(5) | 2743(4) | 37.7(15) |
| C108 | 19250(10) | −1754(4) | 132(4) | 35.3(15) |
| C105 | 16274(10) | 857(4) | 492(4) | 35.3(15) |
| C19 | 6416(11) | 4523(5) | 3468(4) | 40.4(17) |
| C21 | 3901(10) | 5459(5) | 3040(3) | 35.0(15) |
| C121 | 8696(10) | 3687(4) | 1820(3) | 33.2(14) |
| C113 | 6754(10) | 1655(5) | 2566(4) | 36.7(15) |

TABLE 3a-continued

Fractional Atomic Coordinates (×10$^4$) and Equivalent Isotropic Displacement Parameters (Å$^2$ × 10$^3$) for data. U$_{eq}$ is defined as 1/3 of of the trace of the orthogonalised U$_{IJ}$ tensor.

| Atom | x | y | z | U(eq) |
|---|---|---|---|---|
| C120 | 8182(10) | 4508(4) | 1620(3) | 35.2(15) |
| C20 | 4498(11) | 4658(4) | 3300(4) | 37.8(16) |
| C6 | −1543(11) | 9907(5) | 4940(4) | 41.2(16) |
| C8 | −4269(11) | 11443(5) | 5220(4) | 39.5(16) |
| C201 | −9458(12) | 12058(6) | 3993(4) | 49.2(18) |
| C3 | −3774(10) | 8619(5) | 3954(4) | 41.6(17) |
| C18 | 7714(11) | 5148(5) | 3366(4) | 41.1(17) |
| C9 | −4005(11) | 12187(5) | 4709(4) | 41.1(16) |
| C1 | −6427(11) | 9797(5) | 4142(5) | 48.0(18) |
| C109 | 19744(12) | −2215(7) | 834(5) | 58(2) |

TABLE 3b

Anisotropic Displacement Parameters (Å$^2$ × 10$^3$) for data. The Anisotropic displacement factor exponent takes the form: $-2\pi^2[h^2a^{*2}U_{11} + 2hka^*b^*U_{12}+ \ldots]$.

| Atom | U$_{11}$ | U$_{22}$ | U$_{33}$ | U$_{23}$ | U$_{13}$ | U$_{12}$ |
|---|---|---|---|---|---|---|
| Cl10 | 45.5(10) | 25.9(9) | 56.7(10) | 2.9(7) | 2.9(8) | −1.1(7) |
| Cl1 | 54.6(12) | 28.0(9) | 62.1(11) | 5.9(7) | 11.4(9) | −1.8(8) |
| F101 | 52(2) | 25(2) | 44(2) | 1.3(15) | 0.3(17) | 11.8(17) |
| O201 | 41(3) | 32(3) | 56(3) | −8(2) | 1(2) | 7(2) |
| F1 | 63(3) | 35(3) | 61(3) | 16(2) | 3(2) | 17(2) |
| N6 | 36(3) | 21(3) | 39(3) | 2(2) | 5(2) | 1(2) |
| N102 | 31(3) | 26(3) | 42(3) | −2(2) | 0(2) | −2(2) |
| N105 | 33(3) | 26(3) | 38(3) | 1(2) | 3(2) | 3(2) |
| N106 | 33(3) | 22(3) | 35(2) | 0(2) | 2(2) | 1(2) |
| N104 | 28(3) | 22(3) | 41(3) | 1(2) | 3(2) | 0(2) |
| N101 | 31(3) | 22(3) | 44(3) | −4(2) | 5(2) | −1(2) |
| N103 | 29(3) | 19(3) | 45(3) | 2(2) | 3(2) | −1(2) |
| N4 | 29(3) | 24(3) | 42(3) | −1(2) | 2(2) | 2(2) |
| N5 | 33(3) | 22(3) | 41(3) | 3(2) | 3(2) | 4(2) |
| N3 | 39(3) | 24(3) | 47(3) | 6(2) | 12(2) | 4(2) |
| N2 | 35(3) | 28(3) | 42(3) | −3(2) | −2(2) | −1(2) |
| N1 | 34(3) | 34(3) | 70(4) | −16(3) | 3(3) | 1(3) |
| C102 | 33(3) | 21(3) | 36(3) | 0(2) | 1(2) | −2(3) |
| C11 | 33(3) | 20(3) | 37(3) | 1(2) | −1(3) | 0(3) |
| C103 | 33(3) | 24(3) | 37(3) | 2(2) | 1(3) | 4(3) |
| C101 | 28(3) | 27(3) | 38(3) | −2(2) | 2(3) | −5(3) |
| C118 | 31(3) | 32(3) | 35(3) | −3(3) | −3(2) | 7(3) |
| C116 | 36(4) | 25(3) | 37(3) | −2(2) | 1(3) | 4(3) |
| C10 | 30(3) | 19(3) | 39(3) | 1(2) | −4(3) | 3(3) |
| C117 | 38(4) | 29(3) | 36(3) | −4(3) | 2(3) | 0(3) |
| C110 | 33(3) | 19(3) | 38(3) | −3(2) | 1(3) | −2(2) |
| C111 | 30(3) | 25(3) | 35(3) | −1(2) | 0(3) | 4(3) |
| C16 | 38(4) | 25(3) | 33(3) | −2(2) | 1(3) | 3(3) |
| C12 | 40(4) | 25(3) | 34(3) | −2(3) | 2(3) | 2(3) |
| C112 | 32(3) | 26(3) | 39(3) | −1(3) | 2(3) | −1(3) |
| C13 | 40(4) | 30(4) | 40(3) | 0(3) | 5(3) | 1(3) |
| C7 | 39(4) | 21(3) | 39(3) | 3(3) | 3(3) | −1(3) |
| C104 | 30(3) | 22(3) | 40(3) | −1(2) | 1(3) | −1(2) |
| C4 | 35(4) | 20(3) | 47(3) | 6(3) | 6(3) | 6(3) |
| C14 | 39(4) | 31(4) | 41(3) | 4(3) | 0(3) | 2(3) |
| C2 | 35(4) | 23(3) | 50(3) | −4(3) | 4(3) | −1(3) |
| C15 | 39(4) | 26(3) | 41(3) | 5(3) | 4(3) | −1(3) |
| C107 | 31(3) | 26(3) | 37(3) | 2(3) | 4(3) | 1(3) |
| C106 | 31(3) | 27(4) | 49(3) | −2(3) | 4(3) | −1(3) |
| C17 | 43(4) | 28(4) | 39(3) | −1(3) | 3(3) | 4(3) |
| C5 | 43(4) | 29(4) | 52(4) | −1(3) | −9(3) | 5(3) |
| C119 | 41(4) | 25(3) | 37(3) | −4(3) | 0(3) | 9(3) |
| C115 | 38(4) | 28(4) | 37(3) | 3(3) | 3(3) | −1(3) |
| C114 | 40(4) | 33(4) | 40(3) | 1(3) | 6(3) | −3(3) |
| C108 | 32(3) | 27(4) | 46(3) | −3(3) | 2(3) | 2(3) |
| C105 | 38(4) | 25(3) | 43(3) | 0(3) | 5(3) | −1(3) |
| C19 | 51(4) | 28(4) | 42(3) | 6(3) | 0(3) | 16(3) |
| C21 | 37(4) | 32(4) | 36(3) | −8(3) | 2(3) | 4(3) |
| C121 | 35(4) | 28(4) | 36(3) | −1(3) | −1(3) | 6(3) |
| C113 | 36(4) | 31(4) | 43(3) | −2(3) | 6(3) | 1(3) |
| C120 | 45(4) | 25(3) | 35(3) | −2(3) | 5(3) | 0(3) |
| C20 | 48(4) | 27(4) | 39(3) | 1(3) | 6(3) | 4(3) |

TABLE 3b-continued

Anisotropic Displacement Parameters (Å$^2$ × 10$^3$) for data. The Anisotropic displacement factor exponent takes the form: $-2\pi^2[h^2a^{*2}U_{11} + 2hka^*b^*U_{12}+ \ldots]$.

| Atom | U$_{11}$ | U$_{22}$ | U$_{33}$ | U$_{23}$ | U$_{13}$ | U$_{12}$ |
|---|---|---|---|---|---|---|
| C6 | 48(4) | 25(4) | 49(4) | −3(3) | −8(3) | 2(3) |
| C8 | 50(4) | 22(3) | 46(4) | −3(3) | −1(3) | 1(3) |
| C201 | 46(4) | 39(4) | 62(4) | −10(4) | −1(4) | −2(3) |
| C3 | 37(4) | 28(4) | 60(4) | −14(3) | 4(3) | 0(3) |
| C18 | 41(4) | 40(4) | 41(3) | −1(3) | −3(3) | 8(3) |
| C9 | 45(4) | 30(4) | 48(4) | 0(3) | −1(3) | −5(3) |
| Cl | 35(4) | 36(4) | 73(5) | −17(4) | 0(3) | 2(3) |
| C109 | 40(5) | 73(6) | 62(5) | 19(4) | 8(4) | 12(4) |

TABLE 3c

Bond Lengths for data.

| Atom | Atom | Length/Å | Atom | Atom | Length/Å |
|---|---|---|---|---|---|
| Cl10 | C120 | 1.736(7) | C118 | C117 | 1.379(10) |
| Cl1 | C20 | 1.724(8) | C118 | C119 | 1.385(10) |
| F101 | C119 | 1.341(8) | C116 | C117 | 1.403(10) |
| O201 | C201 | 1.414(10) | C116 | C112 | 1.465(10) |
| F1 | C19 | 1.358(8) | C116 | C121 | 1.412(10) |
| N6 | N5 | 1.374(8) | C111 | C112 | 1.430(9) |
| N6 | C11 | 1.365(8) | C16 | C12 | 1.471(10) |
| N6 | C15 | 1.379(8) | C16 | C17 | 1.397(10) |
| N102 | N101 | 1.351(8) | C16 | C21 | 1.391(10) |
| N102 | C101 | 1.334(9) | C12 | C13 | 1.385(9) |
| N105 | N106 | 1.384(8) | C112 | C113 | 1.390(9) |
| N105 | C110 | 1.353(8) | C13 | C14 | 1.385(10) |
| N106 | C111 | 1.368(9) | C7 | C2 | 1.378(10) |
| N106 | C115 | 1.366(8) | C7 | C6 | 1.489(11) |
| N104 | C110 | 1.360(8) | C104 | C105 | 1.549(9) |
| N104 | C111 | 1.352(8) | C4 | C5 | 1.529(10) |
| N101 | C107 | 1.363(8) | C4 | C3 | 1.531(9) |
| N101 | C108 | 1.469(9) | C14 | C15 | 1.366(10) |
| N103 | C110 | 1.357(8) | C2 | C3 | 1.502(9) |
| N103 | C104 | 1.451(8) | C2 | C1 | 1.413(10) |
| N4 | C11 | 1.342(8) | C107 | C106 | 1.486(10) |
| N4 | C10 | 1.350(8) | C106 | C105 | 1.535(10) |
| N5 | C10 | 1.359(8) | C17 | C18 | 1.381(11) |
| N3 | C10 | 1.362(8) | C5 | C6 | 1.540(10) |
| N3 | C4 | 1.465(8) | C119 | C120 | 1.400(10) |
| N2 | N1 | 1.370(8) | C115 | C114 | 1.364(10) |
| N2 | C7 | 1.350(9) | C114 | C113 | 1.400(11) |
| N2 | C8 | 1.445(9) | C108 | C109 | 1.506(11) |
| N1 | C1 | 1.342(10) | C19 | C20 | 1.391(11) |
| C102 | C103 | 1.505(9) | C19 | C18 | 1.362(11) |
| C102 | C101 | 1.399(10) | C21 | C20 | 1.387(10) |
| C102 | C107 | 1.395(10) | C121 | C120 | 1.368(10) |
| C11 | C12 | 1.428(9) | C8 | C9 | 1.514(10) |
| C103 | C104 | 1.527(9) | | | |

TABLE 3d

Bond Angles for data.

| Atom | Atom | Atom | Angle/° | Atom | Atom | Atom | Angle/° |
|---|---|---|---|---|---|---|---|
| N5 | N6 | C15 | 124.3(6) | C111 | C112 | C116 | 121.3(6) |
| C11 | N6 | N5 | 110.9(5) | C113 | C112 | C116 | 123.2(6) |
| C11 | N6 | C15 | 124.7(6) | C113 | C112 | C111 | 115.5(6) |
| C101 | N102 | N101 | 104.6(5) | C12 | C13 | C14 | 122.8(7) |
| C110 | N105 | N106 | 100.6(5) | N2 | C7 | C2 | 107.5(6) |
| C111 | N106 | N105 | 110.9(5) | N2 | C7 | C6 | 126.1(6) |
| C115 | N106 | N105 | 124.3(5) | C2 | C7 | C6 | 126.5(6) |
| C115 | N106 | C111 | 124.7(6) | N103 | C104 | C103 | 113.4(5) |
| C111 | N104 | C110 | 102.8(5) | N103 | C104 | C105 | 108.7(5) |
| N102 | N101 | C107 | 112.5(5) | C103 | C104 | C105 | 111.0(5) |
| N102 | N101 | C108 | 119.4(5) | N3 | C4 | C5 | 111.1(6) |
| C107 | N101 | C108 | 127.4(6) | N3 | C4 | C3 | 110.0(6) |
| C110 | N103 | C104 | 122.0(5) | C5 | C4 | C3 | 111.5(6) |

TABLE 3d-continued

Bond Angles for data.

| Atom | Atom | Atom | Angler/° | Atom | Atom | Atom | Angler/° |
|------|------|------|----------|------|------|------|----------|
| C11 | N4 | C10 | 102.6(5) | C15 | C14 | C13 | 121.1(6) |
| C10 | N5 | N6 | 100.1(5) | C7 | C2 | C3 | 122.4(6) |
| C10 | N3 | C4 | 121.0(5) | C7 | C2 | C1 | 105.2(6) |
| N1 | N2 | C8 | 119.1(6) | C1 | C2 | C3 | 132.4(7) |
| C7 | N2 | N1 | 111.5(5) | C14 | C15 | N6 | 116.4(6) |
| C7 | N2 | C8 | 128.9(6) | N101 | C107 | C102 | 106.1(6) |
| C1 | N1 | N2 | 105.2(6) | N101 | C107 | C106 | 127.3(6) |
| C101 | C102 | C103 | 134.1(6) | C102 | C107 | C106 | 126.6(6) |
| C107 | C102 | C103 | 121.4(6) | C107 | C106 | C105 | 109.5(5) |
| C107 | C102 | C101 | 104.5(6) | C18 | C17 | C16 | 121.3(7) |
| N6 | C11 | C12 | 118.8(6) | C4 | C5 | C6 | 110.8(6) |
| N4 | C11 | N6 | 109.6(5) | F101 | C119 | C118 | 120.4(6) |
| N4 | C11 | C12 | 131.4(6) | F101 | C119 | C120 | 119.7(6) |
| C102 | C103 | C104 | 109.4(5) | C118 | C119 | C120 | 119.9(6) |
| N102 | C101 | C102 | 112.3(6) | C114 | C115 | N106 | 116.9(6) |
| C117 | C118 | C119 | 119.9(6) | C115 | C114 | C113 | 120.9(6) |
| C117 | C116 | C112 | 120.1(6) | N101 | C108 | C109 | 111.1(6) |
| C117 | C116 | C121 | 117.7(6) | C106 | C105 | C104 | 110.9(5) |
| C121 | C116 | C112 | 122.2(6) | F1 | C19 | C20 | 119.0(7) |
| N4 | C10 | N5 | 116.7(6) | F1 | C19 | C18 | 119.3(7) |
| N4 | C10 | N3 | 121.9(5) | C18 | C19 | C20 | 121.7(6) |
| N5 | C10 | N3 | 121.3(5) | C20 | C21 | C16 | 120.9(7) |
| C118 | C117 | C116 | 121.3(6) | C120 | C121 | C116 | 121.1(6) |
| N105 | C110 | N104 | 116.5(5) | C112 | C113 | C114 | 122.6(6) |
| N105 | C110 | N103 | 121.8(6) | C119 | C120 | Cl10 | 119.1(5) |
| N103 | C110 | N104 | 121.7(5) | C121 | C120 | Cl10 | 120.9(6) |
| N106 | C111 | C112 | 119.4(6) | C121 | C120 | C119 | 120.1(6) |
| N104 | C111 | N106 | 109.3(5) | C19 | C20 | Cl1 | 120.2(5) |
| N104 | C111 | C112 | 131.2(6) | C21 | C20 | Cl1 | 121.0(6) |
| C17 | C16 | C12 | 120.6(6) | C21 | C20 | C19 | 118.8(7) |
| C21 | C16 | C12 | 121.2(6.7) | C7 | C6 | C5 | 108.3(6) |
| C21 | C16 | C17 | 118.2(6) | N2 | C8 | C9 | 112.2(6) |
| C11 | C12 | C16 | 120.7(6) | C2 | C3 | C4 | 109.1(6) |
| C13 | C12 | C11 | 116.2(6) | C19 | C18 | C17 | 119.1(7) |
| C13 | C12 | C16 | 123.1(6) | Ni | C1 | C2 | 110.7(7) |

TABLE 3e

Hydrogen Atom Coordinates (Å × 10$^4$) and Isotropic Displacement Parameters (Å$^2$ × 10$^3$) for data.

| Atom | x | y | z | U(eq) |
|------|------|------|------|-------|
| H201 | −8340 | 11419 | 4766 | 65 |
| H103 | 13762 | 1860 | 821 | 37 |
| H3 | −1178 | 7379 | 4049 | 44 |
| H10A | 12296 | −297 | 674 | 38 |
| H10B | 12760 | 207 | −45 | 38 |
| H101 | 13077 | −1913 | −72 | 37 |
| H118 | 3602 | 4269 | 1563 | 40 |
| H117 | 4472 | 2874 | 1899 | 41 |
| H13 | 6617 | 7150 | 1955 | 44 |
| H104 | 14880 | 317 | 1330 | 37 |
| H4 | −1223 | 9128 | 3691 | 41 |
| H14 | 5748 | 8520 | 1574 | 44 |
| H15 | 3093 | 9188 | 1986 | 42 |
| H10C | 18571 | 212 | 107 | 43 |
| H10D | 18322 | 6 | 940 | 43 |
| H17 | 8014 | 6370 | 3011 | 44 |
| H5A | 474 | 8939 | 4856 | 50 |
| H5B | −1431 | 8585 | 5158 | 50 |
| H115 | 9128 | −155 | 2618 | 41 |
| H114 | 6438 | 475 | 3031 | 45 |
| H10E | 20069 | −1241 | 101 | 42 |
| H10F | 19483 | −2142 | −274 | 42 |
| H10G | 15917 | 1065 | −3 | 42 |
| H10H | 16912 | 1335 | 767 | 42 |
| H21 | 2591 | 5567 | 2942 | 42 |
| H121 | 9997 | 3540 | 1881 | 40 |
| H113 | 5646 | 1895 | 2740 | 44 |
| H6A | −1362 | 10039 | 5462 | 49 |
| H6B | −776 | 10318 | 4678 | 49 |
| H8A | −3095 | 11363 | 5535 | 47 |

TABLE 3e-continued

Hydrogen Atom Coordinates (Å × 10$^4$) and Isotropic Displacement Parameters (Å$^2$ × 10$^3$) for data.

| Atom | x | y | z | U(eq) |
|------|------|------|------|-------|
| H8B | −5294 | 11587 | 5530 | 47 |
| H20A | −8292 | 12074 | 3745 | 74 |
| H20B | −10081 | 12622 | 3951 | 74 |
| H20C | −10301 | 11615 | 3773 | 74 |
| H3A | −4205 | 8545 | 3439 | 50 |
| H3B | −4195 | 8112 | 4223 | 50 |
| H18 | 9019 | 5043 | 3484 | 49 |
| H9A | −3149 | 12011 | 4347 | 62 |
| H9B | −3466 | 12681 | 4982 | 62 |
| H9C | −5229 | 12349 | 4468 | 62 |
| H1 | −7457 | 9553 | 3856 | 58 |
| H101 | 18959 | −2732 | 859 | 87 |
| H10J | 19517 | −1830 | 1237 | 87 |
| H10K | 21078 | −2381 | 864 | 87 |

Refinement Model Description

Number of restraints—1, number of constraints—unknown.

Details:
1. Fixed Uiso
   At 1.2 times of: All C(H) groups, All C(H,H) groups, All N(H) groups
   At 1.5 times of: All C(H,H,H) groups, All O(H) groups
2.a Ternary CH refined with riding coordinates: C104 (H104), C4(H4)
2.b Secondary CH2 refined with riding coordinates: C103 (H10A,H10B), C106(H10C,H10D), C5(H5A,H5B), C108(H10E,H10F), C105(H10G, H10H), C6(H6A, H6B), C8(H8A,H8B), C3(H3A,H3B)
2.c Aromatic/amide H refined with riding coordinates: N103(H103), N3(H3), C101(H101), C118(H118), C117(H117), C13(H13), C14(H14), C15(H15), C17 (H17), C115(H115), C114(H114), C21(H21), C121 (H121), C113(H113), C18(H18), C1(H1)
2.d Idealised Me refined as rotating group: C201(H20A, H20B,H20C), C9(H9A,H9B,H9C), C109(H101,H10J, H10K)
2.e Idealised tetrahedral OH refined as rotating group: O201(H201)

S-61

(S)-[8-(3-Chloro-4-fluoro-phenyl)-[1,2,4]triazolo[1,5-a] pyridine-2-yl]-(1-ethyl-4,5,6,7-tetrahydro-1H-indazol-5-yl)-amine (S-61). Prepared according to general procedure D-2 using chiral halo triazolo pyridine S-39a and 3-chloro-4-fluoro-phenylboronic acid. Yield: 108 mg (71%). HRMS (ESI$^+$) calculated for $C_{21}H_{20}ClFN_6$ [M+H]$^+$ m/z 411.1500, found 411.1502. $^1$H NMR (400 MHz, (CD$_3$)$_2$SO) δ 8.65 (dd, J=6.6, 1.0 Hz, 1H), 8.47 (dd, J=7.4, 2.3 Hz, 1H), 8.14 (m, 1H), 7.82 (dd, J=7.5, 1.0 Hz, 1H), 7.54 (m, 1H), 7.14 (s, 1H), 6.99 (dd, J=7.5, 6.6 Hz, 1H), 6.86 (d, J=7.5 Hz, 1H), 3.97 (q, J=7.2 Hz, 2H), 3.81-3.91 (m, 1H), 2.85-2.93 (m, 1H), 2.76-2.85 (m, 1H), 2.60-2.71 (m, 1H), 2.44-2.52 (m, 1H, partially obscured by DMSO signal), 2.14-2.23 (m, 1H), 1.75-1.86 (m, 1H), 1.29 (t, J=7.2 Hz, 3H). HPLC (Method 5): $R_t$=0.65 min. Enantiomeric purity (method 14): 97.9% ee. Specific optical rotation: $[\alpha]^{20}_D$=−7.5° (c 0.4 mg/mL, MeOH).

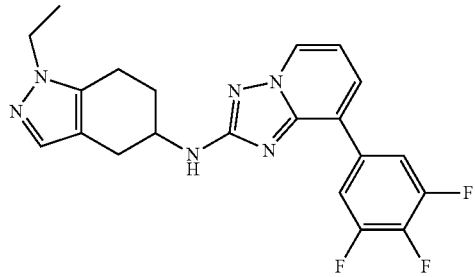

62

(1-Ethyl-4,5,6,7-tetrahydro-1H-indazol-5-yl)-[8-(3,4,5-trifluoro-phenyl)-[1,2,4]triazolo[1,5-a]pyridine-2-yl]-amine (62). Prepared according to general procedure D-2 using halo triazolo pyridine 39a and 3,4,5-trifluoro-phenylboronic acid using bis(triphenylphosphine)palladium(II) chloride as catalyst. Yield: 14 mg (19%). LCMS (ESI$^+$) calculated for $C_{21}H_{19}F_3N_6$ [M+H]$^+$ m/z 413.1702, found 413.1. $^1$H NMR (400 MHz, (CD$_3$)$_2$SO) δ 8.69 (dd, J=6.6, 0.9 Hz, 1H), 8.23-8.32 (m, 2H), 7.92 (dd, J=7.6, 0.9 Hz, 1H), 7.15 (s, 1H), 7.01 (dd, J=7.4, 6.8 Hz, 1H), 6.93 (d, J=7.4 Hz, 1H), 3.97 (q, J=7.2 Hz, 2H), 3.82-3.92 (m, 1H), 2.85-2.92 (m, 1H), 2.77-2.85 (m, 1H), 2.61-2.71 (m, 1H), 2.44-2.54 (m, 1H), 2.14-2.22 (m, 1H), 1.76-1.87 (m, 1H), 1.29 (t, J=7.2 Hz, 3H). HPLC (Method 3): $R_t$=0.67 min.

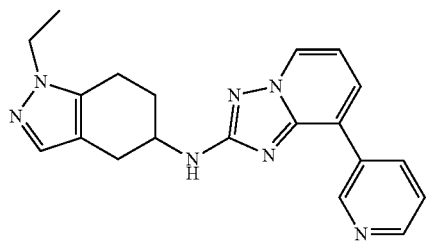

63

(1-Ethyl-4,5,6,7-tetrahydro-1H-indazol-5-yl)-(8-pyridin-3-yl-[1,2,4]triazolo[1,5-a]pyridine-2-yl)-amine (63). Prepared according to general procedure D-1 using halo triazolo pyridine 39b and pyridine-3-ylboronic acid. Yield: 26 mg (72%). LCMS (ESI$^+$) calculated for $C_{20}H_{21}N_7$ [M+H]$^+$ m/z 360.1937, found 360.3. $^1$H NMR (400 MHz, (CD$_3$)$_2$SO) δ 9.30 (d, J=2.1 Hz, 1H), 8.69 (dd, J=6.6, 0.9 Hz, 1H), 8.59 (dd, J=4.8, 1.7 Hz, 1H), 8.50 (m, 1H), 7.85 (dd, J=7.4, 0.9 Hz, 1H), 7.53 (dd, J=8.0, 4.8 Hz, 1H), 7.15 (s, 1H), 7.03 (dd, J=7.4, 6.6 Hz, 1H), 6.90 (d, J=7.5 Hz, 1H), 3.97 (q, J=7.3 Hz, 2H), 3.82-3.92 (m, 1H), 2.76-2.92 (m, 2H), 2.61-2.71 (m, 1H), 2.44-2.50 (m, 1H), 2.12-2.20 (m, 1H), 1.73-1.86 (m, 1H), 1.28 (t, J=7.3 Hz, 3H). HPLC (Method 9): $R_t$=0.39 min.

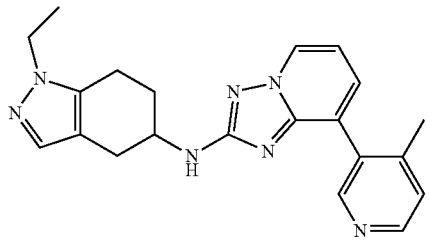

64

(1-Ethyl-4,5,6,7-tetrahydro-1H-indazol-5-yl)-[8-(4-methyl-pyridin-3-yl)-[1,2,4]triazolo[1,5-a]pyridine-2-yl]-amine (64). Prepared according to general procedure D-2 using halo triazolo pyridine 39a and 4-methyl-pyridin-3-ylboronic acid pinacol ester. Yield: 12 mg (12%). LCMS (ESI$^+$) calculated for $C_{21}H_{23}N_7$ [M+H]$^+$ m/z 374.2, found 374.2. $^1$H NMR (400 MHz, (CD$_3$)$_2$SO) δ 8.69 (dd, J=6.7, 1.0 Hz, 1H), 8.48-8.52 (m, 2H), 7.44 (dd, J=7.3, 1.0 Hz, 1H), 7.39-7.43 (m, 1H), 7.12 (s, 1H), 6.99 (dd, J=7.3, 6.7 Hz, 1H), 6.72 (d, J=7.3 Hz, 1H), 3.95 (q, J=7.2 Hz, 2H), 3.75-3.87 (m, 1H), 2.72-2.90 (m, 2H), 2.56-2.69 (m, 1H), 2.38-2.47 (m, 1H), 2.24 (s, 3H), 2.07-2.17 (m, 1H), 1.71-1.83 (m, 1H), 1.27 (t, J=7.2 Hz, 3H). HPLC (Method 5): $R_t$=0.35 min.

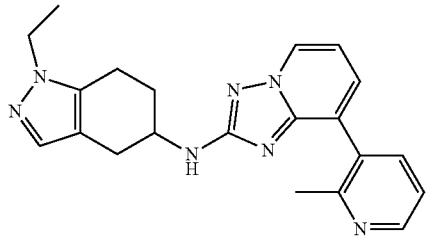

65

(1-Ethyl-4,5,6,7-tetrahydro-1H-indazol-5-yl)-[8-(2-methyl-pyridin-3-yl)-[1,2,4]triazolo[1,5-a]pyridine-2-yl]-amine (65). Prepared according to general procedure D-1 using halo triazolo pyridine 39b and 2-methyl-pyridine-3-ylboronic acid. Yield: 13 mg (34%). LCMS (ESI$^+$) calculated for $C_{21}H_{23}N_7$ [M+H]$^+$ m/z 374.2093, found 374.3. $^1$H NMR (400 MHz, (CD$_3$)$_2$SO) δ 8.68 (d, J=6.7, 1.0 Hz, 1H), 8.50 (dd, J=4.8, 1.6 Hz, 1H), 7.73 (dd, J=7.7, 1.6 Hz, 1H), 7.43 (dd, J=7.3, 1.0, 1H), 7.32 (dd, J=7.7, 4.9 Hz, 1H), 7.13 (s, 1H), 6.99 (dd, J=7.7.3, 6.7 Hz, 1H), 6.79 (d, J=7.5 Hz, 1H), 3.95 (q, J=7.2 Hz, 2H), 3.74-3.85 (m, 1H), 2.73-2.87 (m, 2H), 2.57-2.69 (m, 1H), 2.38-2.46 (m, 1H), 2.37 (s, 3H), 2.08-2.18 (m, 1H), 1.69-1.81 (m, 1H), 1.26 (t, J=7.2 Hz, 3H). HPLC (Method 9): $R_t$=0.38 min.

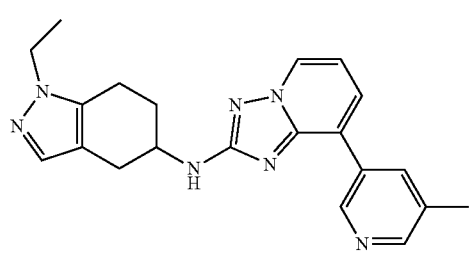

66

(1-Ethyl-4,5,6,7-tetrahydro-1H-indazol-5-yl)-[8-(5-methyl-pyridin-3-yl)-[1,2,4]triazolo[1,5-a]pyridine-2-yl]-amine (66). Prepared according to general procedure D-2 using halo triazolo pyridine 39a and 5-methyl-pyridin-3-ylboronic acid (1.5 equiv). Yield: 4 mg (11%). LCMS (ESI$^+$) calculated for $C_{21}H_{23}N_7$ [M+H]$^+$ m/z 374.2093, found 374.2. $^1$H NMR (400 MHz, (CD$_3$)$_2$SO) δ 9.18 (d, J=1.8 Hz, 1H), 8.68 (dd, J=6.6, 1.0 Hz, 1H), 8.50-8.48 (m, 1H), 8.45-8.43 (m, 1H), 7.85 (dd, J=7.5, 1.1 Hz, 1H), 7.15 (s, 1H), 7.02 (dd, J=7.5, 6.7 Hz, 1H), 6.85 (br s, 1H), 3.97 (q, J=7.3 Hz, 2H), 3.92-3.82 (m, 1H), 2.85-2.92 (m, 1H), 2.76-2.85 (m, 1H), 2.61-2.72 (m, 1H), 2.45-2.55 (m, 1H, partially obscured by DMSO signal), 2.41 (s, 3H), 2.13-2.21 (m, 1H), 1.75-1.87 (m, 1H), 1.29 (t, J=7.3 Hz, 3H). HPLC (Method 5): R$_t$=0.36 min.

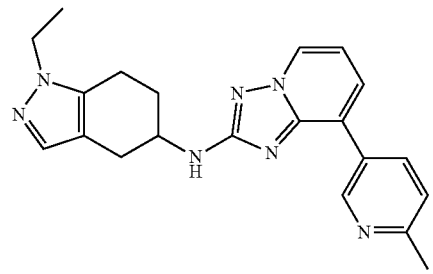

67

(1-Ethyl-4,5,6,7-tetrahydro-1H-indazol-5-yl)-[8-(6-methyl-pyridin-3-yl)-[1,2,4]triazolo[1,5-a]pyridine-2-yl]-amine (67). Prepared according to general procedure D-1 using chloro triazolo pyridine 39b and 6-methyl-pyridin-3-ylboronic acid (1.5 equiv). Yield: 36 mg (98%). LCMS (ESI$^+$) calculated for $C_{21}H_{23}N_7$ [M+H]$^+$ m/z 374.2093, found 374.3. $^1$H NMR (400 MHz, (CD$_3$)$_2$SO) δ 9.50 (d, J=1.5 Hz, 1H), 9.00 (m, 1H), 8.74 (dd, J=6.6, 0.9 Hz, 1H), 8.00 (dd, J=7.6, 0.8 Hz, 1H), 7.88 (m, 1H), 7.17 (s, 1H), 7.08 (dd, J=7.4, 6.6 Hz, 1H), 6.92 (br, 1H), 3.98 (q, J=7.2 Hz, 2H), 3.87-3.96 (m, 1H), 2.78-2.94 (m, 2H), 2.62-2.73 (m, 1H), 2.71 (s, 3H), 2.44-2.52 (m, 1H, largely obscured by DMSO signal), 2.13-2.33 (m, 1H), 1.78-1.89 (m, 1H), 1.29 (t, J=7.2 Hz, 3H). HPLC (Method 10): R$_t$=0.74 min.

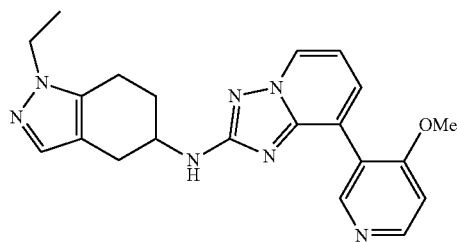

68

(1-Ethyl-4,5,6,7-tetrahydro-1H-indazol-5-yl)-[8-(4-methoxy-pyridin-3-yl)-[1,2,4]triazolo[1,5-a]pyridine-2-yl]-amine (68). Prepared according to general procedure D-1 using halo triazolo pyridine 39b and 4-methoxy-pyridine-3-ylboronic acid. Yield: 26 mg (66%). LCMS (ESI$^+$) calculated for $C_{21}H_{23}N_7O$ [M+H]$^+$ m/z 390.2042, found 390.123. $^1$H NMR (400 MHz, (CD$_3$)$_2$SO) δ 8.94 (dd, J=2.4, 0.6 Hz, 1H), 8.60 (dd, J=6.7, 1.1 Hz, 1H), 8.44 (dd, J=8.7, 2.4 Hz, 1H), 7.74 (dd, J=7.4, 1.1 Hz, 1H), 7.14 (s, 1H), 6.98 (dd, J=7.4, 6.7 Hz, 1H), 6.94 (dd, J=8.7, 0.6 Hz, 1H), 6.76 (d, J=7.6 Hz, 1H), 3.97 (q, J=7.3 Hz, 2H), 3.84-3.93 (m, 1H), 3.91 (s, 3H), 2.76-2.92 (m, 2H), 2.60-2.72 (m, 1H), 2.43-2.49 (m, 1H), 2.12-2.21 (m, 1H), 1.75-1.87 (m, 1H), 1.29 (t, J=7.3 Hz, 3H). HPLC (Method 10): R$_t$=0.96 min.

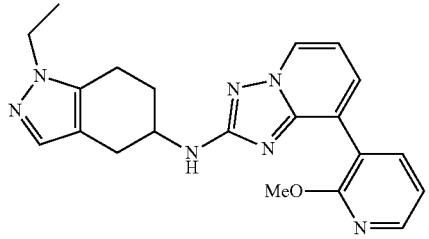

69

(1-Ethyl-4,5,6,7-tetrahydro-1H-indazol-5-yl)-[8-(2-methoxy-pyridin-3-yl)-[1,2,4]triazolo[1,5-a]pyridine-2-yl]-amine (69). Prepared according to general procedure D-1 using halo triazolo pyridine 39b and 2-methoxy-pyridine-3-ylboronic acid. Yield: 21 mg (53%). LCMS (ESI$^+$) calculated for $C_{21}H_{23}N_7O$ [M+H]$^+$ m/z 390.2042, found 390.1278. $^1$H NMR (400 MHz, (CD$_3$)$_2$SO) δ 8.60 (dd, J=6.7, 1.1 Hz, 1H), 8.21 (dd, J=4.9, 1.9 Hz, 1H), 8.06 (dd, J=7.4, 1.9 Hz, 1H), 7.58 (dd, J=7.4, 1.1 Hz, 1H), 7.13 (s, 1H), 7.10 (dd, J=7.4, 4.9 Hz, 1H), 6.95 (dd, J=7.4, 6.7 Hz, 1H), 6.69 (d, J=7.3 Hz, 1H), 3.96 (q, J=7.2 Hz, 2H), 3.86 (s, 3H), 3.78-3.85 (m, 1H), 2.73-2.90 (m, 2H), 2.58-2.69 (m, 1H), 2.39-2.48 (m, 1H), 2.09-2.19 (m, 1H), 1.71-1.83 (m, 1H), 1.27 (t, J=7.2 Hz, 3H). HPLC (Method 10): R$_t$=0.96 min.

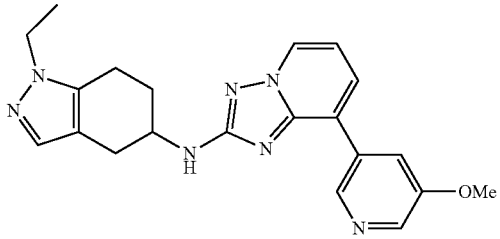

70

(1-Ethyl-4,5,6,7-tetrahydro-1H-indazol-5-yl)-[8-(5-methoxy-pyridin-3-yl)-[1,2,4]triazolo[1,5-a]pyridine-2-yl]-amine (70). Prepared according to general procedure D-2 using halo triazolo pyridine 39a and 5-methoxy-pyridin-3-ylboronic acid (1.7 equiv). Yield: 43 mg (65%). LCMS (ESI$^+$) calculated for $C_{21}H_{23}N_7O$ [M+H]$^+$ m/z 390.2042, found 390.2. $^1$H NMR (400 MHz, (CD$_3$)$_2$SO) δ 8.96 (d, J=1.6 Hz, 1H), 8.68 (dd, J=6.7, 0.6 Hz, 1H), 8.35 (m, 1H), 8.23 (m, 1H), 7.92 (dd, J=7.5, 0.6 Hz, 1H), 7.15 (s, 1H), 7.02 (dd, J=7.5, 6.7 Hz, 1H), 6.84 (br s, 1H), 3.97 (q, J=7.3 Hz, 2H), 3.92 (s, 3H), 3.84-3.92 (m, 1H), 2.86-2.94 (m, 1H), 2.76-2.86 (m, 1H), 2.60-2.72 (m, 1H), 2.45-2.52 (m, 1H, partially obscured by DMSO signal), 2.13-2.22 (m, 1H), 1.77-1.88 (m, 1H), 1.29 (t, J=7.3 Hz, 3H). HPLC (Method 5): R$_t$=0.40 min.

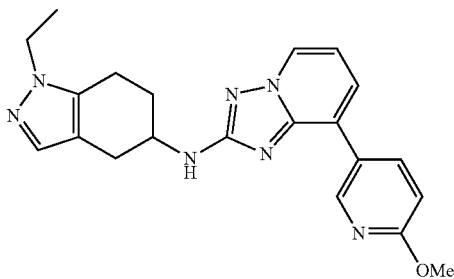

(1-Ethyl-4,5,6,7-tetrahydro-1H-indazol-5-yl)-[8-(6-methoxy-pyridin-3-yl)-[1,2,4]triazolo[1,5-a]pyridine-2-yl]-amine (71). Prepared according to general procedure D-2 using halo triazolo pyridine 39a and 6-methoxy-pyridin-3-ylboronic acid (1.7 equiv). Yield: 29 mg (56%). LCMS (ESI+) calculated for $C_{21}H_{23}N_7O$ [M+H]+ m/z 390.2042, found 390.3. $^1$H NMR (400 MHz, $(CD_3)_2SO$) δ 8.94 (d, J=2.4 Hz, 1H), 8.60 (dd, J=6.6, 1.0 Hz, 1H), 8.44 (dd, J=8.8, 2.5 Hz, 1H), 7.74 (dd, J=7.4, 1.0 Hz, 1H), 7.14 (s, 1H), 6.98 (dd, J=7.4, 6.6 Hz, 1H), 6.94 (d, J=8.8 Hz, 1H), 6.76 (d, J=7.6 Hz, 1H), 3.97 (q, J=7.2 Hz, 2H), 3.91 (s, 3H), 3.84-3.93 (m, 1H), 2.85-2.93 (m, 1H), 2.76-2.85 (m, 1H), 2.61-2.72 (m, 1H), 2.43-2.52 (m, 1H, partly obscured by DMSO signal), 2.12-2.21 (m, 1H), 1.75-1.87 (m, 1H), 1.29 (t, J=7.2 Hz, 3H). HPLC (Method 5): $R_t$=0.53 min.

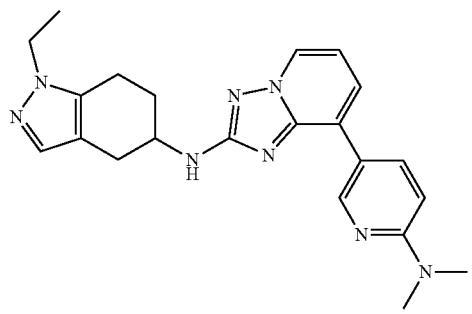

[8-(6-Dimethylamino-pyridin-3-yl)-[1,2,4]triazolo[1,5-a]pyridine-2-yl]-(1-ethyl-4,5,6,7-tetrahydro-1H-indazol-5-yl)-amine (72). Prepared according to general procedure D-2 using halo triazolo pyridine 39a and 6-dimethylamino-pyridin-3-ylboronic acid. Yield: 8 mg (9%). LCMS (ESI+) calculated for $C_{22}H_{26}N_8$ [M+H]+ m/z 403.2359, found 403.3. $^1$H NMR (400 MHz, $(CD_3)_2SO$) δ 8.96 (m, 1H), 8.55 (d, J=6.5 Hz, 1H), 8.37-8.44 (m, 1H), 7.95 (s, 1H), 7.74 (m, 1H), 7.15 (s, 1H), 6.97 (m, 1H), 6.72 (br, 1H), 3.97 (q, J=7.2 Hz, 2H), 3.86-3.94 (m, 1H), 3.14 (s, 6H), 2.85-2.93 (m, 1H), 2.76-2.85 (m, 1H), 2.43-2.51 (m, 1H), 2.15-2.21 (m, 1H), 1.77-1.88 (m, 1H), 1.29 (t, J=7.2 Hz, 3H). HPLC (Method 5): $R_t$=0.39 min.

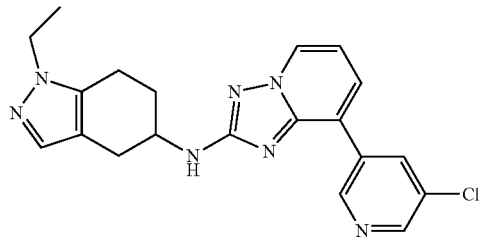

[8-(5-Chloro-pyridin-3-yl)-[1,2,4]triazolo[1,5-a]pyridine-2-yl]-(1-ethyl-4,5,6,7-tetrahydro-1H-indazol-5-yl)-amine (73). Prepared according to general procedure D-2 using halo triazolo pyridine 39a and 5-chloro-pyridin-3-ylboronic acid (1.6 equiv). Yield: 54 mg (81%). LCMS (ESI+) calculated for $C_{20}H_{20}ClN_7$ [M+H]+ m/z 394.1546, found 394.2. $^1$H NMR (400 MHz, $(CD_3)_2SO$) δ 9.28 (d, J=1.9 Hz, 1H), 8.75 (dd, J=2.3, 2.3 Hz, 1H), 8.71 (dd, J=6.7, 0.9 Hz, 1H), 8.64 (d, J=2.3 Hz, 1H), 7.96 (dd, J=7.5, 0.9 Hz, 1H), 7.15 (s, 1H), 7.03 (dd, J=7.5, 6.7 Hz, 1H), 6.92 (br s, 1H), 3.97 (q, J=7.2 Hz, 2H), 3.91-3.83 (m, 1H), 2.85-2.93 (m, 1H), 2.77-2.85 (m, 1H), 2.71-2.61 (m, 1H), 2.52-2.45 (m, 1H, partially obscured by DSMO signal), 2.22-2.14 (m, 1H), 1.87-1.76 (m, 1H), 1.29 (t, J=7.2 Hz, 3H). HPLC (Method 5): $R_t$=0.56 min.

Biological Data

Screening for the inhibition of Aβ42 production was performed using H4 neuroglioma cells stably expressing the human APP695 isoform grown in Dulbecco's Modified Eagles medium (DMEM) GlutaMAX supplemented with 10% Fetal Bovine Serum and 250 μg/mL Zeocine. Cells were plated out to near confluency. The compounds to be tested were received as 10 mM stocks in 100% DMSO. A dilution series was initially generated in 100% DMSO and then diluted 200-fold in cell culture media such that the tested concentration range was 30 μM to 0.1 nM and the final DMSO concentration was 0.5%. The diluted compounds were incubated with the cells for 22 hours in an incubator at 37° C. and 5% $CO_2$. Aβ42 levels were measured post-incubation from the supernatant of the cells using an Aβ42 specific electrochemiluminescence assay provided by Meso Scale Discovery (Catalog #L21CA-1). The measurement of Aβ42 levels were performed according to the manufacturer's protocol.

Aβ total levels were likewise determined using a specific electrochemiluminescence assay provided by Meso Scale Discovery (Catalog #L21ZA-1) according to the manufacturer's protocol. To identify compounds which preferentially inhibited Aβ42, the ratio Aβ total IC50/Aβ42 IC50 was determined, where the higher the ratio, the more specific the inhibition of Aβ42 over Aβtotal.

TABLE 4a

Activity of the examples compiled in the experimental part, based on both Aβ42 cellular $IC_{50}$ values in H4 neuroglioma cells as well as selectivity ratio vs. Aβ$_{total}$.

| Example no. | Aβ$_{42}$ IC$_{50}$ [μM] | Ratio Aβ$_{Total}$ IC$_{50}$/Aβ$_{42}$ IC$_{50}$ |
|---|---|---|
| 9 | 1.26 | 3 |
| 10 | 0.38 | 27 |
| 40 | >30 | 1 |
| 41 | 4.57 | 1 |

TABLE 4a-continued

Activity of the examples compiled in the experimental part, based on both Aβ$_{42}$ cellular IC$_{50}$ values in H4 neuroglioma cells as well as selectivity ratio vs. Aβ$_{total}$.

| Example no. | Aβ$_{42}$ IC$_{50}$ [μm] | Ratio Aβ$_{Total}$ IC$_{50}$/Aβ$_{42}$ IC$_{50}$ |
|---|---|---|
| 42 | 0.07 | 23 |
| R-42 | 0.04 | 254 |
| 43 | 0.06 | 48 |
| 44 | 0.43 | 64 |
| 45 | 3.40 | 4 |
| 46 | 2.77 | 4 |
| 47 | >30 | 1 |
| 48 | 0.75 | 22 |
| 49 | 0.95 | 15 |
| 50 | 21.70 | 1 |
| 51 | 2.20 | 2 |
| 52 | 0.74 | 2 |
| 53 | 1.39 | 1 |
| 54 | 3.13 | 10 |
| 55 | 0.18 | 120 |
| 56 | 0.16 | 49 |
| 57 | 0.07 | 104 |
| 58 | 0.06 | 34 |
| 59 | 0.04 | 49 |
| 60 | 0.06 | 113 |
| 61 | 0.02 | 152 |
| R-61 | 0.009 | 1098 |
| S-61 | 0.194 | 42 |
| 62 | 0.03 | 128 |
| 63 | 0.35 | 85 |
| 64 | 0.73 | 41 |
| 65 | 0.68 | 44 |
| 66 | 0.20 | 154 |
| 67 | 0.67 | 45 |
| 68 | 0.12 | 241 |
| 69 | 0.50 | 60 |
| 70 | 0.20 | 60 |
| 71 | 0.09 | 332 |
| 72 | 0.05 | 538 |
| 73 | 0.04 | 420 |

Gamma secretase modulators are compounds that selectively lower Aβ$_{42}$ levels while leaving Aβ$_{total}$ levels unchanged, therefore are compounds that show a high selectivity for Aβ$_{42}$ reduction (high value for Ratio Aβ$_{total}$ IC$_{50}$/Aβ$_{42}$ IC$_{50}$).

TABLE 4b

Activity of the closest prior art compounds (examples 263, 293 and 302 in WO2009/155551) as obtained in the same assay as compounds in table 4a, based on both Aβ$_{42}$ cellular IC$_{50}$ values in H4 neuroglioma cells as well as selectivity ratio vs. Aβ$_{total}$.

| Example no. in WO2009/155551 | Aβ$_{42}$ IC$_{50}$ [μm] | Ratio Aβ$_{Total}$ IC$_{50}$/Aβ$_{42}$ IC$_{50}$ |
|---|---|---|
| 263 | 6 | 2 |
| 293 | 7 | 1 |
| 302 | >10 | 1 |

Thermo Fisher Scientific SelectScreen™ Biochemical Kinase Profiling Service Z'-LYTE™ Screening Protocol and Assay Conditions
Assay Theory The r-LYTE biochemical assay employs a fluorescence-based, coupled-enzyme format and is based on the differential sensitivity of phosphorylated and non-phosphorylated peptides to proteolytic cleavage. The peptide substrate is labeled with two fluorophores—one at each end—that make up a FRET pair. In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (Emission Ratio=Coumarin emission (445 nm)/Fluorescein emission (520 nm)) of donor emission to acceptor emission after excitation of the donor fluorophore at 400 nm, is used to quantitate reaction progress, as shown in the equation below. A significant benefit of this ratiometric method for quantitating reaction progress is the elimination of well-to-well variations in FRET-peptide concentration and signal intensities. As a result, the assay yields very high Z'-factor values (>0.7) at a low percent phosphorylation. Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

Z'-LYTE Assay Conditions
Test Compounds

The Test Compounds are screened in 1% DMSO (final) in the well. For 10 point titrations, 3-fold serial dilutions are conducted from the starting concentration of the customer's choosing.

Peptide/Kinase Mixtures

All Peptide/Kinase Mixtures are diluted to a 2× working concentration in the appropriate Kinase Buffer (see section Kinase Specific Assay Conditions for a complete description).

ATP Solution

All ATP Solutions are diluted to a 4× working concentration in Kinase Buffer (50 mM HEPES pH 7.5, 0.01% BRIJ-35, 10 mM MgCl2, 1 mM EGTA). ATP Km apparent is previously determined using a Z"-LYTE assay.

Development Reagent Solution

The Development Reagent is diluted in Development Buffer (see section Kinase-Specific Assay Conditions—Direct and Cascade for a complete description).

10× Novel PKC Lipid Mix: 2 mg/ml Phosphatidyl Serine, 0.2 mg/ml DAG in 20 mM HEPES, pH 7.4, 0.3% CHAPS. For 5 mL 10× Novel PKC Lipid Mix:

1. Add 10 mgs Phosphatidyl Serine (Avanti Polar Lipids Part #8400032C or 840039C) and 1 mg DAG (Avanti Polar Lipids Part #800811C) to a glass tube.
2. Remove the chloroform from lipid mixture by evaporating to a clear, thin film under a stream of nitrogen. Continuous rotation of the tube, at an angle to ensure maximum surface area of the lipid solution, will promote the thinnest film.
3. Add 5 mLs resuspension buffer, 20 mM HEPES, 0.3% CHAPS, pH 7.4, to the dried lipid mix.
4. Heat gently to 50-60° C. for 1-2 minutes and vortex in short intervals until the lipids are dissolved to a clear or slightly hazy solution. The lipids are typically in solution after 2-3 heat/vortex cycles.
5. Cool to room temperature, aliquot into single use volumes and store at −20° C.

Assay Protocol

Bar-coded Corning, low volume NBS, black 384-well plate (Corning Cat. #4514)
1. 100 nL—100× Test Compound in 100% DMSO
2. 2.4 μL—Kinase buffer 3. 5 μL—2× Peptide/Kinase Mixture
4. 2.5 μL—4×ATP Solution
5. 30—second plate shake
6. 60—minute Kinase Reaction incubation at room temperature
7. 5 μL—Development Reagent Solution
8. 30—second plate shake
9. 60—minute Development Reaction incubation at room temperature
10. Read on fluorescence plate reader and analyze the data Z'-LYTE Assay Controls The following controls are made for each individual kinase and are located on the same plate as the kinase:

0% Phosphorylation Control (100% Inhibition Control)

The maximum Emission Ratio is established by the 0% Phosphorylation Control (100% Inhibition Control), which contains no ATP and therefore exhibits no kinase activity. This control yields 100% cleaved peptide in the Development Reaction.

100% Phosphorylation Control

The 100% Phosphorylation Control, which consists of a synthetically phosphorylated peptide of the same sequence as the peptide substrate, is designed to allow for the calculation of percent phosphorylation. This control yields a very low percentage of cleaved peptide in the Development Reaction. The 0% Phosphorylation and 100% Phosphorylation Controls allow one to calculate the percent Phosphorylation achieved in a specific reaction well. Control wells do not include any kinase inhibitors.

0% Inhibition Control

The minimum Emission Ratio in a screen is established by the 0% Inhibition Control, which contains active kinase. This control is designed to produce a 10-50%* phosphorylated peptide in the Kinase Reaction.

* Cascade assays may produce up to 70% phosphorylated peptide.

Known Inhibitor

A known inhibitor control standard curve, 10 point titration, is run for each individual kinase on the same plate as the kinase to ensure the kinase is inhibited within an expected IC50 range previously determined.

The following controls are prepared for each concentration of Test Compound assayed:

Development Reaction Interference

The Development Reaction Interference is established by comparing the Test Compound Control wells that do not contain ATP versus the 0% Phosphorylation Control (which does not contain the Test Compound). The expected value for a non-interfering compound should be 100%. Any value outside of 90% to 110% is flagged.

Test Compound Fluorescence Interference

The Test Compound Fluorescence Interference is determined by comparing the Test Compound Control wells that do not contain the Kinase/Peptide Mixture (zero peptide control) versus the 0% Inhibition Control. The expected value for a non-fluorescence compound should be 0%. Any value >20% is flagged.

Z'-LYTE Data Analysis

The following equations are used for each set of data points:

| | Equation |
|---|---|
| Correction for Background Fluorescence | $FI_{Sample} - FI_{TCFI\ Ctl}$ |
| Emission Ratio (using values collected for background fluorescence) | $\dfrac{\text{Coumarin Emission (445 nm)}}{\text{Fluorescein Emission (520 nm)}}$ |
| % Phosphorylation (% Phos) | $\left\{1 - \dfrac{(\text{Emission Ratio} \times F_{100\%}) - C_{100\%}}{(C_{0\%} - C_{100\%}) + [\text{Emission Ratio} \times (F_{100\%} - F_{0\%})]}\right\} * 100$ |
| % Inhibition | $\left\{1 - \dfrac{\%\ Phos_{Sample}}{\%\ Phos_{0\%\ Inhibition\ Ctl}}\right\} * 100$ |
| Z' (using Emission Ratio values) | $1 - \dfrac{3 * Stdev_{0\%\ Phos\ Ctl} + 3 * Stdev_{0\%\ Inhibition}}{Mean_{0\%\ Phos\ Ctl} - Mean_{0\%\ Inhibition}}$ |
| Difference Between Data Points (single point only) | $\lvert\%\ Inhibition_{Point\ 1} - \%\ Inhibition_{Point\ 2}\rvert$ |
| Development Reaction Interference (DRI) (no ATP control) | $\dfrac{\text{Emission Ratio}_{DRI\ Ctl}}{\text{Emission Ratio}_{0\%\ Phos\ Ctl}}$ |
| Test Compound Fluorescence Interference (TCFI) (check both Coumarin and Fluorescein emissions) | $\dfrac{FI_{TCFI\ Ctl}}{FI_{0\%\ Inhibitor\ Ctl}}$ |

FI = Fluorescence Intensity
$C_{100\%}$ = Average Coumarin emission signal of the 100% Phos. Control
$C_{0\%}$ = Average Coumarin emission signal of the 0% Phos. Control
$F_{100\%}$ = Average Fluorescein emission signal of the 100% Phos. Control
$F_{0\%}$ = Average Fluorescein emission signal of the 0% Phos. Control
DRI = Development Reaction Interference
TCFI = Test Compound Fluorescence Interference Graphing Software SelectScreen Kinase Profiling Service uses XLfit from IDBS. The dose response curve is curve fit to model number 205 (sigmoidal dose-response model). If the bottom of the curve does not fit between −20% & 20% inhibition, it is set to 0% inhibition. If the top of the curve does not fit between 70% and 130% inhibition, it is set to 100% inhibition.

Kinase-Specific Assay Conditions—Direct Format

ABL1

The 2×ABL1/Tyr 02 mixture is prepared in 50 mM HEPES pH 7.5, 0.01% BRIJ-35, 10 mM MgCl2, 1 mM EGTA. The final 10 μL Kinase Reaction consists of 0.29-1.26 ng ABL1 and 2 μM Tyr 02 in 50 mM HEPES pH 7.5, 0.01% BRIJ-35, 10 mM MgCl2, 1 mM EGTA. After the 1 hour Kinase Reaction incubation, 5 μL of a 1:128 dilution of Development Reagent A is added.

AURKA (Aurora A)

The 2×AURKA (Aurora A)/Ser/Thr 01 mixture is prepared in 50 mM HEPES pH 7.5, 0.01% BRIJ-35, 10 mM MgCl2, 1 mM EGTA. The final 10 μL Kinase Reaction consists of 0.91-8.56 ng AURKA (Aurora A) and 2 μM Ser/Thr 01 in 50 mM HEPES pH 7.5, 0.01% BRIJ-35, 10 mM MgCl2, 1 mM EGTA. After the 1 hour Kinase Reaction incubation, 5 μL of a 1:4096 dilution of Development Reagent A is added.

CDK5/p35

The 2×CDK5/p35/Ser/Thr 12 mixture is prepared in 50 mM HEPES pH 7.5, 0.01% BRIJ-35, 10 mM MgCl2, 1 mM EGTA. The final 10 μL Kinase Reaction consists of 0.14-1.3 ng CDK5/p35 and 2 μM Ser/Thr 12 in 50 mM HEPES pH 7.5, 0.01% BRIJ-35, 10 mM MgCl2, 1 mM EGTA. After the 1 hour Kinase Reaction incubation, 5 μL of a 1:4096 dilution of Development Reagent A is added.

CSF1R (FMS)

The 2×CSF1R (FMS)/Tyr 01 mixture is prepared in 50 mM HEPES pH 7.5, 0.01% BRIJ-35, 10 mM MgCl2, 1 mM EGTA. The final 10 μL Kinase Reaction consists of 0.2-40 ng CSF1R (FMS) and 2 μM Tyr 01 in 50 mM HEPES pH 7.5, 0.01% BRIJ-35, 10 mM MgCl2, 1 mM EGTA. After the 1 hour Kinase Reaction incubation, 5 μL of a 1:256 dilution of Development Reagent B is added.

FGFR1

The 2×FGFR1/Tyr 04 mixture is prepared in 50 mM HEPES pH 7.5, 0.01% BRIJ-35, 10 mM MgCl2, 4 mM MnCl2, 1 mM EGTA, 2 mM DTT. The final 10 μL Kinase Reaction consists of 0.44-2.45 ng FGFR1 and 2 μM Tyr 04 in 50 mM HEPES pH 7.5, 0.01% BRIJ-35, 10 mM MgCl2, 2 mM MnCl2, 1 mM EGTA, 1 mM DTT. After the 1 hour Kinase Reaction incubation, 5 μL of a 1:64 dilution of Development Reagent B is added.

FGFR2

The 2×FGFR2/Tyr 04 mixture is prepared in 50 mM HEPES pH 7.5, 0.01% BRIJ-35, 10 mM MgCl2, 4 mM MnCl2, 1 mM EGTA, 2 mM DTT. The final 10 μL Kinase Reaction consists of 0.19-1.99 ng FGFR2 and 2 μM Tyr 04 in 50 mM HEPES pH 7.5, 0.01% BRIJ-35, 10 mM MgCl2, 2 mM MnCl2, 1 mM EGTA, 1 mM DTT. After the 1 hour Kinase Reaction incubation, 5 μL of a 1:64 dilution of Development Reagent B is added.

FLT4 (VEGFR3)

The 2×FLT4 (VEGFR3)/Tyr 04 mixture is prepared in 50 mM HEPES pH 7.5, 0.01% BRIJ-35, 10 mM MgCl2, 4 mM MnCl2, 1 mM EGTA, 2 mM DTT. The final 10 μL Kinase Reaction consists of 2-10.5 ng FLT4 (VEGFR3) and 2 μM Tyr 04 in 50 mM HEPES pH 7.5, 0.01% BRIJ-35, 10 mM MgCl2, 2 mM MnCl2, 1 mM EGTA, 1 mM DTT. After the 1 hour Kinase Reaction incubation, 5 μL of a 1:64 dilution of Development Reagent B is added.

KDR (VEGFR2)

The 2×KDR (VEGFR2)/Tyr 01 mixture is prepared in 50 mM HEPES pH 7.5, 0.01% BRIJ-35, 10 mM MgCl2, 1 mM EGTA. The final 10 μL Kinase Reaction consists of 1-30 ng KDR (VEGFR2) and 2 μM Tyr 01 in 50 mM HEPES pH 7.5, 0.01% BRIJ-35, 10 mM MgCl2, 1 mM EGTA. After the 1 hour Kinase Reaction incubation, 5 μL of a 1:256 dilution of Development Reagent B is added.

LYN B

The 2×LYN B/Tyr 02 mixture is prepared in 50 mM HEPES pH 7.5, 0.01% BRIJ-35, 10 mM MgCl2, 1 mM EGTA. The final 10 μL Kinase Reaction consists of 0.85-14.8 ng LYN B and 2 μM Tyr 02 in 50 mM HEPES pH 7.5, 0.01% BRIJ-35, 10 mM MgCl2, 1 mM EGTA. After the 1 hour Kinase Reaction incubation, 5 μL of a 1:128 dilution of Development Reagent A is added.

MAP4K2 (GCK)

The 2×MAP4K2 (GCK)/Ser/Thr 07 mixture is prepared in 50 mM HEPES pH 7.5, 0.01% BRIJ-35, 10 mM MgCl2, 1 mM EGTA. The final 10 μL Kinase Reaction consists of 0.11-3 ng MAP4K2 (GCK) and 2 μM Ser/Thr 07 in 50 mM HEPES pH 7.5, 0.01% BRIJ-35, 10 mM MgCl2, 1 mM EGTA. After the 1 hour Kinase Reaction incubation, 5 μL of a 1:45000 dilution of Development Reagent A is added.

MAP4K4 (HGK)

The 2×MAP4K4 (HGK)/Ser/Thr 07 mixture is prepared in 50 mM HEPES pH 7.5, 0.01% BRIJ-35, 10 mM MgCl2, 1 mM EGTA. The final 10 μL Kinase Reaction consists of 0.36-1.82 ng MAP4K4 (HGK) and 2 μM Ser/Thr 07 in 50 mM HEPES pH 7.5, 0.01% BRIJ-35, 10 mM MgCl2, 1 mM EGTA. After the 1 hour Kinase Reaction incubation, 5 μL of a 1:45000 dilution of Development Reagent A is added.

PDGFRA (PDGFR alpha)

The 2×PDGFRA (PDGFR alpha)/Tyr 04 mixture is prepared in 50 mM HEPES pH 7.5, 0.01% BRIJ-35, 10 mM MgCl2, 4 mM MnCl2, 1 mM EGTA, 2 mM DTT. The final 10 μL Kinase Reaction consists of 1.54-22.6 ng PDGFRA (PDGFR alpha) and 2 μM Tyr 04 in 50 mM HEPES pH 7.5, 0.01% BRIJ-35, 10 mM MgCl2, 2 mM MnCl2, 1 mM EGTA, 1 mM DTT. After the 1 hour Kinase Reaction incubation, 5 μL of a 1:64 dilution of Development Reagent B is added.

PTK2 (FAK)

The 2×PTK2 (FAK)/Tyr 07 mixture is prepared in 50 mM HEPES pH 7.5, 0.01% BRIJ-35, 10 mM MgCl2, 1 mM EGTA. The final 10 μL Kinase Reaction consists of 12.5-100 ng PTK2 (FAK) and 2 μM Tyr 07 in 50 mM HEPES pH 7.5, 0.01% BRIJ-35, 10 mM MgCl2, 1 mM EGTA. After the 1 hour Kinase Reaction incubation, 5 μL of a 1:16 dilution of Development Reagent B is added.

RET

The 2×RET/Tyr 02 mixture is prepared in 50 mM HEPES pH 7.5, 0.01% BRIJ-35, 10 mM MgCl2, 1 mM EGTA. The final 10 μL Kinase Reaction consists of 0.49-3.64 ng RET and 2 μM Tyr 02 in 50 mM HEPES pH 7.5, 0.01% BRIJ-35, 10 mM MgCl2, 1 mM EGTA. After the 1 hour Kinase Reaction incubation, 5 μL of a 1:128 dilution of Development Reagent A is added.

RPS6 KB1 (p70S6K)

The 2×RPS6 KB1 (p70S6K)/Ser/Thr 07 mixture is prepared in 50 mM HEPES pH 7.5, 0.01% BRIJ-35, 10 mM MgCl2, 1 mM EGTA. The final 10 μL Kinase Reaction consists of 2.87-17.7 ng RPS6 KB1 (p70S6K) and 2 μM Ser/Thr 07 in 50 mM HEPES pH 7.5, 0.01% BRIJ-35, 10 mM MgCl2, 1 mM EGTA. After the 1 hour Kinase Reaction incubation, 5 μL of a 1:45000 dilution of Development Reagent A is added.

TABLE 5

Table of Kinase ATP Km Bins and Inhibitor Validation

| Kinase | Z'-Lyte Substrate | ATP Km app [μM] | ATP Bin (μM) | Inhibitor | IC50 [nM] |
|---|---|---|---|---|---|
| ABL1 | Tyr 02 | 12 | 10 | Tyrphostin AG1478 | 421 |
| AURKA (Aurora A) | Ser/Thr 01 | 10 | 10 | Staurosporine | 3.72 |
| CDK5/p35 | Ser/Thr 12 | 8 | 10 | Staurosporine | 4.69 |
| CSF1R (FMS) | Tyr 01 | 450 | 500 | Tyrphostin AG1478 | 4420 |
| FGFR1 | Tyr 04 | 20 | 25 | Staurosporine | 8.36 |
| FGFR2 | Tyr 04 | 1 | 5 | Staurosporine | 3.03 |
| FLT4 (VEGFR3) | Tyr 04 | 3.8 | 5 | Staurosporine | 4.54 |
| KDR (VEGFR2) | Tyr 01 | 78 | 75 | Staurosporine | 5.98 |
| LYN B | Tyr 02 | 25 | 25 | Tyrphostin AG1478 | 242 |
| MAP4K2 (GCK) | Ser/Thr 07 | 109 | 100 | Staurosporine | 0.655 |
| MAP4K4 (HGK) | Ser/Thr 07 | 12.7 | 10 | Staurosporine | 1.21 |
| PDGFRA (PDGFR alpha) | Tyr 04 | 9 | 10 | Staurosporine | 5.25 |
| PTK2 (FAK) | Tyr 07 | 45 | 50 | Staurosporine | 60.5 |
| RET | Tyr 02 | 11 | 10 | Staurosporine | 3.18 |
| RPS6KB1 (p70S6K) | Ser/Thr 07 | 17 | 10 | Staurosporine | 2.74 |

The table below provides specifications and data around each kinase. The representative IC50 value with a known inhibitor for each kinase was determined at the ATP bin nearest to the ATP Km app, unless indicated with an asterisk (*) in which case the IC50 value was determined at 100 μM ATP.

TABLE 6

Kinase inhibition of structurally closest prior art compounds (examples 263, 293 and 302 of WO09/155551) in mean % inhibition at 10 μmolar compound concentration tested at ATP concentrations matching the respective kinase's Michaelis-Menten constant Km (Km app)

| Example no. in WO09/ 155551 | Compound Concentration [nM] | [ATP] Tested | Kinase Tested | % Inhibition mean | No. of kinases with >80% inhibition |
|---|---|---|---|---|---|
| 263 | 10000 | Km app | ABL1 | 99 | 15/15 |
| | 10000 | Km app | AURKA (Aurora A) | 99 | |
| | 10000 | Km app | CDK5/p35 | 83 | |
| | 10000 | Km app | CSF1R (FMS) | 93 | |
| | 10000 | Km app | FGFR1 | 99 | |
| | 10000 | Km app | FGFR2 | 102 | |
| | 10000 | Km app | FLT4 (VEGFR3) | 103 | |
| | 10000 | Km app | KDR (VEGFR2) | 99 | |
| | 10000 | Km app | LYN B | 98 | |
| | 10000 | Km app | MAP4K2 (GCK) | 98 | |
| | 10000 | Km app | MAP4K4 (HGK) | 98 | |
| | 10000 | Km app | PDGFRA (PDGFR alpha) | 86 | |
| | 10000 | Km app | PTK2 (FAK) | 101 | |
| | 10000 | Km app | RET | 96 | |
| | 10000 | Km app | RPS6KB1 (p70S6K) | 93 | |
| 293 | 10000 | Km app | ABL1 | 97 | 15/15 |
| | 10000 | Km app | AURKA (Aurora A) | 89 | |
| | 10000 | Km app | CDK5/p35 | 90 | |
| | 10000 | Km app | CSF1R (FMS) | 90 | |
| | 10000 | Km app | FGFR1 | 93 | |
| | 10000 | Km app | FGFR2 | 90 | |
| | 10000 | Km app | FLT4 (VEGFR3) | 94 | |
| | 10000 | Km app | KDR (VEGFR2) | 98 | |
| | 10000 | Km app | LYN B | 89 | |
| | 10000 | Km app | MAP4K2 (GCK) | 94 | |
| | 10000 | Km app | MAP4K4 (HGK) | 95 | |
| | 10000 | Km app | PDGFRA (PDGFR alpha) | 88 | |
| | 10000 | Km app | PTK2 (FAK) | 94 | |
| | 10000 | Km app | RET | 94 | |
| | 10000 | Km app | RPS6KB1 (p70S6K) | 85 | |
| 302 | 10000 | Km app | ABL1 | 104 | 15/15 |
| | 10000 | Km app | AURKA (Aurora A) | 98 | |
| | 10000 | Km app | CDK5/p35 | 88 | |
| | 10000 | Km app | CSF1R (FMS) | 95 | |
| | 10000 | Km app | FGFR1 | 97 | |
| | 10000 | Km app | FGFR2 | 98 | |
| | 10000 | Km app | FLT4 (VEGFR3) | 96 | |
| | 10000 | Km app | KDR (VEGFR2) | 101 | |
| | 10000 | Km app | LYN B | 97 | |
| | 10000 | Km app | MAP4K2 (GCK) | 99 | |
| | 10000 | Km app | MAP4K4 (HGK) | 99 | |
| | 10000 | Km app | PDGFRA (PDGFR alpha) | 89 | |
| | 10000 | Km app | PTK2 (FAK) | 86 | |
| | 10000 | Km app | RET | 98 | |
| | 10000 | Km app | RPS6KB1 (p70S6K) | 86 | |

TABLE 7

Kinase inhibition of selected compounds of the present invention in mean % inhibition at 10 μmolar compound concentration tested at ATP concentrations matching the respective kinase's Michaelis-Menten constant Km (Km app)

| Example no. | Compound Concentration [nM] | [ATP] Tested | Kinase Tested | % Inhibition mean | No. of kinases with <40% inhibition |
|---|---|---|---|---|---|
| 9 | 10000 | Km app | ABL1 | 63 | 7/15 |
|  | 10000 | Km app | AURKA (Aurora A) | 57 |  |
|  | 10000 | Km app | CDK5/p35 | 42 |  |
|  | 10000 | Km app | CSF1R (FMS) | 82 |  |
|  | 10000 | Km app | FGFR1 | 35 |  |
|  | 10000 | Km app | FGFR2 | 46 |  |
|  | 10000 | Km app | FLT4 (VEGFR3) | 86 |  |
|  | 10000 | Km app | KDR (VEGFR2) | 30 |  |
|  | 10000 | Km app | LYN B | 18 |  |
|  | 10000 | Km app | MAP4K2 (GCK) | 43 |  |
|  | 10000 | Km app | MAP4K4 (HGK) | 6 |  |
|  | 10000 | Km app | PDGFRA (PDGFR alpha) | 59 |  |
|  | 10000 | Km app | PTK2 (FAK) | 7 |  |
|  | 10000 | Km app | RET | 39 |  |
|  | 10000 | Km app | RPS6KB1 (p70S6K) | 3 |  |
| 10 | 10000 | Km app | ABL1 | 1 | 13/15 |
|  | 10000 | Km app | AURKA (Aurora A) | 4 |  |
|  | 10000 | Km app | CDK5/p35 | 44 |  |
|  | 10000 | Km app | CSF1R (FMS) | 42 |  |
|  | 10000 | Km app | FGFR1 | 15 |  |
|  | 10000 | Km app | FGFR2 | 14 |  |
|  | 10000 | Km app | FLT4 (VEGFR3) | 22 |  |
|  | 10000 | Km app | KDR (VEGFR2) | −2 |  |
|  | 10000 | Km app | LYN B | 17 |  |
|  | 10000 | Km app | MAP4K2 (GCK) | 8 |  |
|  | 10000 | Km app | MAP4K4 (HGK) | 37 |  |
|  | 10000 | Km app | PDGFRA (PDGFR alpha) | 8 |  |
|  | 10000 | Km app | PTK2 (FAK) | 13 |  |
|  | 10000 | Km app | RET | 18 |  |
|  | 10000 | Km app | RPS6KB1 (p70S6K) | 2 |  |
| 40 | 10000 | Km app | ABL1 | 9 | 13/15 |
|  | 10000 | Km app | AURKA (Aurora A) | 13 |  |
|  | 10000 | Km app | CDK5/p35 | 61 |  |
|  | 10000 | Km app | CSF1R (FMS) | 25 |  |
|  | 10000 | Km app | FGFR1 | 27 |  |
|  | 10000 | Km app | FGFR2 | 17 |  |
|  | 10000 | Km app | FLT4 (VEGFR3) | 16 |  |
|  | 10000 | Km app | KDR (VEGFR2) | −10 |  |
|  | 10000 | Km app | LYN B | 20 |  |
|  | 10000 | Km app | MAP4K2 (GCK) | 13 |  |
|  | 10000 | Km app | MAP4K4 (HGK) | 45 |  |
|  | 10000 | Km app | PDGFRA (PDGFR alpha) | 5 |  |
|  | 10000 | Km app | PTK2 (FAK) | 18 |  |
|  | 10000 | Km app | RET | 18 |  |
|  | 10000 | Km app | RPS6KB1 (p70S6K) | 19 |  |
| 42 | 10000 | Km app | ABL1 | 19 | 15/15 |
|  | 10000 | Km app | AURKA (Aurora A) | −2 |  |
|  | 10000 | Km app | CDK5/p35 | 39 |  |
|  | 10000 | Km app | CSF1R (FMS) | 34 |  |
|  | 10000 | Km app | FGFR1 | 16 |  |
|  | 10000 | Km app | FGFR2 | 26 |  |
|  | 10000 | Km app | FLT4 (VEGFR3) | 31 |  |
|  | 10000 | Km app | KDR (VEGFR2) | −3 |  |
|  | 10000 | Km app | LYN B | 19 |  |
|  | 10000 | Km app | MAP4K2 (GCK) | 21 |  |
|  | 10000 | Km app | MAP4K4 (HGK) | 37 |  |
|  | 10000 | Km app | PDGFRA (PDGFR alpha) | 12 |  |
|  | 10000 | Km app | PTK2 (FAK) | 26 |  |
|  | 10000 | Km app | RET | 29 |  |
|  | 10000 | Km app | RPS6KB1 (p70S6K) | 6 |  |
| R-42 | 10000 | Km app | ABL1 | 14 | 14/15 |
|  | 10000 | Km app | AURKA (Aurora A) | 3 |  |
|  | 10000 | Km app | CDK5/p35 | 39 |  |
|  | 10000 | Km app | CSF1R (FMS) | 31 |  |
|  | 10000 | Km app | FGFR1 | 16 |  |
|  | 10000 | Km app | FGFR2 | 30 |  |
|  | 10000 | Km app | FLT4 (VEGFR3) | 36 |  |
|  | 10000 | Km app | KDR (VEGFR2) | 10 |  |
|  | 10000 | Km app | LYN B | 26 |  |
|  | 10000 | Km app | MAP4K2 (GCK) | 25 |  |
|  | 10000 | Km app | MAP4K4 (HGK) | 56 |  |
|  | 10000 | Km app | PDGFRA (PDGFR alpha) | 18 |  |
|  | 10000 | Km app | PTK2 (FAK) | 28 |  |
|  | 10000 | Km app | RET | 23 |  |
|  | 10000 | Km app | RPS6KB1 (p70S6K) | 22 |  |
| 43 | 10000 | Km app | ABL1 | 17 | 14/15 |
|  | 10000 | Km app | AURKA (Aurora A) | −17 |  |
|  | 10000 | Km app | CDK5/p35 | 36 |  |
|  | 10000 | Km app | CSF1R (FMS) | 28 |  |
|  | 10000 | Km app | FGFR1 | 15 |  |
|  | 10000 | Km app | FGFR2 | 14 |  |
|  | 10000 | Km app | FLT4 (VEGFR3) | 11 |  |
|  | 10000 | Km app | KDR (VEGFR2) | −3 |  |
|  | 10000 | Km app | LYN B | 22 |  |
|  | 10000 | Km app | MAP4K2 (GCK) | 9 |  |
|  | 10000 | Km app | MAP4K4 (HGK) | 40 |  |
|  | 10000 | Km app | PDGFRA (PDGFR alpha) | 16 |  |
|  | 10000 | Km app | PTK2 (FAK) | 19 |  |
|  | 10000 | Km app | RET | 26 |  |
|  | 10000 | Km app | RPS6KB1 (p70S6K) | 3 |  |

TABLE 7-continued

Kinase inhibition of selected compounds of the present invention in mean % inhibition at 10 μmolar compound concentration tested at ATP concentrations matching the respective kinase's Michaelis-Menten constant Km (Km app)

| Example no. | Compound Concentration [nM] | [ATP] Tested | Kinase Tested | % Inhibition mean | No. of kinases with <40% inhibition |
|---|---|---|---|---|---|
| 44 | 10000 | Km app | ABL1 | 13 | 13/15 |
|  | 10000 | Km app | AURKA (Aurora A) | 7 |  |
|  | 10000 | Km app | CDK5/p35 | 25 |  |
|  | 10000 | Km app | CSF1R (FMS) | 43 |  |
|  | 10000 | Km app | FGFR1 | 20 |  |
|  | 10000 | Km app | FGFR2 | 22 |  |
|  | 10000 | Km app | FLT4 (VEGFR3) | 43 |  |
|  | 10000 | Km app | KDR (VEGFR2) | 3 |  |
|  | 10000 | Km app | LYN B | 21 |  |
|  | 10000 | Km app | MAP4K2 (GCK) | 26 |  |
|  | 10000 | Km app | MAP4K4 (HGK) | 37 |  |
|  | 10000 | Km app | PDGFRA (PDGFR alpha) | 5 |  |
|  | 10000 | Km app | PTK2 (FAK) | 15 |  |
|  | 10000 | Km app | RET | 20 |  |
|  | 10000 | Km app | RPS6KB1 (p70S6K) | 12 |  |
| 45 | 10000 | Km app | ABL1 | 24 | 14/15 |
|  | 10000 | Km app | AURKA (Aurora A) | −13 |  |
|  | 10000 | Km app | CDK5/p35 | 8 |  |
|  | 10000 | Km app | CSF1R (FMS) | 40 |  |
|  | 10000 | Km app | FGFR1 | 9 |  |
|  | 10000 | Km app | FGFR2 | 16 |  |
|  | 10000 | Km app | FLT4 (VEGFR3) | 33 |  |
|  | 10000 | Km app | KDR (VEGFR2) | −10 |  |
|  | 10000 | Km app | LYN B | 15 |  |
|  | 10000 | Km app | MAP4K2 (GCK) | 24 |  |
|  | 10000 | Km app | MAP4K4 (HGK) | 2 |  |
|  | 10000 | Km app | PDGFRA (PDGFR alpha) | 30 |  |
|  | 10000 | Km app | PTK2 (FAK) | 20 |  |
|  | 10000 | Km app | RET | 30 |  |
|  | 10000 | Km app | RPS6KB1 (p70S6K) | 7 |  |
| 46 | 10000 | Km app | ABL1 | 10 | 14/15 |
|  | 10000 | Km app | AURKA (Aurora A) | 14 |  |
|  | 10000 | Km app | CDK5/p35 | 34 |  |
|  | 10000 | Km app | CSF1R (FMS) | 24 |  |
|  | 10000 | Km app | FGFR1 | 21 |  |
|  | 10000 | Km app | FGFR2 | 26 |  |
|  | 10000 | Km app | FLT4 (VEGFR3) | 29 |  |
|  | 10000 | Km app | KDR (VEGFR2) | 3 |  |
|  | 10000 | Km app | LYN B | 23 |  |
|  | 10000 | Km app | MAP4K2 (GCK) | 19 |  |
|  | 10000 | Km app | MAP4K4 (HGK) | 48 |  |
|  | 10000 | Km app | PDGFRA (PDGFR alpha) | 25 |  |
|  | 10000 | Km app | PTK2 (FAK) | 24 |  |
|  | 10000 | Km app | RET | 26 |  |
|  | 10000 | Km app | RPS6KB1 (p70S6K) | 6 |  |
| 47 | 10000 | Km app | ABL1 | 3 | 15/15 |
|  | 10000 | Km app | AURKA (Aurora A) | 10 |  |
|  | 10000 | Km app | CDK5/p35 | 13 |  |
|  | 10000 | Km app | CSF1R (FMS) | 15 |  |
|  | 10000 | Km app | FGFR1 | 21 |  |
|  | 10000 | Km app | FGFR2 | 21 |  |
|  | 10000 | Km app | FLT4 (VEGFR3) | 13 |  |
|  | 10000 | Km app | KDR (VEGFR2) | 6 |  |
|  | 10000 | Km app | LYN B | 21 |  |
|  | 10000 | Km app | MAP4K2 (GCK) | 11 |  |
|  | 10000 | Km app | MAP4K4 (HGK) | 32 |  |
|  | 10000 | Km app | PDGFRA (PDGFR alpha) | 10 |  |
|  | 10000 | Km app | PTK2 (FAK) | 19 |  |
|  | 10000 | Km app | RET | 23 |  |
|  | 10000 | Km app | RPS6KB1 (p70S6K) | 12 |  |
| 48 | 10000 | Km app | ABL1 | 13 | 14/15 |
|  | 10000 | Km app | AURKA (Aurora A) | −14 |  |
|  | 10000 | Km app | CDK5/p35 | 38 |  |
|  | 10000 | Km app | CSF1R (FMS) | 15 |  |
|  | 10000 | Km app | FGFR1 | 18 |  |
|  | 10000 | Km app | FGFR2 | 22 |  |
|  | 10000 | Km app | FLT4 (VEGFR3) | 19 |  |
|  | 10000 | Km app | KDR (VEGFR2) | 2 |  |
|  | 10000 | Km app | LYN B | 22 |  |
|  | 10000 | Km app | MAP4K2 (GCK) | 16 |  |
|  | 10000 | Km app | MAP4K4 (HGK) | 50 |  |
|  | 10000 | Km app | PDGFRA (PDGFR alpha) | 19 |  |
|  | 10000 | Km app | PTK2 (FAK) | 24 |  |
|  | 10000 | Km app | RET | 18 |  |
|  | 10000 | Km app | RPS6KB1 (p70S6K) | 15 |  |
| 49 | 10000 | Km app | ABL1 | 15 | 14/15 |
|  | 10000 | Km app | AURKA (Aurora A) | −14 |  |
|  | 10000 | Km app | CDK5/p35 | 7 |  |
|  | 10000 | Km app | CSF1R (FMS) | 34 |  |
|  | 10000 | Km app | FGFR1 | 9 |  |
|  | 10000 | Km app | FGFR2 | 31 |  |
|  | 10000 | Km app | FLT4 (VEGFR3) | 33 |  |
|  | 10000 | Km app | KDR (VEGFR2) | 8 |  |
|  | 10000 | Km app | LYN B | 25 |  |
|  | 10000 | Km app | MAP4K2 (GCK) | 17 |  |
|  | 10000 | Km app | MAP4K4 (HGK) | 54 |  |
|  | 10000 | Km app | PDGFRA (PDGFR alpha) | 29 |  |
|  | 10000 | Km app | PTK2 (FAK) | 32 |  |
|  | 10000 | Km app | RET | 22 |  |
|  | 10000 | Km app | RPS6KB1 (p70S6K) | 33 |  |

TABLE 7-continued

Kinase inhibition of selected compounds of the present invention in mean % inhibition at 10 μmolar compound concentration tested at ATP concentrations matching the respective kinase's Michaelis-Menten constant Km (Km app)

| Example no. | Compound Concentration [nM] | [ATP] Tested | Kinase Tested | % Inhibition mean | No. of kinases with <40% inhibition |
|---|---|---|---|---|---|
| 51 | 10000 | Km app | ABL1 | 6 | 15/15 |
| | 10000 | Km app | AURKA (Aurora A) | 8 | |
| | 10000 | Km app | CDK5/p35 | 23 | |
| | 10000 | Km app | CSF1R (FMS) | 9 | |
| | 10000 | Km app | FGFR1 | 5 | |
| | 10000 | Km app | FGFR2 | 28 | |
| | 10000 | Km app | FLT4 (VEGFR3) | 15 | |
| | 10000 | Km app | KDR (VEGFR2) | −10 | |
| | 10000 | Km app | LYN B | 7 | |
| | 10000 | Km app | MAP4K2 (GCK) | 22 | |
| | 10000 | Km app | MAP4K4 (HGK) | −8 | |
| | 10000 | Km app | PDGFRA (PDGFR alpha) | 14 | |
| | 10000 | Km app | PTK2 (FAK) | 27 | |
| | 10000 | Km app | RET | 2 | |
| | 10000 | Km app | RPS6KB1 (p70S6K) | 1 | |
| 54 | 10000 | Km app | ABL1 | 12 | 15/15 |
| | 10000 | Km app | AURKA (Aurora A) | 18 | |
| | 10000 | Km app | CDK5/p35 | 18 | |
| | 10000 | Km app | CSF1R (FMS) | 27 | |
| | 10000 | Km app | FGFR1 | −3 | |
| | 10000 | Km app | FGFR2 | 25 | |
| | 10000 | Km app | FLT4 (VEGFR3) | 38 | |
| | 10000 | Km app | KDR (VEGFR2) | 5 | |
| | 10000 | Km app | LYN B | 15 | |
| | 10000 | Km app | MAP4K2 (GCK) | 27 | |
| | 10000 | Km app | MAP4K4 (HGK) | 25 | |
| | 10000 | Km app | PDGFRA (PDGFR alpha) | 30 | |
| | 10000 | Km app | PTK2 (FAK) | 14 | |
| | 10000 | Km app | RET | 15 | |
| | 10000 | Km app | RPS6KB1 (p70S6K) | 1 | |
| 55 | 10000 | Km app | ABL1 | 21 | 13/15 |
| | 10000 | Km app | AURKA (Aurora A) | 15 | |
| | 10000 | Km app | CDK5/p35 | 13 | |
| | 10000 | Km app | CSF1R (FMS) | 34 | |
| | 10000 | Km app | FGFR1 | 12 | |
| | 10000 | Km app | FGFR2 | 13 | |
| | 10000 | Km app | FLT4 (VEGFR3) | 42 | |
| | 10000 | Km app | KDR (VEGFR2) | 12 | |
| | 10000 | Km app | LYN B | 27 | |
| | 10000 | Km app | MAP4K2 (GCK) | 30 | |
| | 10000 | Km app | MAP4K4 (HGK) | 51 | |
| | 10000 | Km app | PDGFRA (PDGFR alpha) | 16 | |
| | 10000 | Km app | PTK2 (FAK) | 8 | |
| | 10000 | Km app | RET | 21 | |
| | 10000 | Km app | RPS6KB1 (p70S6K) | 11 | |
| 56 | 10000 | Km app | ABL1 | 20 | 12/15 |
| | 10000 | Km app | AURKA (Aurora A) | 27 | |
| | 10000 | Km app | CDK5/p35 | 52 | |
| | 10000 | Km app | CSF1R (FMS) | 58 | |
| | 10000 | Km app | FGFR1 | 20 | |
| | 10000 | Km app | FGFR2 | 19 | |
| | 10000 | Km app | FLT4 (VEGFR3) | 35 | |
| | 10000 | Km app | KDR (VEGFR2) | 6 | |
| | 10000 | Km app | LYN B | 19 | |
| | 10000 | Km app | MAP4K2 (GCK) | 16 | |
| | 10000 | Km app | MAP4K4 (HGK) | 48 | |
| | 10000 | Km app | PDGFRA (PDGFR alpha) | 21 | |
| | 10000 | Km app | PTK2 (FAK) | 15 | |
| | 10000 | Km app | RET | 27 | |
| | 10000 | Km app | RPS6KB1 (p70S6K) | 1 | |
| 57 | 10000 | Km app | ABL1 | 11 | 12/15 |
| | 10000 | Km app | AURKA (Aurora A) | 7 | |
| | 10000 | Km app | CDK5/p35 | 26 | |
| | 10000 | Km app | CSF1R (FMS) | 72 | |
| | 10000 | Km app | FGFR1 | 23 | |
| | 10000 | Km app | FGFR2 | 22 | |
| | 10000 | Km app | FLT4 (VEGFR3) | 43 | |
| | 10000 | Km app | KDR (VEGFR2) | 18 | |
| | 10000 | Km app | LYN B | 20 | |
| | 10000 | Km app | MAP4K2 (GCK) | 13 | |
| | 10000 | Km app | MAP4K4 (HGK) | 58 | |
| | 10000 | Km app | PDGFRA (PDGFR alpha) | 29 | |
| | 10000 | Km app | PTK2 (FAK) | 16 | |
| | 10000 | Km app | RET | 21 | |
| | 10000 | Km app | RPS6KB1 (p70S6K) | 14 | |
| 59 | 10000 | Km app | ABL1 | 19 | 13/15 |
| | 10000 | Km app | AURKA (Aurora A) | −21 | |
| | 10000 | Km app | CDK5/p35 | 28 | |
| | 10000 | Km app | CSF1R (FMS) | 42 | |
| | 10000 | Km app | FGFR1 | 22 | |
| | 10000 | Km app | FGFR2 | 11 | |
| | 10000 | Km app | FLT4 (VEGFR3) | 39 | |
| | 10000 | Km app | KDR (VEGFR2) | −8 | |
| | 10000 | Km app | LYN B | 22 | |
| | 10000 | Km app | MAP4K2 (GCK) | 22 | |
| | 10000 | Km app | MAP4K4 (HGK) | 57 | |
| | 10000 | Km app | PDGFRA (PDGFR alpha) | 5 | |
| | 10000 | Km app | PTK2 (FAK) | 16 | |
| | 10000 | Km app | RET | 29 | |
| | 10000 | Km app | RPS6KB1 (p70S6K) | 6 | |

TABLE 7-continued

Kinase inhibition of selected compounds of the present invention in mean % inhibition at 10 μmolar compound concentration tested at ATP concentrations matching the respective kinase's Michaelis-Menten constant Km (Km app)

| Example no. | Compound Concentration [nM] | [ATP] Tested | Kinase Tested | % Inhibition mean | No. of kinases with <40% inhibition |
|---|---|---|---|---|---|
| R-61 | 10000 | Km app | ABL1 | 3 | 15/15 |
| | 10000 | Km app | AURKA (Aurora A) | −8 | |
| | 10000 | Km app | CDK5/p35 | 25 | |
| | 10000 | Km app | CSF1R (FMS) | 18 | |
| | 10000 | Km app | FGFR1 | 15 | |
| | 10000 | Km app | FGFR2 | 12 | |
| | 10000 | Km app | FLT4 (VEGFR3) | 21 | |
| | 10000 | Km app | KDR (VEGFR2) | 2 | |
| | 10000 | Km app | LYN B | 17 | |
| | 10000 | Km app | MAP4K2 (GCK) | 3 | |
| | 10000 | Km app | MAP4K4 (HGK) | 24 | |
| | 10000 | Km app | PDGFRA (PDGFR alpha) | 18 | |
| | 10000 | Km app | PTK2 (FAK) | 16 | |
| | 10000 | Km app | RET | 20 | |
| | 10000 | Km app | RPS6KB1 (p70S6K) | 3 | |
| S-61 | 10000 | Km app | ABL1 | 13 | 15/15 |
| | 10000 | Km app | AURKA (Aurora A) | −21 | |
| | 10000 | Km app | CDK5/p35 | 10 | |
| | 10000 | Km app | CSF1R (FMS) | 18 | |
| | 10000 | Km app | FGFR1 | 13 | |
| | 10000 | Km app | FGFR2 | 13 | |
| | 10000 | Km app | FLT4 (VEGFR3) | 24 | |
| | 10000 | Km app | KDR (VEGFR2) | −15 | |
| | 10000 | Km app | LYN B | 8 | |
| | 10000 | Km app | MAP4K2 (GCK) | 12 | |
| | 10000 | Km app | MAP4K4 (HGK) | 11 | |
| | 10000 | Km app | PDGFRA (PDGFR alpha) | 13 | |
| | 10000 | Km app | PTK2 (FAK) | 23 | |
| | 10000 | Km app | RET | 23 | |
| | 10000 | Km app | RPS6KB1 (p70S6K) | 22 | |
| 63 | 10000 | Km app | ABL1 | 15 | 12/15 |
| | 10000 | Km app | AURKA (Aurora A) | 29 | |
| | 10000 | Km app | CDK5/p35 | 47 | |
| | 10000 | Km app | CSF1R (FMS) | 48 | |
| | 10000 | Km app | FGFR1 | 18 | |
| | 10000 | Km app | FGFR2 | 16 | |
| | 10000 | Km app | FLT4 (VEGFR3) | 32 | |
| | 10000 | Km app | KDR (VEGFR2) | 8 | |
| | 10000 | Km app | LYN B | 13 | |
| | 10000 | Km app | MAP4K2 (GCK) | 14 | |
| | 10000 | Km app | MAP4K4 (HGK) | 48 | |
| | 10000 | Km app | PDGFRA (PDGFR alpha) | 20 | |
| | 10000 | Km app | PTK2 (FAK) | 13 | |
| | 10000 | Km app | RET | 20 | |
| | 10000 | Km app | RPS6KB1 (p70S6K) | 3 | |
| 67 | 10000 | Km app | ABL1 | 11 | 14/15 |
| | 10000 | Km app | AURKA (Aurora A) | 6 | |
| | 10000 | Km app | CDK5/p35 | 35 | |
| | 10000 | Km app | CSF1R (FMS) | 29 | |
| | 10000 | Km app | FGFR1 | 21 | |
| | 10000 | Km app | FGFR2 | 30 | |
| | 10000 | Km app | FLT4 (VEGFR3) | 33 | |
| | 10000 | Km app | KDR (VEGFR2) | 15 | |
| | 10000 | Km app | LYN B | 20 | |
| | 10000 | Km app | MAP4K2 (GCK) | 14 | |
| | 10000 | Km app | MAP4K4 (HGK) | 49 | |
| | 10000 | Km app | PDGFRA (PDGFR alpha) | 20 | |
| | 10000 | Km app | PTK2 (FAK) | 27 | |
| | 10000 | Km app | RET | 24 | |
| | 10000 | Km app | RPS6KB1 (p70S6K) | 23 | |
| 68 | 10000 | Km app | ABL1 | 28 | 11/15 |
| | 10000 | Km app | AURKA (Aurora A) | 39 | |
| | 10000 | Km app | CDK5/p35 | 44 | |
| | 10000 | Km app | CSF1R (FMS) | 66 | |
| | 10000 | Km app | FGFR1 | 23 | |
| | 10000 | Km app | FGFR2 | 28 | |
| | 10000 | Km app | FLT4 (VEGFR3) | 52 | |
| | 10000 | Km app | KDR (VEGFR2) | 18 | |
| | 10000 | Km app | LYN B | 22 | |
| | 10000 | Km app | MAP4K2 (GCK) | 28 | |
| | 10000 | Km app | MAP4K4 (HGK) | 42 | |
| | 10000 | Km app | PDGFRA (PDGFR alpha) | 23 | |
| | 10000 | Km app | PTK2 (FAK) | 28 | |
| | 10000 | Km app | RET | 28 | |
| | 10000 | Km app | RPS6KB1 (p70S6K) | 17 | |
| 69 | 10000 | Km app | ABL1 | 13 | 15/15 |
| | 10000 | Km app | AURKA (Aurora A) | 25 | |
| | 10000 | Km app | CDK5/p35 | 28 | |
| | 10000 | Km app | CSF1R (FMS) | 8 | |
| | 10000 | Km app | FGFR1 | 20 | |
| | 10000 | Km app | FGFR2 | 1 | |
| | 10000 | Km app | FLT4 (VEGFR3) | 16 | |
| | 10000 | Km app | KDR (VEGFR2) | 8 | |
| | 10000 | Km app | LYN B | 15 | |
| | 10000 | Km app | MAP4K2 (GCK) | 9 | |
| | 10000 | Km app | MAP4K4 (HGK) | 39 | |
| | 10000 | Km app | PDGFRA (PDGFR alpha) | 17 | |
| | 10000 | Km app | PTK2 (FAK) | 24 | |
| | 10000 | Km app | RET | 16 | |
| | 10000 | Km app | RPS6KB1 (p70S6K) | 31 | |

TABLE 7-continued

Kinase inhibition of selected compounds of the present invention in mean % inhibition at 10 µmolar compound concentration tested at ATP concentrations matching the respective kinase's Michaelis-Menten constant Km (Km app)

| Example no. | Compound Concentration [nM] | [ATP] Tested | Kinase Tested | % Inhibition mean | No. of kinases with <40% inhibition |
|---|---|---|---|---|---|
| 70 | 10000 | Km app | ABL1 | 15 | 11/15 |
|  | 10000 | Km app | AURKA (Aurora A) | 51 |  |
|  | 10000 | Km app | CDK5/p35 | 58 |  |
|  | 10000 | Km app | CSF1R (FMS) | 83 |  |
|  | 10000 | Km app | FGFR1 | 18 |  |
|  | 10000 | Km app | FGFR2 | 12 |  |
|  | 10000 | Km app | FLT4 (VEGFR3) | 28 |  |
|  | 10000 | Km app | KDR (VEGFR2) | 12 |  |
|  | 10000 | Km app | LYN B | 22 |  |
|  | 10000 | Km app | MAP4K2 (GCK) | 7 |  |
|  | 10000 | Km app | MAP4K4 (HGK) | 56 |  |
|  | 10000 | Km app | PDGFRA (PDGFR alpha) | 17 |  |
|  | 10000 | Km app | PTK2 (FAK) | 14 |  |
|  | 10000 | Km app | RET | 32 |  |
|  | 10000 | Km app | RPS6KB1 (p70S6K) | −3 |  |
| 71 | 10000 | Km app | ABL1 | 24 | 11/15 |
|  | 10000 | Km app | AURKA (Aurora A) | 42 |  |
|  | 10000 | Km app | CDK5/p35 | 53 |  |
|  | 10000 | Km app | CSF1R (FMS) | 62 |  |
|  | 10000 | Km app | FGFR1 | 19 |  |
|  | 10000 | Km app | FGFR2 | 27 |  |
|  | 10000 | Km app | FLT4 (VEGFR3) | 62 |  |
|  | 10000 | Km app | KDR (VEGFR2) | 17 |  |
|  | 10000 | Km app | LYN B | 24 |  |
|  | 10000 | Km app | MAP4K2 (GCK) | 26 |  |
|  | 10000 | Km app | MAP4K4 (HGK) | 16 |  |
|  | 10000 | Km app | PDGFRA (PDGFR alpha) | 21 |  |
|  | 10000 | Km app | PTK2 (FAK) | 30 |  |
|  | 10000 | Km app | RET | 30 |  |
|  | 10000 | Km app | RPS6KB1 (p70S6K) | 23 |  |
| 73 | 10000 | Km app | ABL1 | 21 | 8/15 |
|  | 10000 | Km app | AURKA (Aurora A) | 85 |  |
|  | 10000 | Km app | CDK5/p35 | 56 |  |
|  | 10000 | Km app | CSF1R (FMS) | 79 |  |
|  | 10000 | Km app | FGFR1 | 32 |  |
|  | 10000 | Km app | FGFR2 | 26 |  |
|  | 10000 | Km app | FLT4 (VEGFR3) | 50 |  |
|  | 10000 | Km app | KDR (VEGFR2) | 8 |  |
|  | 10000 | Km app | LYN B | 31 |  |
|  | 10000 | Km app | MAP4K2 (GCK) | 49 |  |
|  | 10000 | Km app | MAP4K4 (HGK) | 74 |  |
|  | 10000 | Km app | PDGFRA (PDGFR alpha) | 23 |  |
|  | 10000 | Km app | PTK2 (FAK) | 25 |  |
|  | 10000 | Km app | RET | 62 |  |
|  | 10000 | Km app | RPS6KB1 (p70S6K) | 24 |  |

Use in Treatment/Method of Use

The present invention is directed to compounds which are useful in the treatment of a disease, disorder and condition wherein the modulation of the activity of γ-secretase Is of therapeutic benefit, including but not limited to the treatment and/or prevention of all those conditions or diseases which may be affected by the formation of Aβ peptides. According to a further aspect of the invention, compounds of the present invention are useful for the treatment and/or prevention of a disease, disorder or condition selected from the list consisting of Down's syndrome, Abeta-amyloid angiopathy, cerebral amyloid angiopathy, MCI ("mild cognitive impairment"), Alzheimer's Disease, memory loss, attention deficit symptoms associated with Alzheimer's disease, neurodegeneration associated with Alzheimer's disease, diffuse Lewy body type of Alzheimer's Disease, dementia of mixed vascular origin, dementia of degenerative origin, pre-senile dementia, senile dementia, glaucoma and the dry form of age-related macular degeneration.

Another aspect of the present invention relates to a method of treatment of above mentioned diseases and conditions, which method comprises the administration of an effective amount of a compound of the present invention to a human being.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

The invention claimed is:

1. A compound of formula II wherein

R¹ represents

[structures shown]

and

R² represents

[structures shown]

or a pharmaceutically acceptable salt thereof.

2. The compound according to claim 1, wherein R¹ represents
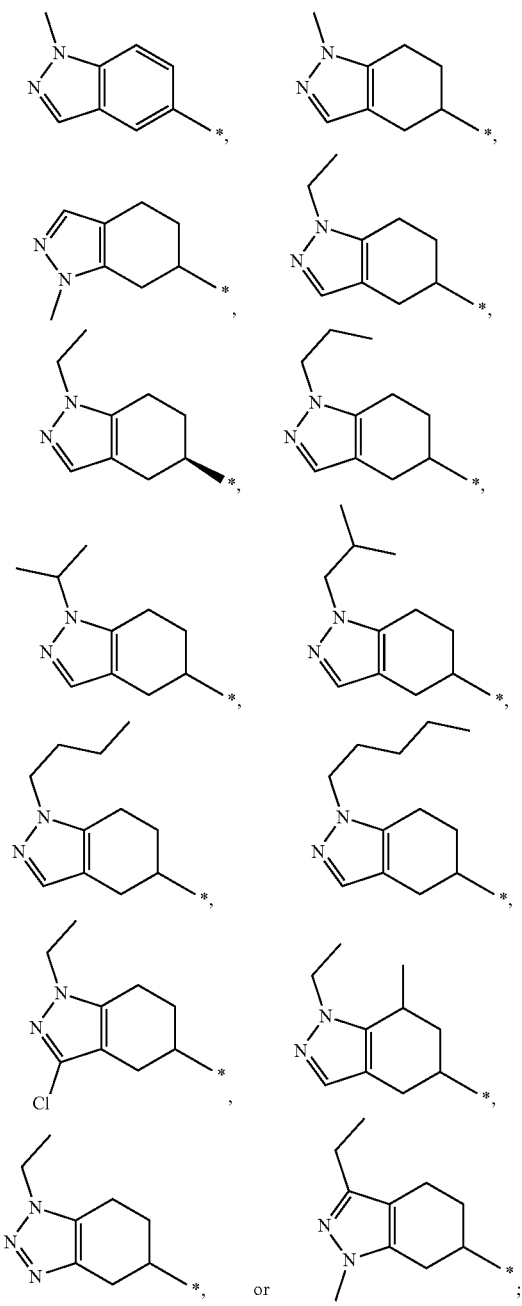
and
R² represents
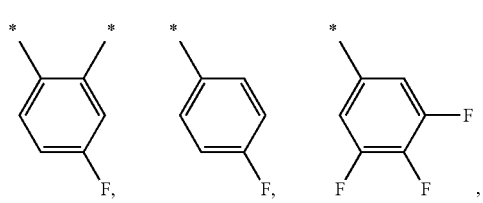
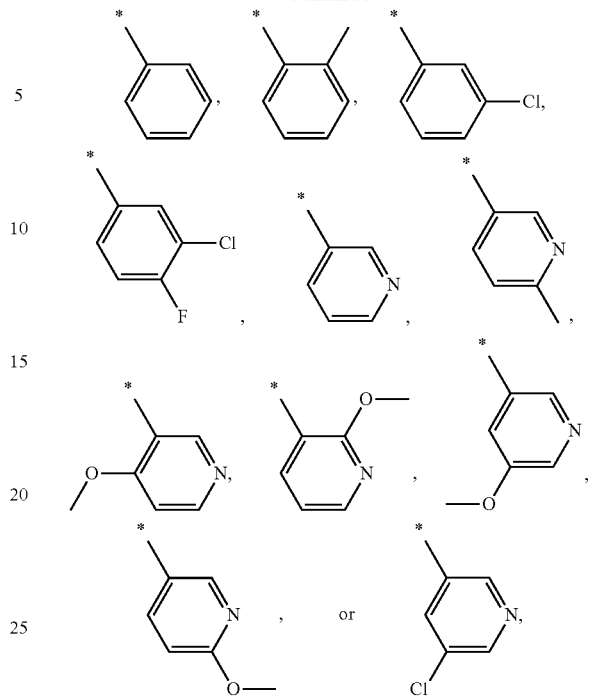
or a pharmaceutically acceptable salt thereof.
3. The compound according to claim 1, selected from the group consisting of
| Ex. no. | Structure |
|---|---|
| 9 | 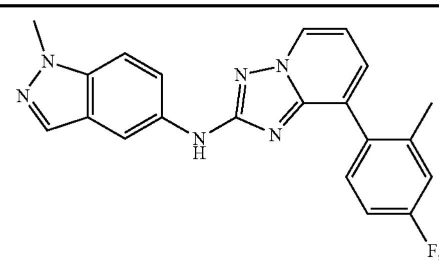 |
| 10 | 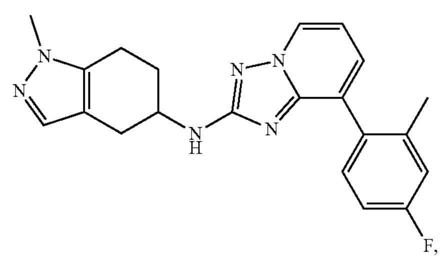 [SMILES: Cc1cc(F)ccc1-c1cccn2nc(NC3CCc4c(cnn4C)C3)nc12] |
| 40 | 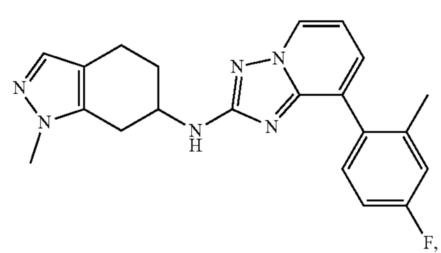 [SMILES: Cc1cc(F)ccc1-c1cccn2nc(NC3CCc4cnn(C)c4C3)nc12] |

| Ex. no. | Structure |
|---|---|
| 41 | 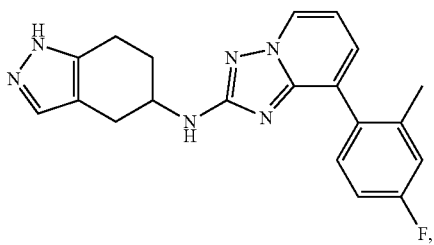 [SMILES: Cc1cc(F)ccc1-c1cccn2nc(NC3CCc4[nH]ncc4C3)nc12] |
| 42 | 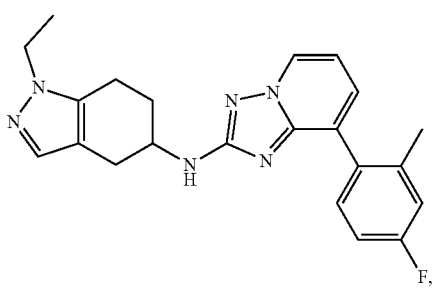 [SMILES: CCn1ncc2c1CCC(Nc1nc3c(-c4ccc(F)cc4C)cccn3n1)C2] |
| R-42 | 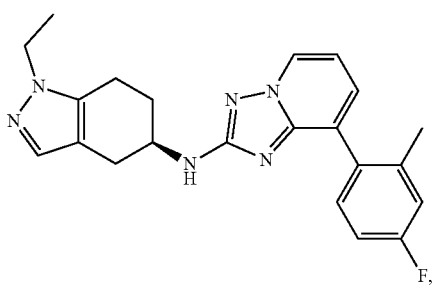 [SMILES: CCn1ncc2c1CC[C@@H](Nc1nc3c(-c4ccc(F)cc4C)cccn3n1)C2] |
| 43 | 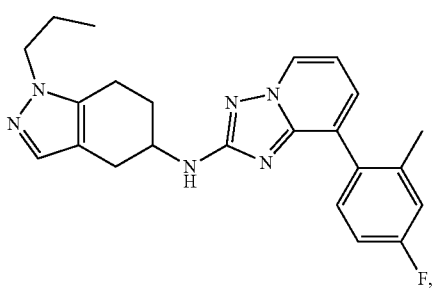 [SMILES: CCCn1ncc2c1CCC(Nc1nc3c(-c4ccc(F)cc4C)cccn3n1)C2] |
| 44 | 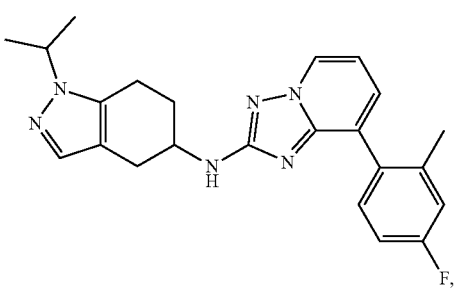 [SMILES: Cc1cc(F)ccc1-c1cccn2nc(NC3CCc4c(cnn4C(C)C)C3)nc12] |
| Ex. no. | Structure |
|---|---|
| 45 | 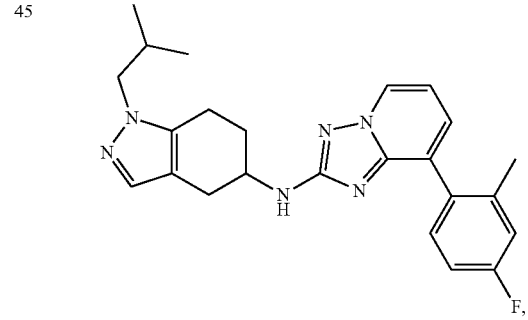 |
| 46 | 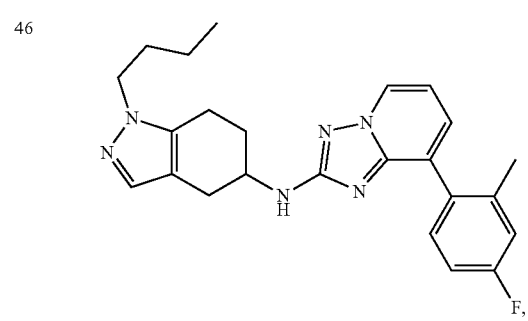 |
| 47 | 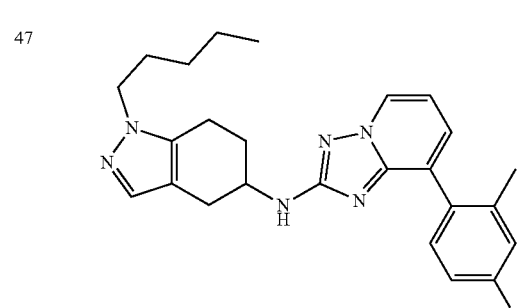 |
| 48 | 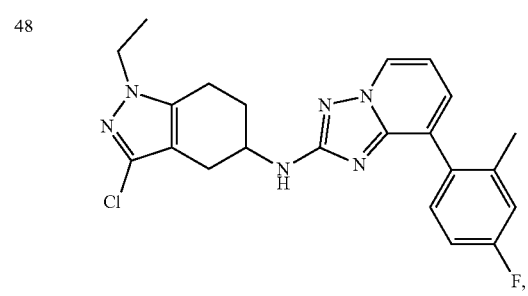 |
| 49 | 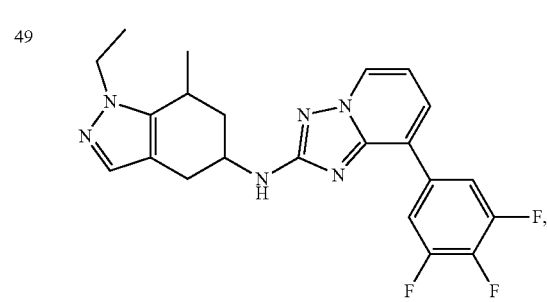 |

| Ex. no. | Structure |
|---|---|
| 50 | 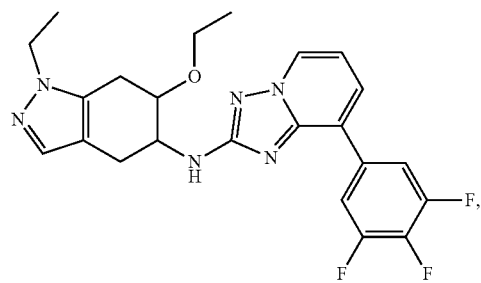 |
| 51 | 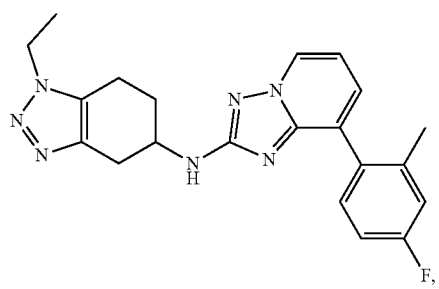 |
| 52 | 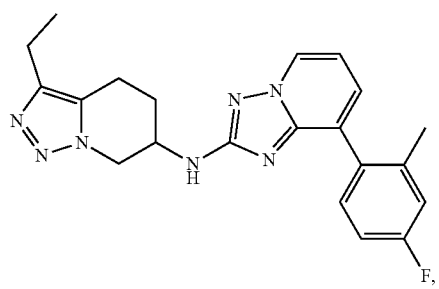 [SMILES: CCc1nnn2c1CCC(Nc1nc3c(-c4ccc(F)cc4C)cccn3n1)C2] |
| 53 | 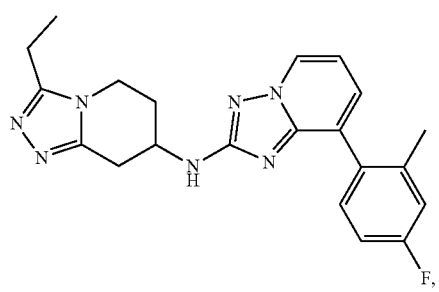 |
| 54 | 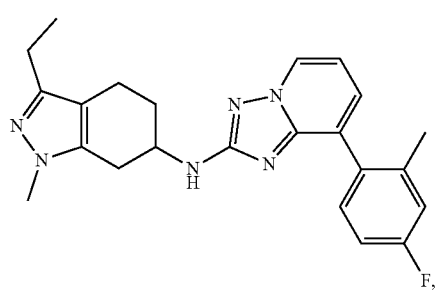 [SMILES: CCc1nn(C)c2c1CCC(Nc1nc3c(-c4ccc(F)cc4C)cccn3n1)C2] |
| Ex. no. | Structure |
|---|---|
| 55 | 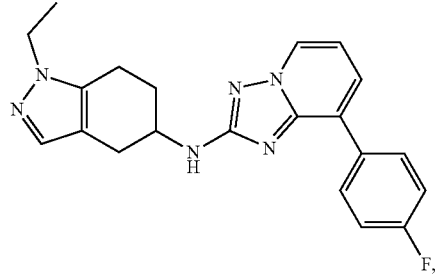 [SMILES: CCn1ncc2c1CCC(Nc1nc3c(-c4ccc(F)cc4)cccn3n1)C2] |
| 56 | 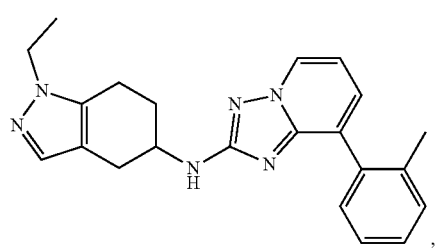 |
| 57 | 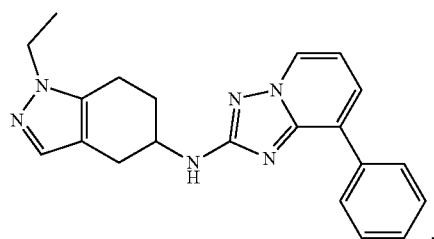 |
| 58 | 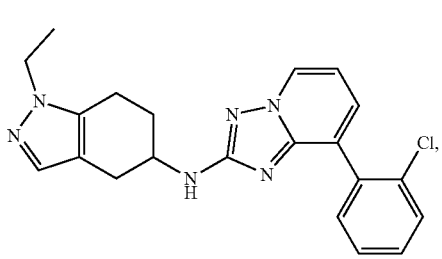 [SMILES: CCn1ncc2c1CCC(Nc1nc3c(-c4ccccc4Cl)cccn3n1)C2] |
| 59 | 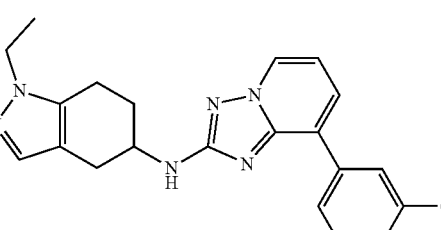 |
| 60 | 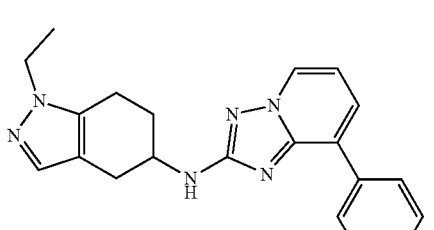 |

| Ex. no. | Structure |
|---|---|
| 61 | 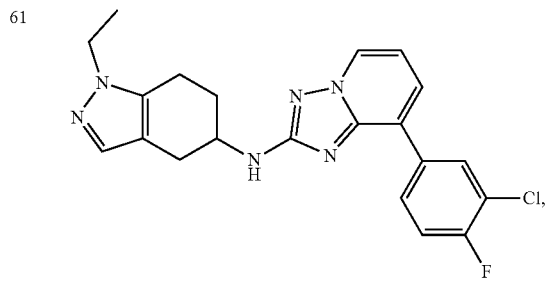 |
| R-61 | 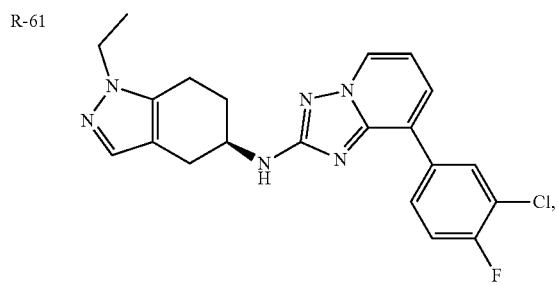 |
| S-61 | 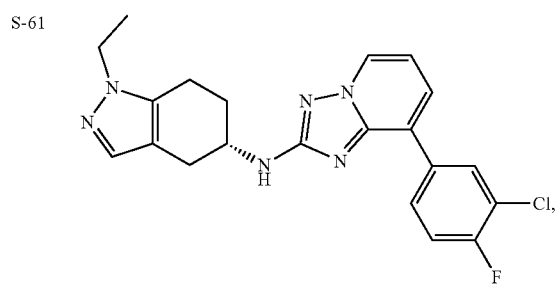 |
| 62 | 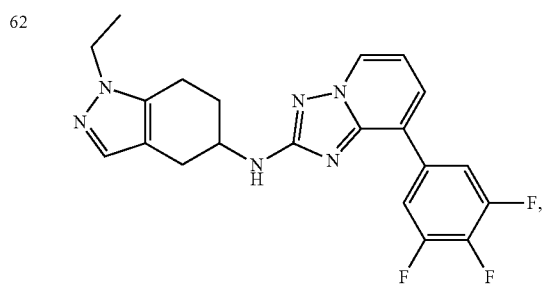 |
| 63 | 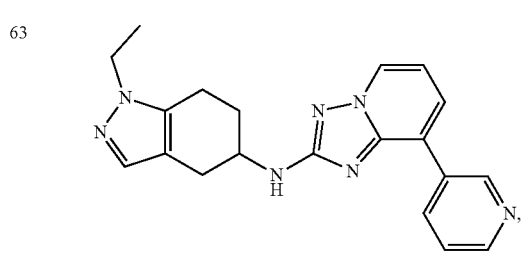 |
| Ex. no. | Structure |
|---|---|
| 64 | 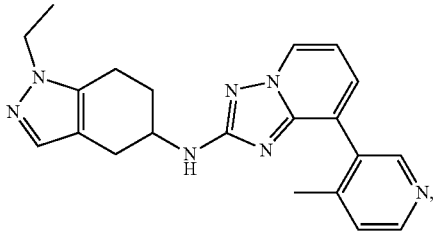 [SMILES: CCn1ncc2c1CCC(Nc1nc3c(-c4cnccc4C)cccn3n1)C2] |
| 65 | 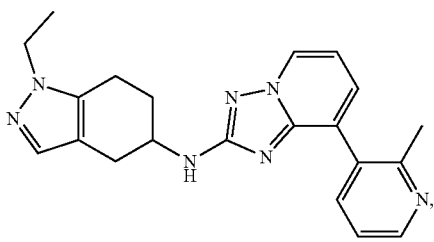 [SMILES: CCn1ncc2c1CCC(Nc1nc3c(-c4cccnc4C)cccn3n1)C2] |
| 66 | 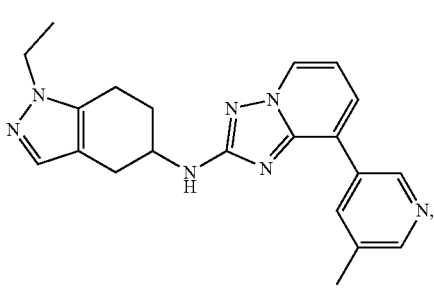 [SMILES: CCn1ncc2c1CCC(Nc1nc3c(-c4cncc(C)c4)cccn3n1)C2] |
| 67 | 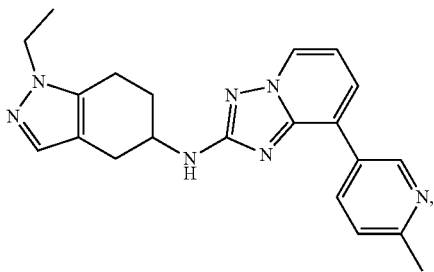 [SMILES: CCn1ncc2c1CCC(Nc1nc3c(-c4ccc(C)nc4)cccn3n1)C2] |
| 68 | 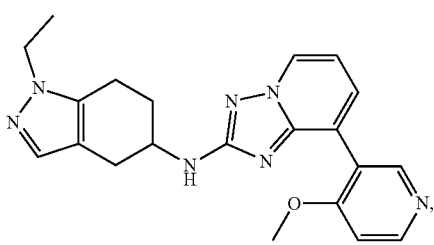 [SMILES: CCn1ncc2c1CCC(Nc1nc3c(-c4cnccc4OC)cccn3n1)C2] |
| 69 | 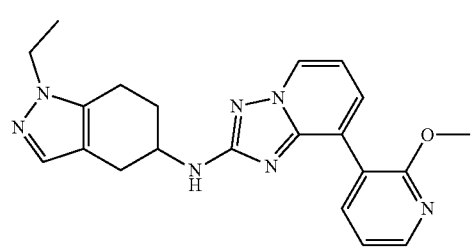 |

| Ex. no. | Structure |
|---|---|
| 70 | [structure] |
| 71 | [structure] |
| 72 | [structure] and |
| 73 | [structure] |

4. A pharmaceutically acceptable salt of a compound according to claim 1.

5. A method for treating a disease, disorder or condition selected from the group consisting of Down's syndrome, Abeta-amyloid angiopathy, cerebral amyloid angiopathy, mild cognitive impairment, Alzheimer's Disease, memory loss, attention deficit symptoms associated with Alzheimer's disease, neurodegeneration associated with Alzheimer's disease, diffuse Lewy body type of Alzheimer's Disease, dementia of mixed vascular origin, dementia of degenerative origin, pre-senile dementia, senile dementia, glaucoma and the dry form of age-related macular degeneration, the method comprising administering a pharmaceutically effective amount of the compound of claim 1, or a pharmaceutically acceptable salt thereof, to a patient in need thereof.

6. A pharmaceutical composition comprising the compound according to claim 1, or a pharmaceutically acceptable salt thereof, in admixture with a pharmaceutically acceptable adjuvant, diluent and/or carrier.

7. The compound according to claim 1 selected from the group consisting of:

| Ex. no. | Structure |
|---|---|
| 9 | [structure] |
| 10 | [structure] |
| 40 | [structure] |
| 41 | [structure] |
| 42 | [structure] |

| Ex. no. | Structure |
|---|---|
| R-42 | 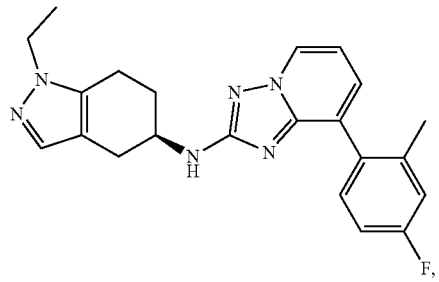 [SMILES: CCn1ncc2c1CC[C@@H](Nc1nc3c(-c4ccc(F)cc4C)cccn3n1)C2] |
| 43 | 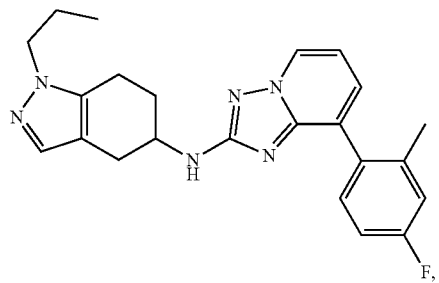 |
| 44 | 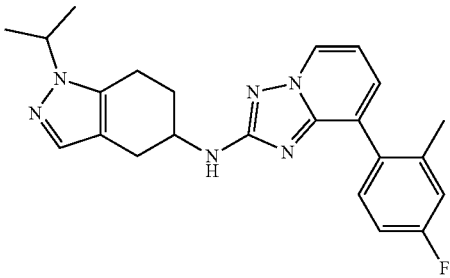 |
| 45 | 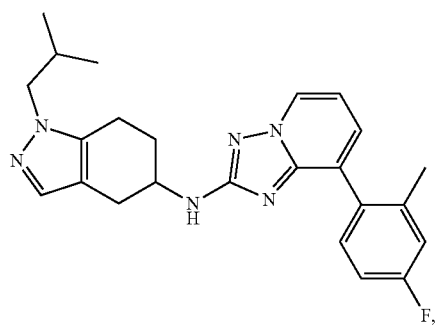 [SMILES: Cc1cc(F)ccc1-c1cccn2nc(NC3CCc4c(cnn4CC(C)C)C3)nc12] |
| 46 | 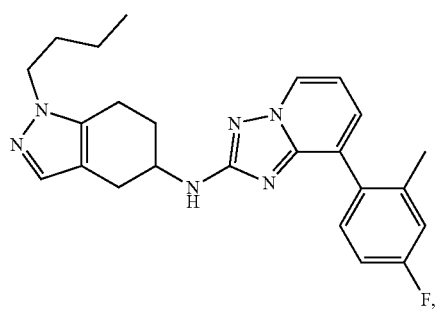 [SMILES: CCCCn1ncc2c1CCC(Nc1nc3c(-c4ccc(F)cc4C)cccn3n1)C2] |
| Ex. no. | Structure |
|---|---|
| 47 | 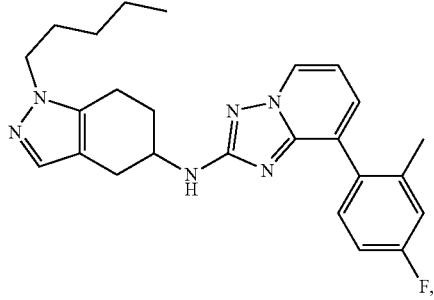 [SMILES: CCCCCn1ncc2c1CCC(Nc1nc3c(-c4ccc(F)cc4C)cccn3n1)C2] |
| 48 | 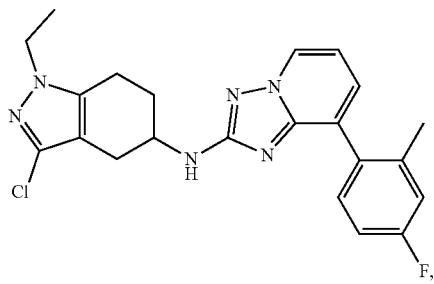 [SMILES: CCn1nc(Cl)c2c1CCC(Nc1nc3c(-c4ccc(F)cc4C)cccn3n1)C2] |
| 49 | 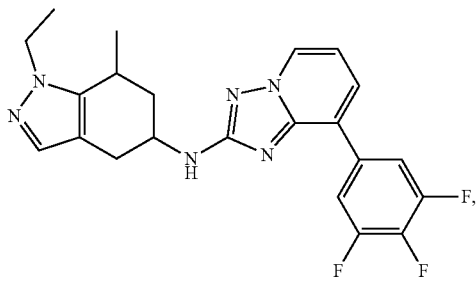 [SMILES: CCn1ncc2c1C(C)CC(Nc1nc3c(-c4cc(F)c(F)c(F)c4)cccn3n1)C2] |
| 50 | 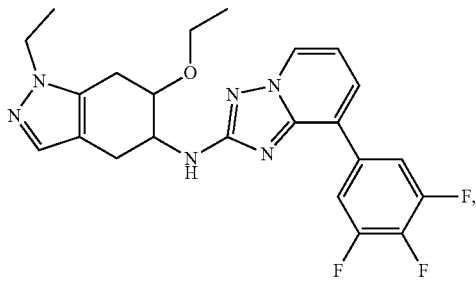 [SMILES: CCOC1Cc2c(cnn2CC)CC1Nc1nc2c(-c3cc(F)c(F)c(F)c3)cccn2n1] |
| 51 | 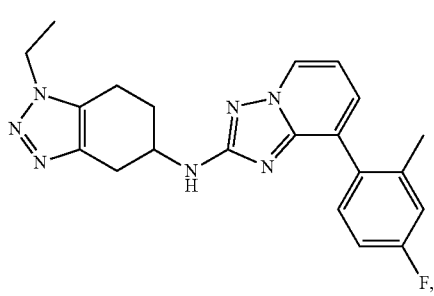 [SMILES: CCn1nnc2c1CCC(Nc1nc3c(-c4ccc(F)cc4C)cccn3n1)C2] |

| Ex. no. | Structure |
|---|---|
| 52 | 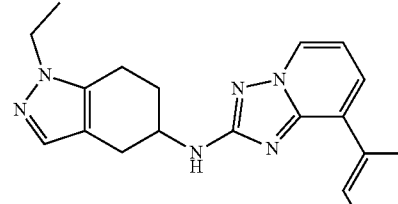 |
| 53 | |
| 54 | |
| 55 | |
| 56 | |
| Ex. no. | Structure |
|---|---|
| 57 | 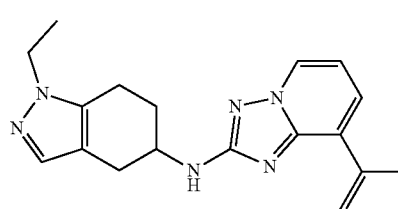 |
| 58 | |
| 59 | |
| 60 | |
| 61 | |
| R-61 | |

| Ex. no. | Structure |
|---|---|
| S-61 | 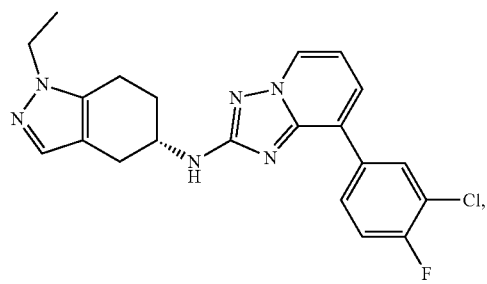 |
| 62 | 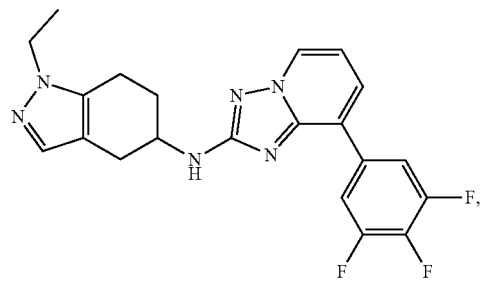 [SMILES: CCn1ncc2c1CCC(Nc1nc3c(-c4cc(F)c(F)c(F)c4)cccn3n1)C2] |
| 63 | 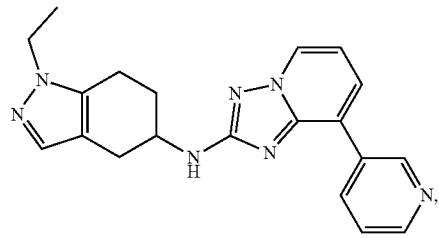 [SMILES: CCn1ncc2c1CCC(Nc1nc3c(-c4cccnc4)cccn3n1)C2] |
| 64 | 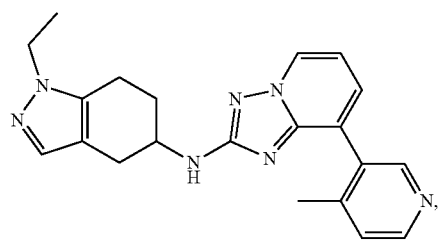 [SMILES: CCn1ncc2c1CCC(Nc1nc3c(-c4cnccc4C)cccn3n1)C2] |
| 65 | 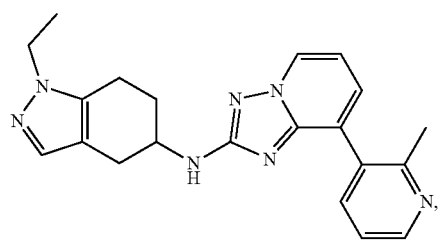 [SMILES: CCn1ncc2c1CCC(Nc1nc3c(-c4cccnc4C)cccn3n1)C2] |
| 66 | 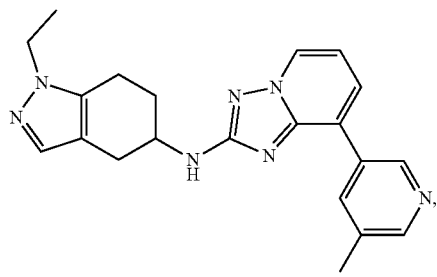 [SMILES: CCn1ncc2c1CCC(Nc1nc3c(-c4cncc(C)c4)cccn3n1)C2] |
| 67 | 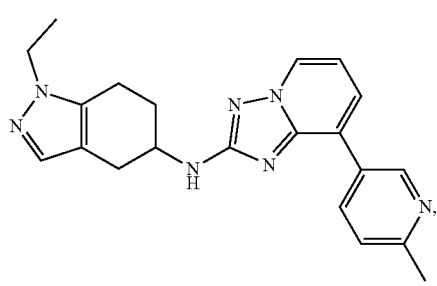 [SMILES: CCn1ncc2c1CCC(Nc1nc3c(-c4ccc(C)nc4)cccn3n1)C2] |
| 68 | 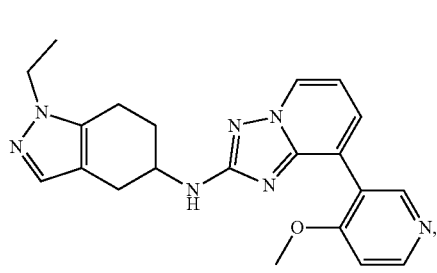 [SMILES: CCn1ncc2c1CCC(Nc1nc3c(-c4cnccc4OC)cccn3n1)C2] |
| 69 | 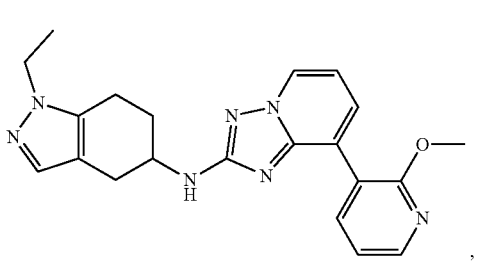 [SMILES: CCn1ncc2c1CCC(Nc1nc3c(-c4cccnc4OC)cccn3n1)C2] |

| Ex. no. | Structure |
|---|---|
| 70 | 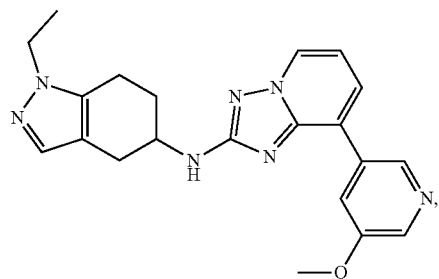 [SMILES: CCn1ncc2c1CCC(Nc1nc3c(-c4cncc(OC)c4)cccn3n1)C2] |
| 71 | 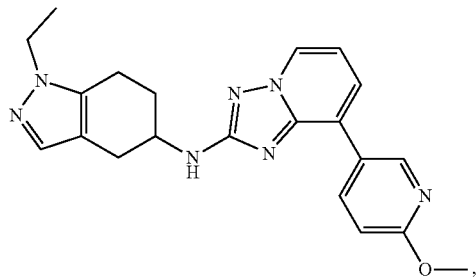 [SMILES: CCn1ncc2c1CCC(Nc1nc3c(-c4ccc(OC)nc4)cccn3n1)C2] |
| Ex. no. | Structure |
|---|---|
| 72 | 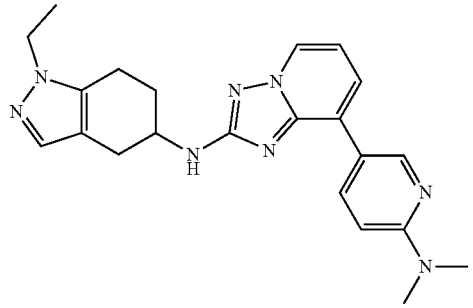 and |
| 73 | 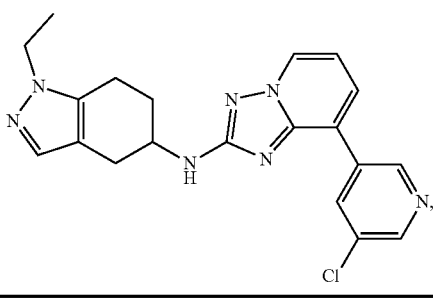 |
or a pharmaceutically acceptable salt thereof.
* * * * *